(12) United States Patent
Moss et al.

(10) Patent No.: US 7,670,806 B2
(45) Date of Patent: Mar. 2, 2010

(54) ADP-RIBOSYL ACCEPTOR HYDROLASE 3 (ARH3) POLYPEPTIDES AND METHODS OF USE

(75) Inventors: Joel Moss, Bethesda, MD (US); Shunya Oka, Niigata (JP); Jiro Kato, Rockville, MD (US); Jianfeng Zhu, Frederick, MD (US); Atsushi Kasamatsu, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/047,185

(22) Filed: Mar. 12, 2008

(65) Prior Publication Data

US 2008/0207555 A1 Aug. 28, 2008

Related U.S. Application Data

(63) Continuation-in-part of application No. PCT/US2006/035771, filed on Sep. 12, 2006.

(60) Provisional application No. 60/716,807, filed on Sep. 13, 2005.

(51) Int. Cl.
*C12P 19/00* (2006.01)
*C12N 9/00* (2006.01)
*C12N 1/20* (2006.01)
*C12N 15/00* (2006.01)
*C07H 21/04* (2006.01)

(52) U.S. Cl. ..................... 435/72; 435/183; 435/252.3; 435/320.1; 536/23.2

(58) Field of Classification Search ....................... None
See application file for complete search history.

(56) References Cited

FOREIGN PATENT DOCUMENTS

WO WO 01/51636 A2 7/2001

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
International Search Report and the Written Opinion for PCT Application No. PCT/US2006/03577, 18 pages, (mailed Jun. 13, 2007).
Masutani et al., "Poly(ADP-ribosyl)ation in relation to cancer and autoimmune disease," *CMLS Cellular and Molecular Life Sciences*, 62:769-783, (2005).
Moss et al., "Molecular and Immunological Characterization of ADP-ribosylarginine Hydrolases," *The Journal of Biological Chemistry*, 267(15):10481-10488, (1992).
Oka et al., "Identification and Characterization of a Mammalian 39-kDa Poly(ADP-ribose) Glycohydrolase," *The Journal of Biological Chemistry*, 281(2):705-713 (Jan. 13, 2006).
Takada et al., "Cloning and Site-directed Mutagenesis of Human ADP-ribosylarginine Hyrolase," *The Journal of Biological Chemistry*, 268(24):17837-17843, (1993).

* cited by examiner

*Primary Examiner*—Christian L Fronda
(74) *Attorney, Agent, or Firm*—Klarquist Sparkman, LLP

(57) ABSTRACT

This disclosure provides methods for catalyzing the release of ADP-ribose from poly(ADP-ribose) or O-acetyl-ADP-ribose. Also provided are methods for modifying DNA repair or chromatin structure by introducing into the cell an agent that modifies the activity of an ARH3 polypeptide, or variant or fragment thereof. Further provided are methods for screening molecules involved in the poly(ADP-ribosyl)ation of proteins or O-acetyl-ADP-ribose content, and method for treating disorders by altering activity of an ARH3 protein.

19 Claims, 16 Drawing Sheets

```
ARH1    1   ....................................................
ARH2    1   ....................................................
ARH3    1   --MAAAMAAAAGGGAGAARSLSRFRGCLAGALLLDCVGSFYEAHLTVDLTSVLRHVQSLEPDPG
                         **

ARH1   49   ----ALDVERERAHDHVHLLATALAALVEAGKAPKLTQRYLLAKHAQDCMRLMGIALGLSVH
ARH2   49   --HLVLSPLELPLTNLLLATALALTTDYWC--LDDLREMVRCLVEIVLKLPERLDPLTIE
ARH3   64   TPG-SERTEALYYTDLLALARGLVQSLL-LKELFDEVLMAHRFLQELK---KLPLRGYGALVVTV

ARH1  106   NAMLLRLGKPN-GL---HLLTHSHEG--HCLAAMFANLHGLLFPHHSQLDLLHQVLIESLLLLHL
ARH2  106   GCALLKLNNYLLAL---HTLLHELHL-LFLAATKALLHLLWKPERLLELLLDLVLCLLLNL
ARH3  124   FKKLLNLKCRD-VFEPALAQLLGLALYLNLLGALLVAGLSLALSSVQDVQKFARLLAQ---LLLAS

ARH1  166   LLTYLDALASLLLTAYVNSRLPLALLKGLMELLLLERKKLIVQLGYLVELNLLQLLSLLQTLLLEN
ARH2  167   LLCGLLSLCTALLLSLAALLKLLVLLLRDMLRAVLLAEELLCRKTIRHTALYQELLLFLLLDAALLF
ARH3  188   SLLLNLLLLQALALHLLLLLES--------------------SLELHFLKQLLLGLLMEDLLLGDALLSV

ARH1  231   IKLLGLL-LGLLSAPTLLLLDLFGVLLIDQFLLTSLLLYS--------LWLSSLLLLLLLLA------
ARH2  232   LLELLKLSKLSLNKALLLDNYDAELLLEKTLLRKWLSE--------SRLLRRLLLLATLLLA----
ARH3  230   LDALLELG-MELLR----LYLSRLLLKIGELLDQALLVTREEVVSELLNLLIAAFESVLLTAILLCFLRCME

ARH1  280   --LLVLRALLDLRKLLAHRALLLLLSLLALALLWWLVMLLFKGLSPLNLLEKHLLYRNRLLLETLLR
ARH2  282   --LLLLTALLLLELTELCHRAMLLPHLLLLELAALLGLLLALLLLLLLLLLALLKGLLLDLLLDKSLLLDDLGA
ARH3  290   PDPEIPSLLFLLLQRTLIYSISLLLLLLLLLTLIALLATLAIALLAYLLGMLLQLLELLWQLLSCLLLGYLETDILLLQ

ARH1  343   LLLSLLGSLLLDTVISL  357
ARH2  345   LLLYLLLSTELLLK-----  354
ARH3  355   SLLHLLVFQLLS------  363
```

B

```
PARG  421   EDRRKEQWETKHQRTERKIPKYVPPHLSPDKKWLGTPIEEMRRLLPRCGIRLPLLRPSANHTVTLL
ARH3    1   ---------------------------------------LAAAAMAAAAGGGAGAARSLSL

PARG  487   VDLLRALLEVPKPFPTHYKDLWLLNKHVKMPCSE-LLNLYLLVEDENLLERTAGSRWELILLLLLLNKFTR
ARH3   23   FRGCLALLALLGDCVGSFYEAHLLTVDLTSVLRHVLSLLELLDPGTPLLSERTEALYYTDDLLLARALVQ
                                                                      **

PARG  550   PQNLLLDALLLKYNVLLYSKKWDFTALILLFWDKVLEEAEAQHLLLYQSLILPLMVKILLLCLPLLICTQPIPL
ARH3   88   SLLALLLAFDEVDMLLLHRFAQEYKKDPLLRGYGAGVVTVFKKLLLNPKCRLLVFEPLLARAQFLL--------

PARG  615   LLLQKMNHSITLLSQEEIASLLANAFFCTFPRLLNLLKMKSELLLLYPLLINLL-LLNLL---------------
ARH3  145   GLLGSYGNGGALL----------------LMLGISLALLSVQLLVQKLLLALLLSAQLTHASSLGYNG

PARG  665   -FEGRSSRKPEKLLKTLLFCYFRRVTLLKKPTGLVTFTRQSLLLLFPEWERCEKPLTRLLHVTYEGTIEE
ARH3  191   AI---------LLQALLAVHLALQGLLSSLEHFLKQLLGHMLLL-------------LLEGDAQSVLDA
                          +                ++

PARG  729   NGQLLLLQVDFANLLF--VLLGGVTSLLGLVQLLLLIRFLINPELIISRLFTEVLDHNECLIITGTEQYSE
ARH3  233   RELLLLEERPTSSLLLKKILLELLDQLLSVTRLLV-----------------------------------
                 ##                   ^^

PARG  792   YTGYALLTYRWSRSHLLDGSERDDLLERLLLTLIVAIDALHFRRYLDQFVPEKMRRLLLNKLLYCGFLLPG
ARH3  264   ---VSLLLGNGIAAFLSVPTAIYLLFLLLMLL-------------------PDPLLIPSLLFNSLQLLTL

PARG  857   VSLLENLLSAVATGNWGCGAFLLLARLKLLLIQILALLAAERDVVYFTTLLDSELMRDIYSMHIFLTER
ARH3  306   IYLLISLL-----------LLLLHTDTIALLTMAGAIAGLL--------YYLMDQVPES----------

PARG  922   KLTVGDVYKLLLRYYNEELLRNCSTPGPDIKLYPFILLHAVESCLLETADHSGLLRTGT  976
ARH3  339   ---------------WQQSLLEG-----------LLEETDILLLQSLHRVFLLKS--  363
```

FIG. 12
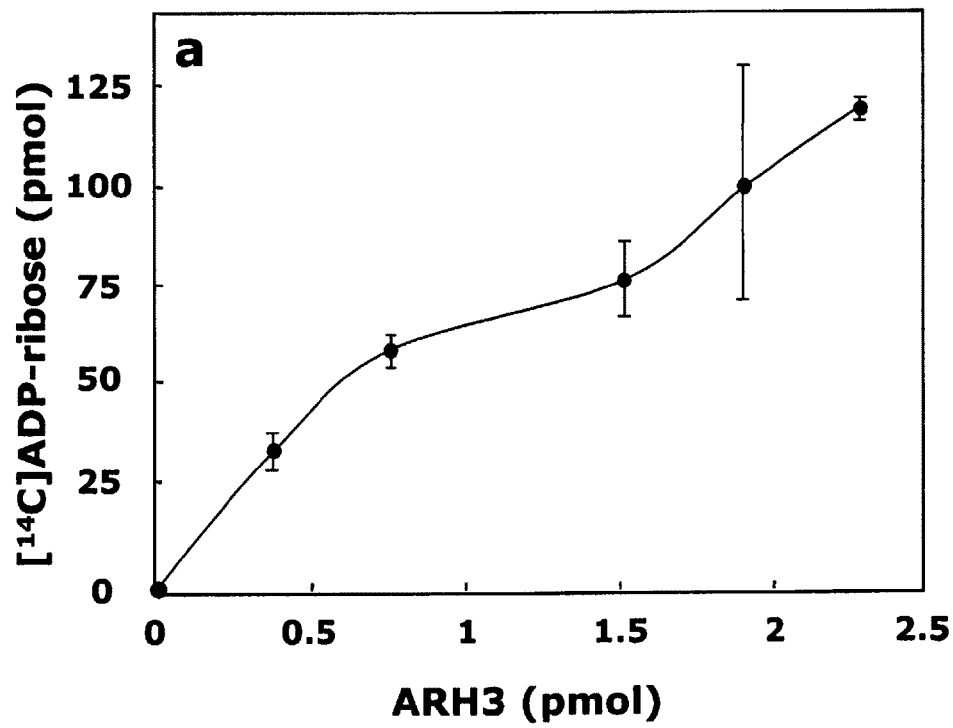
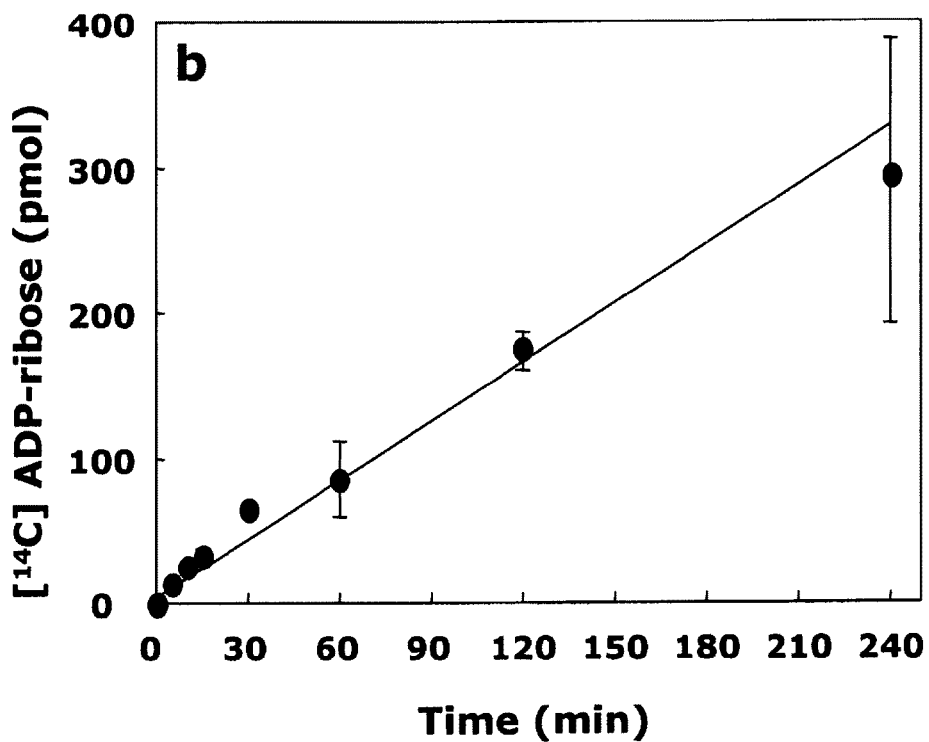

FIG. 13
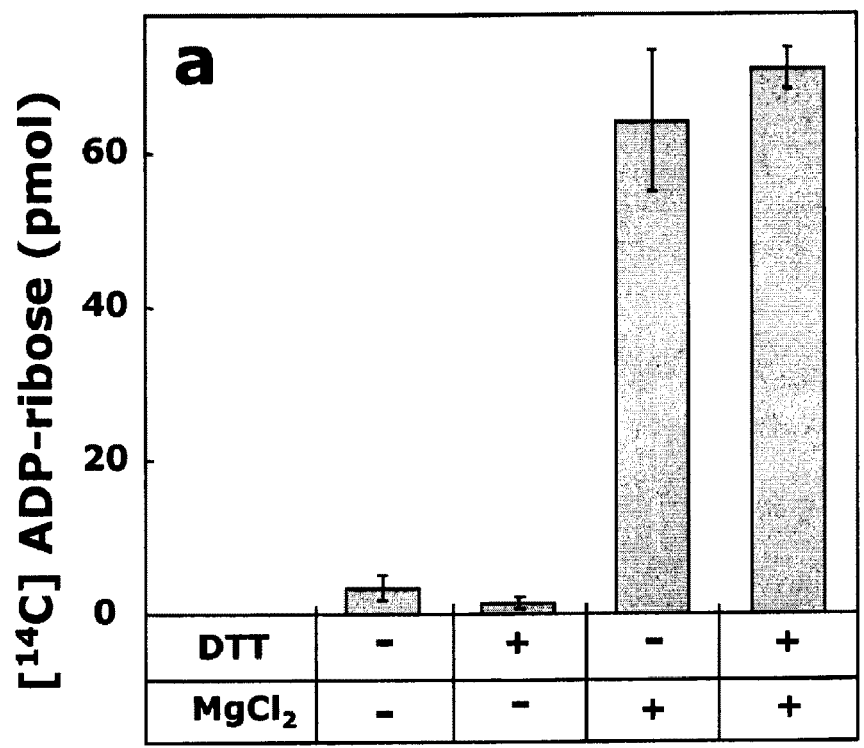
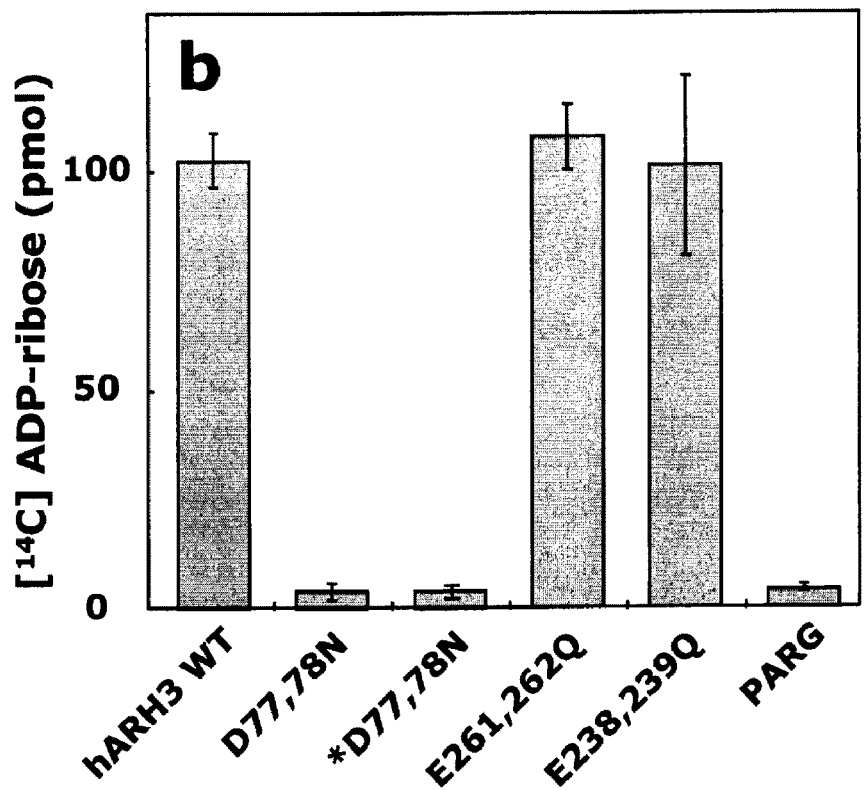

FIG. 14
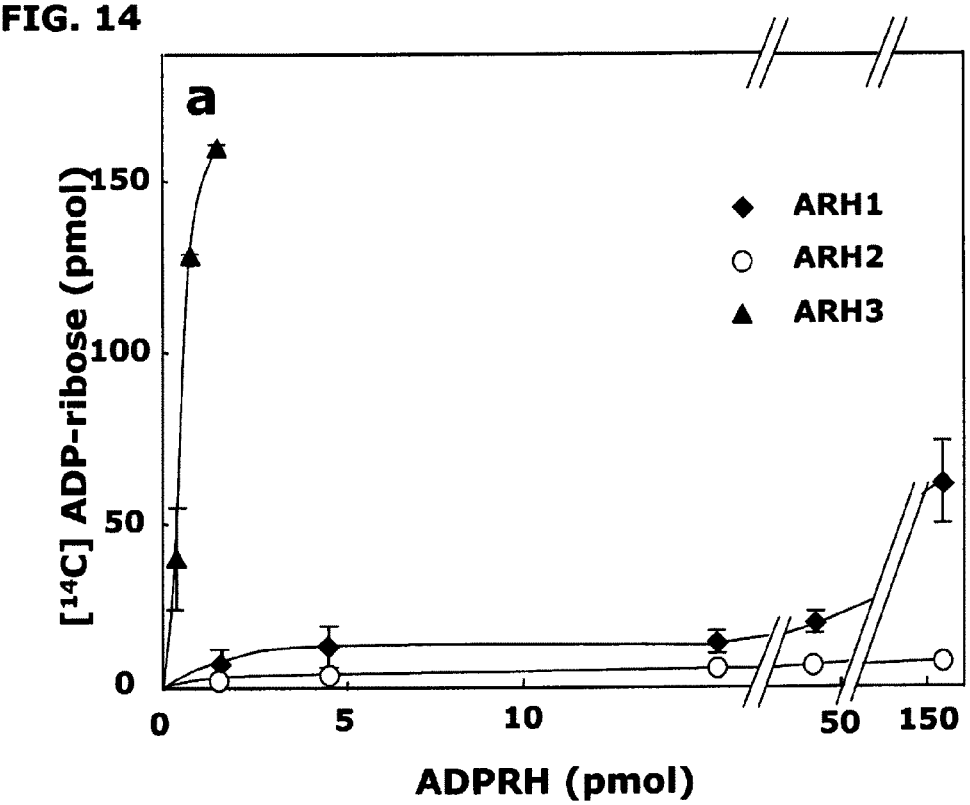
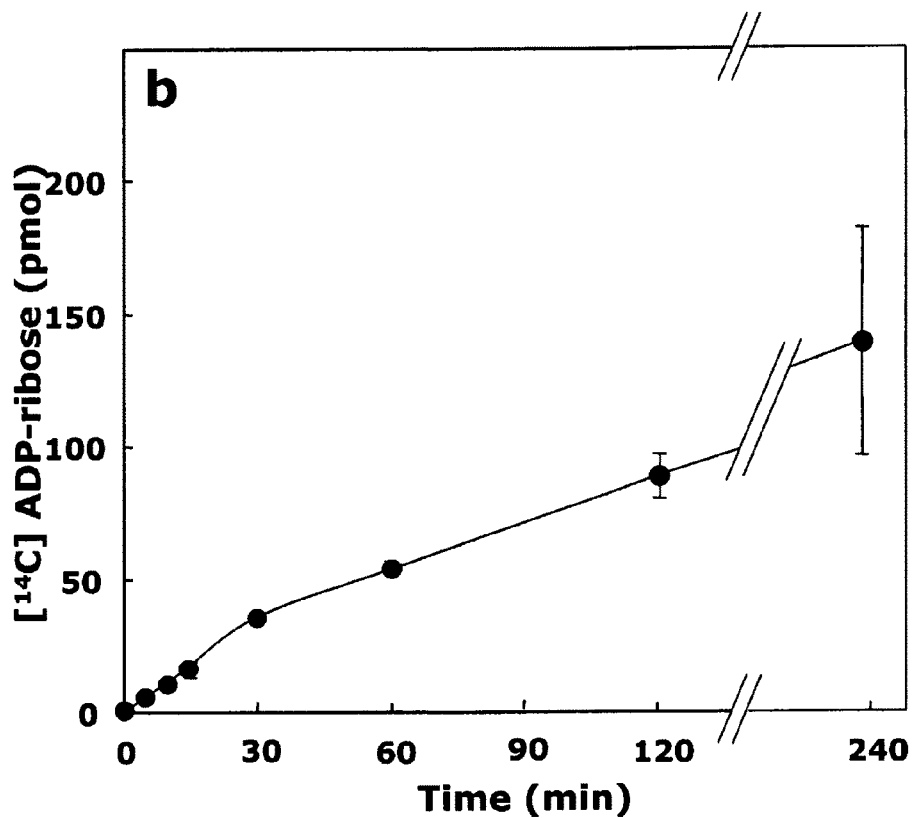

ADP-RIBOSYL ACCEPTOR HYDROLASE 3 (ARH3) POLYPEPTIDES AND METHODS OF USE

PRIORITY CLAIM

This is a continuation-in-part of PCT Application No. PCT/US2006/035771, filed Sep. 12, 2006, which claims the benefit of U.S. Provisional Application No. 60/716,807, filed Sep. 13, 2005. The prior applications are incorporated herein by reference in their entirety.

FIELD

This invention relates to the field of molecular biology, specifically to ADP-ribose acceptor hydrolases and their use.

BACKGROUND

ADP-ribosylation is the post-translational modification of a protein, resulting from transfer of the ADP-ribose moiety of NAD to a specific amino acid in the protein, thereby altering its structure and function (Williamson and Moss (1990) In *ADP-ribosylating Toxins and G Proteins: Insights into Signal Transduction* (Moss, J. and Vaughan, M., eds) pp. 493-510, American Society for Microbiology, Washington, D.C.). Mammalian cells contain mono-ADP-ribosyltransferases (ART) that catalyze the formation of ADP-ribose-(arginine) protein, which can be cleaved by a 39-kDa ADP-ribose-(arginine) protein hydrolase (ARH1) that releases free ADP-ribose and regenerates the unmodified protein.

In addition to mono-ADP-ribosyltransferases, mammalian cells contain enzymes that poly-ADP-ribosylate proteins. Poly-ADP-ribosylation is catalyzed by a family of enzymes termed poly(ADP-ribose) polymerases (PARP) (Ame et al. (2004) *Bioessays* 26:882-893), that synthesize polymers of ADP-ribose in carboxylate linkage (Ogata et al. (1980) *J. Biol. Chem.* 255:7610-7615; Ogata et al. (1980) *J. Biol. Chem.* 255:7616-7620), usually to PARP-1 (Ogata et al. (1981) *J. Biol. Chem.* 256:4135-4137). Multiple poly(ADP-ribose) polymerases (PARPs) have been identified in the human genome, but there is only one known poly(ADP-ribose) glycohydrolase (PARG) that degrades the (ADP-ribose) polymer to ADP-ribose. Poly-ADP-ribosylation is involved in a number of critical biological processes including DNA repair, carcinogenesis, and cellular differentiation (Diefenbach and Burkle (2005) *Cell Mol Life Sci.* 62:721-730; Masutani et al. (2005) *Cell Mol. Life. Sci.* 62:769-783; Nguewa et al. (2005) *Prog. Biophys. Mol Biol.* 88:143-172).

Sir2 (silent information regulator 2) family proteins are involved in gene silencing, life span extension, and chromosomal stability (Guarente (2000) *Genes Dev.* 14:1021-1026; Bitterman et al. (2003) *Microbiology and Molecular Biology Reviews* 67:376-399). In the presence of NAD, Sir2 couples protein deacetylation with formation of O-acetyl-ADP-ribose and release of nicotinamide (Imai et al. (2000) *Nature* 403:795-800; Jackson and Denu (2002) *J. Biol. Chem.* 21:18535-18544). In many biological systems, specific enzymes are believed to be involved in the degradation of small molecules that are generated in signaling cascades, and thus, in termination of their effects. Thus far, enzymatic destruction of O-acetyl-ADP-ribose has been shown only with the Nudix family (O'Handley et al. (1998) *J. Biol. Chem.* 273:3192-3197) of ADP-ribose pyrophosphatases (Rafty et al. (2002) *J. Biol. Chem.* 277:47114-47122) (nucleoside diphosphate linked to another moiety, hence the acronym Nudix) and perhaps other less selective pyrophosphatases.

Proteins capable of hydrolyzing other ADP-ribose linkages are important in the regulation of ADP-ribose metabolism, which is involved in many cellular processes including chromatin decondensation, DNA replication and repair, transcription, centrosome duplication, regulation of telomere function, mitosis, necrosis and caspase-dependent and -independent apoptosis (Bonicalzi et al. (2005) *Cell Mol. Life Sci.* 62:739-750; Virag and Szabo (2002) *Pharmacol. Rev.* 54:375-429). In addition, drugs targeting polymer synthesis and turnover can be used for treating disorders associated with excessive tissue damage or as anticancer agents, radiosensitizers and antiviral agents (Southan and Szabo (2003) *Curr Med Chem.* 10:321-40). Furthermore, proteins that specifically target signaling molecules in the Sir2 pathway could be used in regulating chromatin.

SUMMARY

The ARH3 protein has been discovered to have poly(ADP-ribose) glycohydrolase and O-acetyl-ADP-ribose hydrolase enzymatic activity. Methods are provided herein for catalyzing the release of ADP-ribose from poly(ADP-ribose) or O-acetyl-ADP-ribose utilizing an ARH3 polypeptide. Methods are also provided for producing polypeptides with poly (ADP-ribose) or O-acetyl-ADP-ribose hydrolase activity.

Methods are disclosed for altering a variety of biological activities affecting the release of ADP-ribose from poly (ADP-ribose) or O-acetyl-ADP-ribose hydrolase. For example, methods are disclosed for modifying DNA repair or chromatin structure in a mammalian cell. Methods are provided for treating cancer, or for treating a disorder in a subject associated with excessive DNA damage, or to affect aging and longevity. Methods are also provided for the treatment of inflammation, such as graft-versus-host disease, inflammatory arthropathy, allergy and atherosclerosis.

Methods are further provided for screening molecules for use in altering cellular differentiation, DNA repair, apoptosis, chromatin structure, or for use in the treatment of cancer or a disorder associated with excessive DNA damage. Methods are also provided for screening molecules capable of altering the hydrolysis activity of ARH3. The methods are useful in studying the regulation of ADP-ribose metabolism and for identifying new molecules useful in modifying various cellular processes, as well as for identifying agents of use in the treatment of disorders that may benefit from activation or inhibition of poly(ADP-ribosyl)ation or from modifying O-acetyl-ADP-ribose content.

The foregoing and other features and advantages will become more apparent from the following detailed description of several embodiments, which proceeds with reference to the accompanying figures.

DESCRIPTION OF FIGURES

FIG. 1A shows an alignment of the amino acid sequences of human ARH1 (NCBI/NIH Accession No. AAA35555) (SEQ ID NO: 7), human ARH2 (NCBI/NIH Accession No. CAC86114) (SEQ ID NO: 8), and human ARH3 (NCBI/NIH Accession No. CAC85940) (SEQ ID NO: 2). Amino acid acids critical for ARH1 activity are indicated by an asterisk (Konczalik and Moss (1999) *J. Biol. Chem.* 274:16736-16740).

FIG. 1B shows an alignment of the amino acid sequences of human ARH3 (SEQ ID NO: 2) and the catalytic domain of PARG (amino acids 421-976 of NCBI/NIH Accession No. AAT66422) (SEQ ID NO: 9). The amino acids mutated in a variant of ARH3 (D77N/D78N) are indicated by an asterisk.

The amino acids reported to be critical for activity based on mutagenesis of PARG are indicated by a plus sign (Patel et al. (2005) *Biochem. J.* 388:493-500). The amino acids mutated in a variant of ARH3 (E238Q/E239Q) (SEQ ID NO: 4) are indicated by a number sign. The amino acids mutated in a variant of ARH3 (E261Q/E262Q) (SEQ ID NO: 3) are indicated by a carat. Identical sequences are in white letters on black. Conserved amino acids (see Table 2, legend) are shaded gray.

Figure 2:
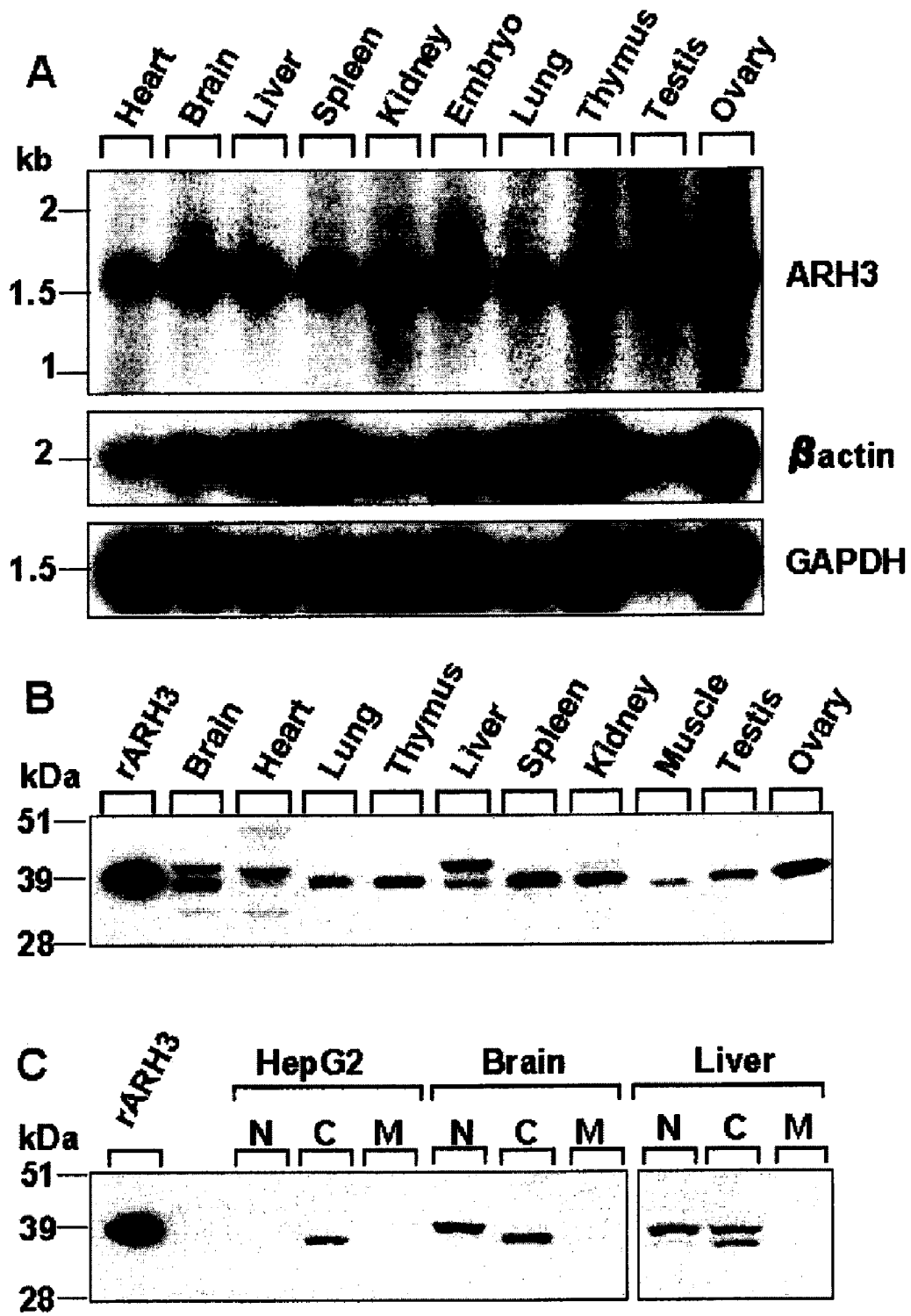

FIG. 2 shows detection of ARH3 mRNA and proteins in mouse tissues and HepG2 cells. FIG. 2A shows a Northern blot of mouse poly (A)+ RNA with an ARH3 cDNA probe. Positions of RNA standards are on the left. FIG. 2B is a digital image of a Western blot of the detection of ARH3 protein in the indicated tissues. FIG. 2C is a digital image of a Western blot of ARH3 protein detected in nuclear (HepG2, and mouse brain or liver tissue), cytosolic, and membrane fractions. N; nuclei, C; cytosol, M; membranes.

Figure 3:
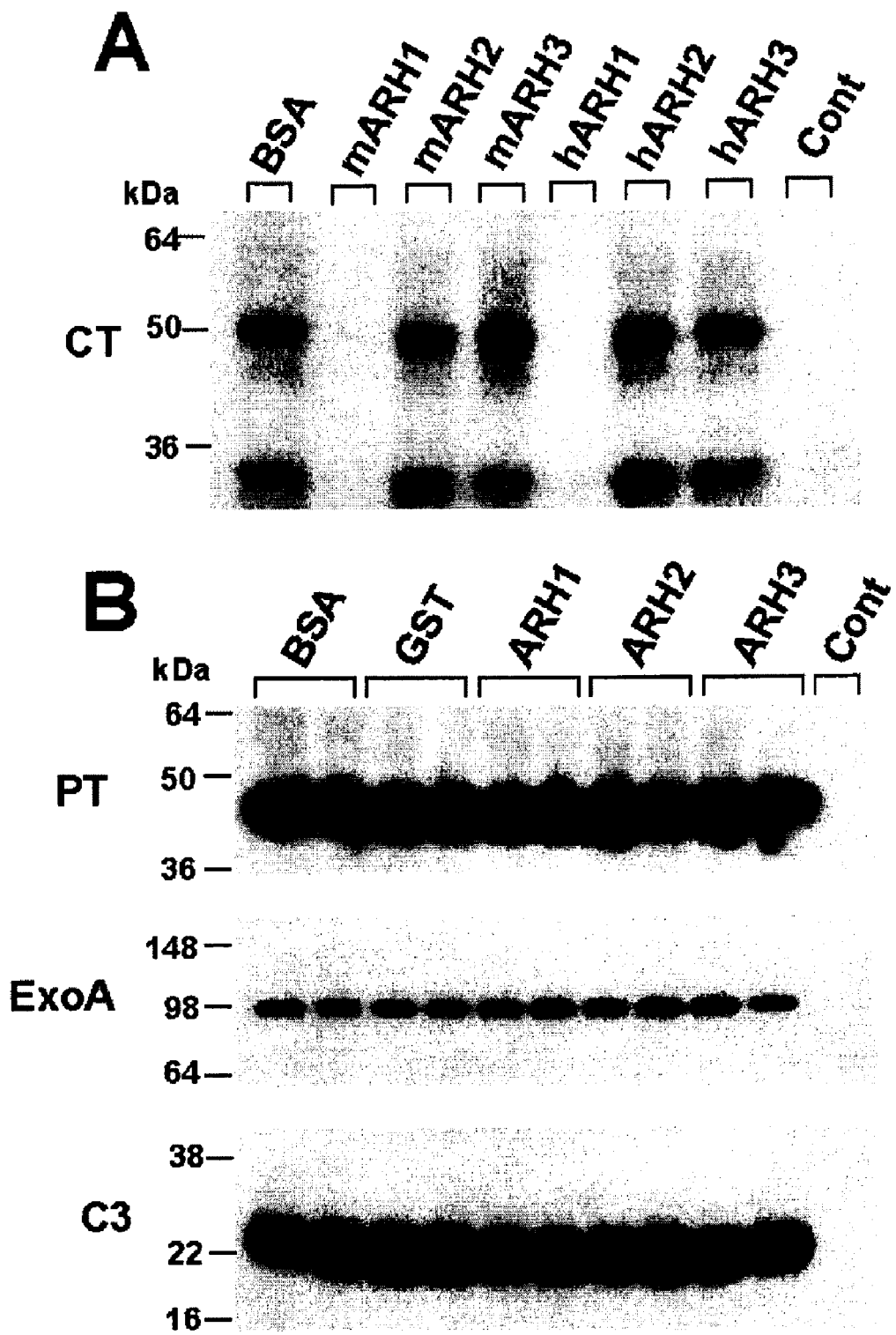

FIG. 3 shows the hydrolysis by ARH1, 2, or 3 of proteins that were mono-ADP-ribosylated by bacterial toxins. FIG. 3A is a digital image of an autoradiograph depicting samples from mouse brain membranes that were [$^{32}$P]ADP-ribosylated by incubation with cholera toxin and incubated with recombinant ARH 1, 2, or 3 or BSA. Cont: brain membranes that had been incubated with [$^{32}$P]-labeled NAD without CTA. FIG. 3B is a digital image of an autoradiograph depicting samples of [$^{32}$P] ADP-ribosylated Gαi/Gαo synthesized by pertussis toxin (PT), [$^{32}$P] ADP-ribosylated EF-2 in mouse brain cytosol synthesized by *Pseudomonas aeruginosa* exotoxin A (ExoA), or [$^{32}$P] ADP-ribosylated Rho in mouse brain cytosol synthesized by *Clostridium botulinum* C3 toxin. Cont: Substrate that had been incubated with [$^{32}$P]-labeled NAD without bacterial toxin.

Figure 4:
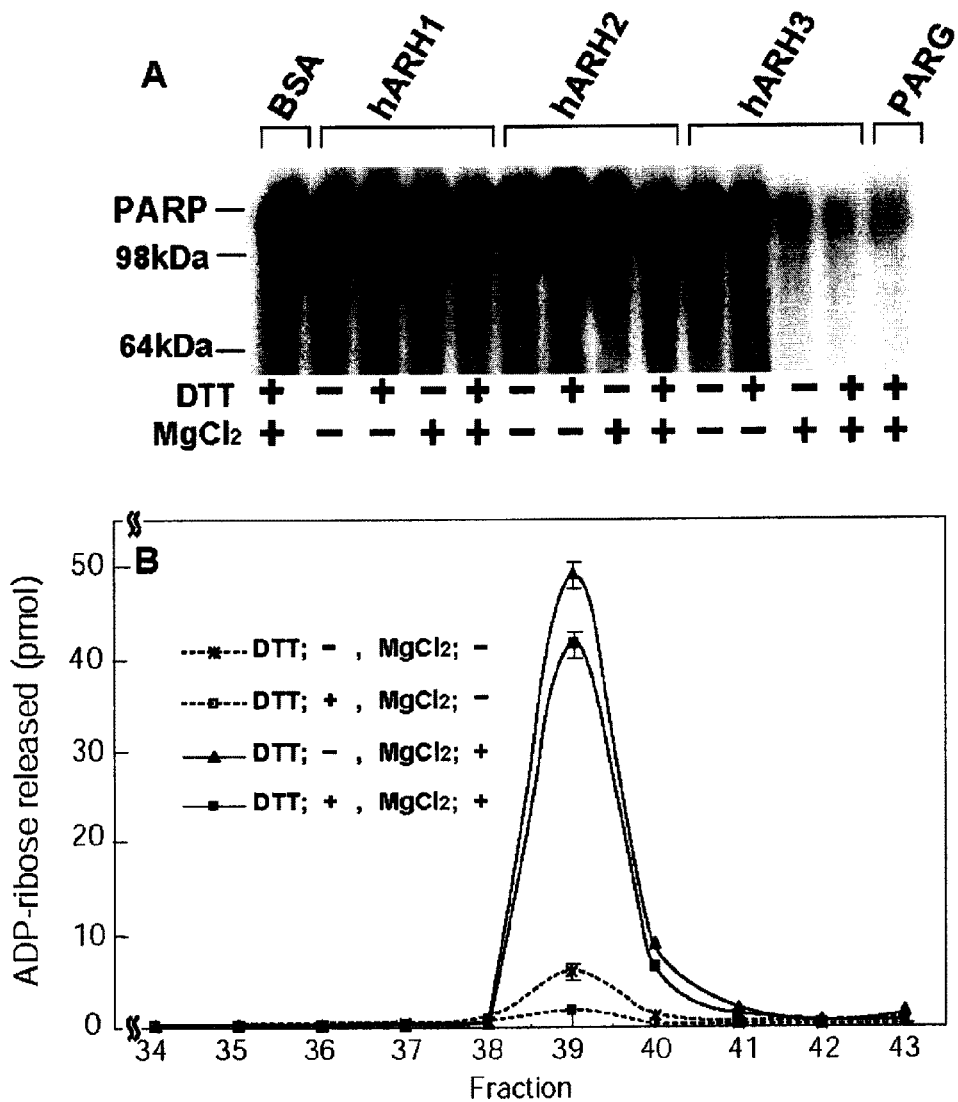

FIG. 4 shows the effects of DTT and $MgCl_2$ on poly(ADP-ribose) glycohydrolase activity of human ARH1, 2, and 3. FIG. 4A is a digital image of a Western blot of [$^{32}$P]poly (ADP-ribose)PARP degradation by human ARH1, 2, 3 and PARG in the presence or absence of DTT and/or $MgCl_2$. [$^{32}$P]poly(ADP-ribose)PARP is at the top of each lane. FIG. 4B shows a graph depicting the detection of [$^{14}$C]ADP-ribose by HPLC after [$^{14}$C]poly(ADP-ribose)PARP degradation by human ARH3 in the presence or absence of DTT and/or $MgCl_2$.

Figure 5:
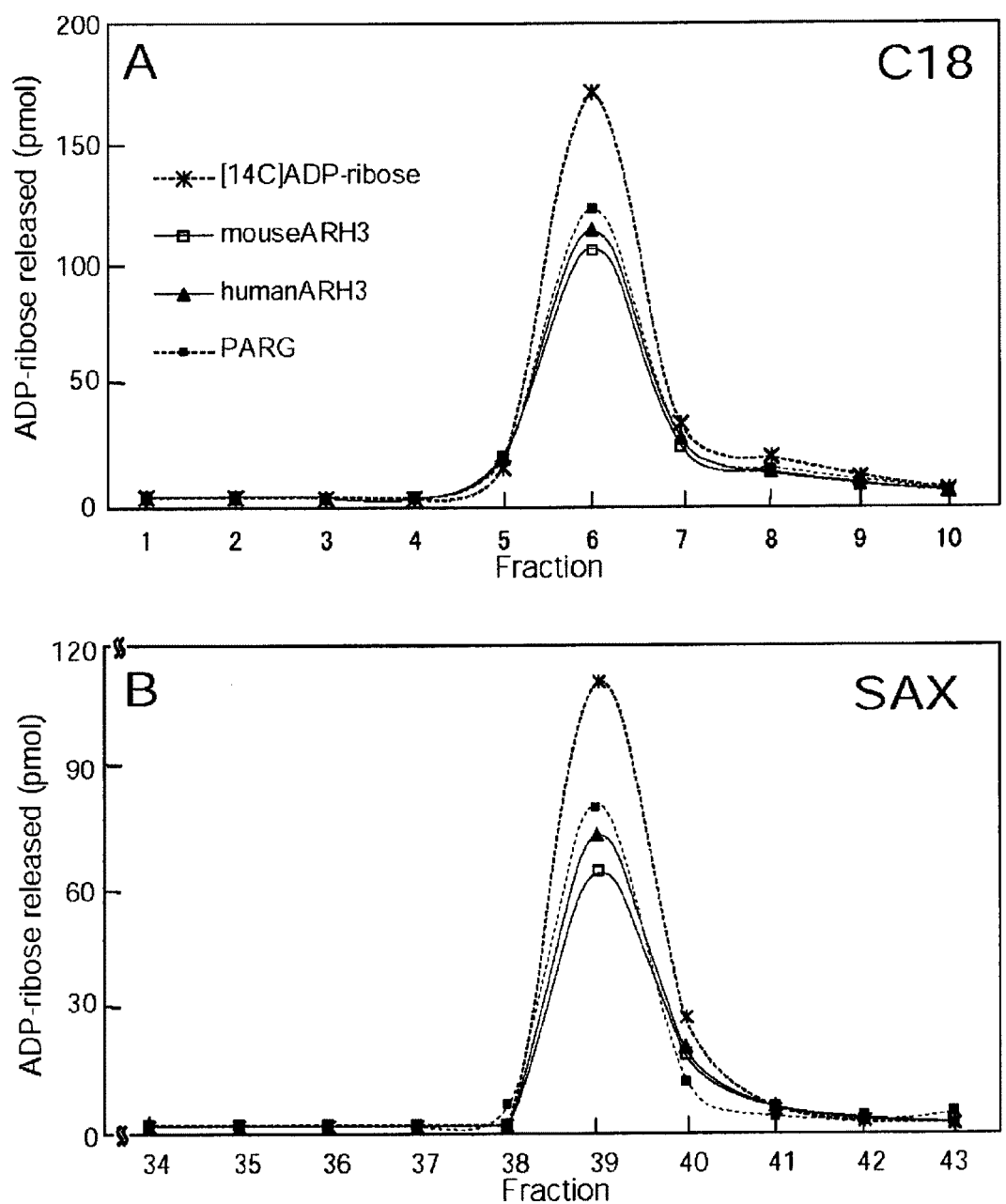

FIG. 5 shows HPLC analyses of [$^{14}$C]ADP-ribose released from ARH3- and PARG-catalyzed reactions. FIG. 5A shows a graph depicting products eluted from C18 HPLC and FIG. 5B shows a graph depicting products from a Zorbax SAX column.

Figure 6:
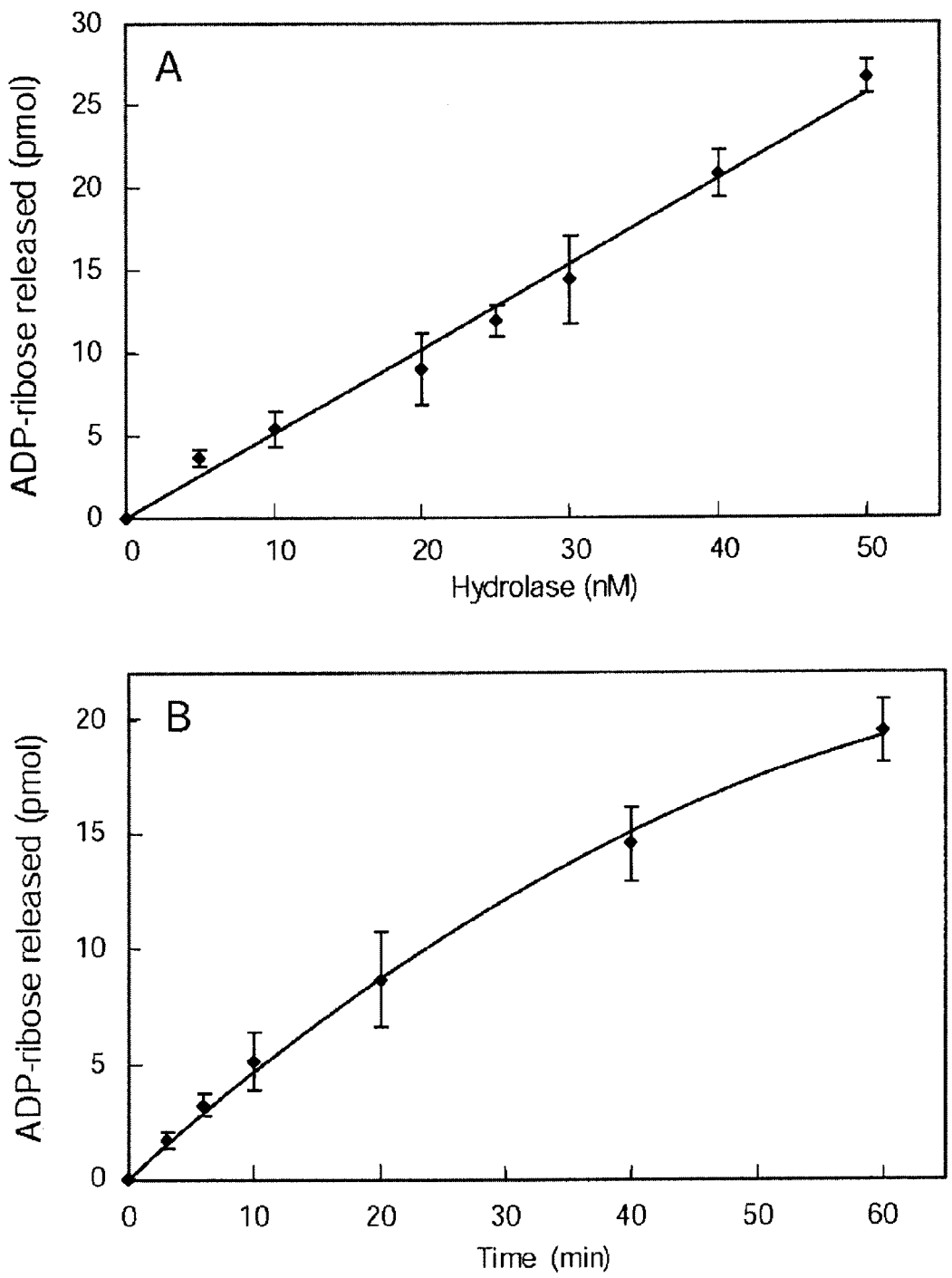

FIG. 6 shows graphs depicting the effect of hydrolase concentration (FIG. 6A) and time (FIG. 6B) on hydrolysis of poly(ADP-ribose) by human ARH3.

Figure 7:
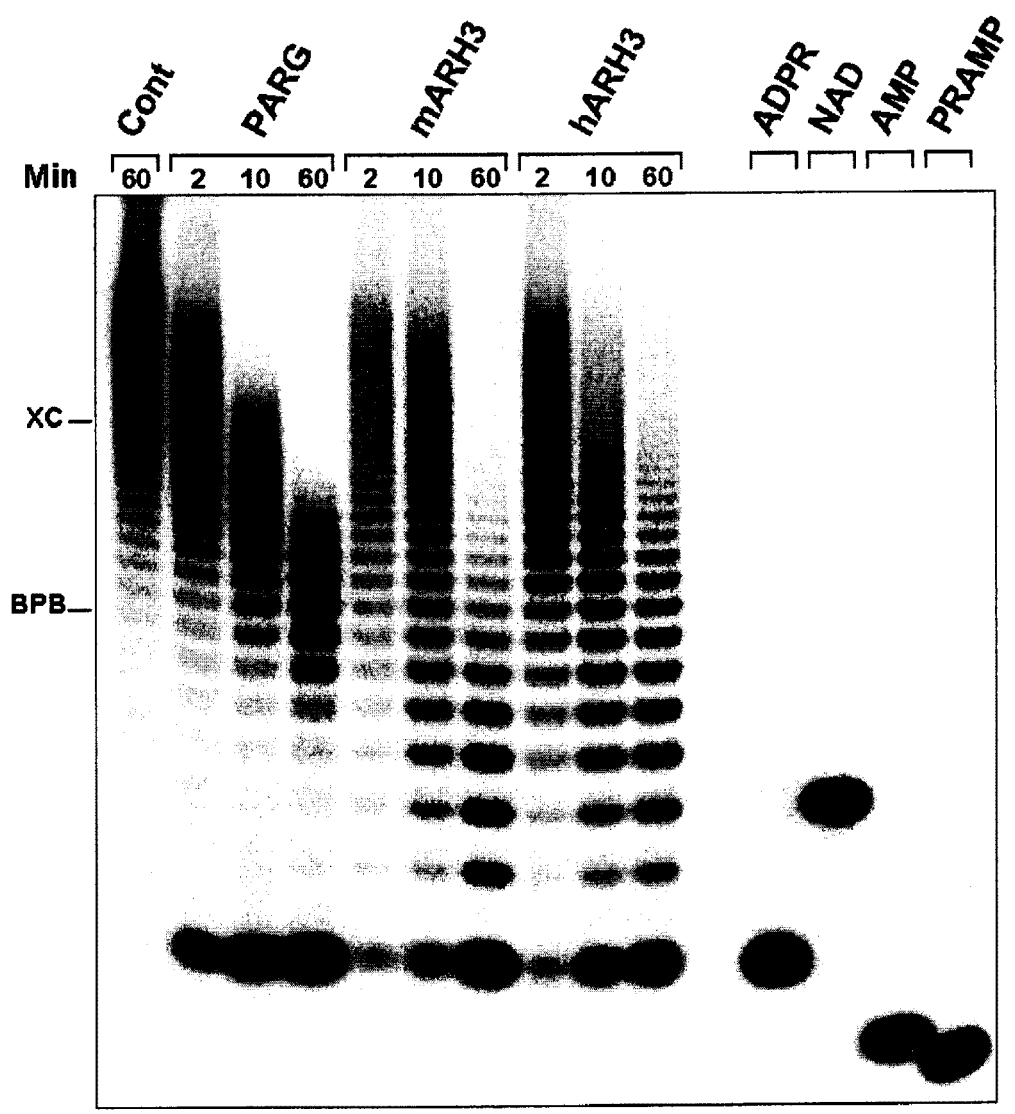

FIG. 7 is a digital image of an autoradiograph depicting the size of ADP-ribose polymers after incubation with mouse or human ARH3 or PARG from calf thymus. Cont, reaction without enzyme incubated for 60 min. On the right, [$^{32}$P]-labeled standards are ADPR (ADP-ribose), NAD (β-NAD, Perkin Elmer), AMP, PRAMP (phosphoribosyl-AMP). Bromophenol blue (BPB) and xylene cyanol (XC) co-migrated with (ADP-ribose)$_8$ and (ADP-ribose)$_{18}$, respectively.

Figure 8:
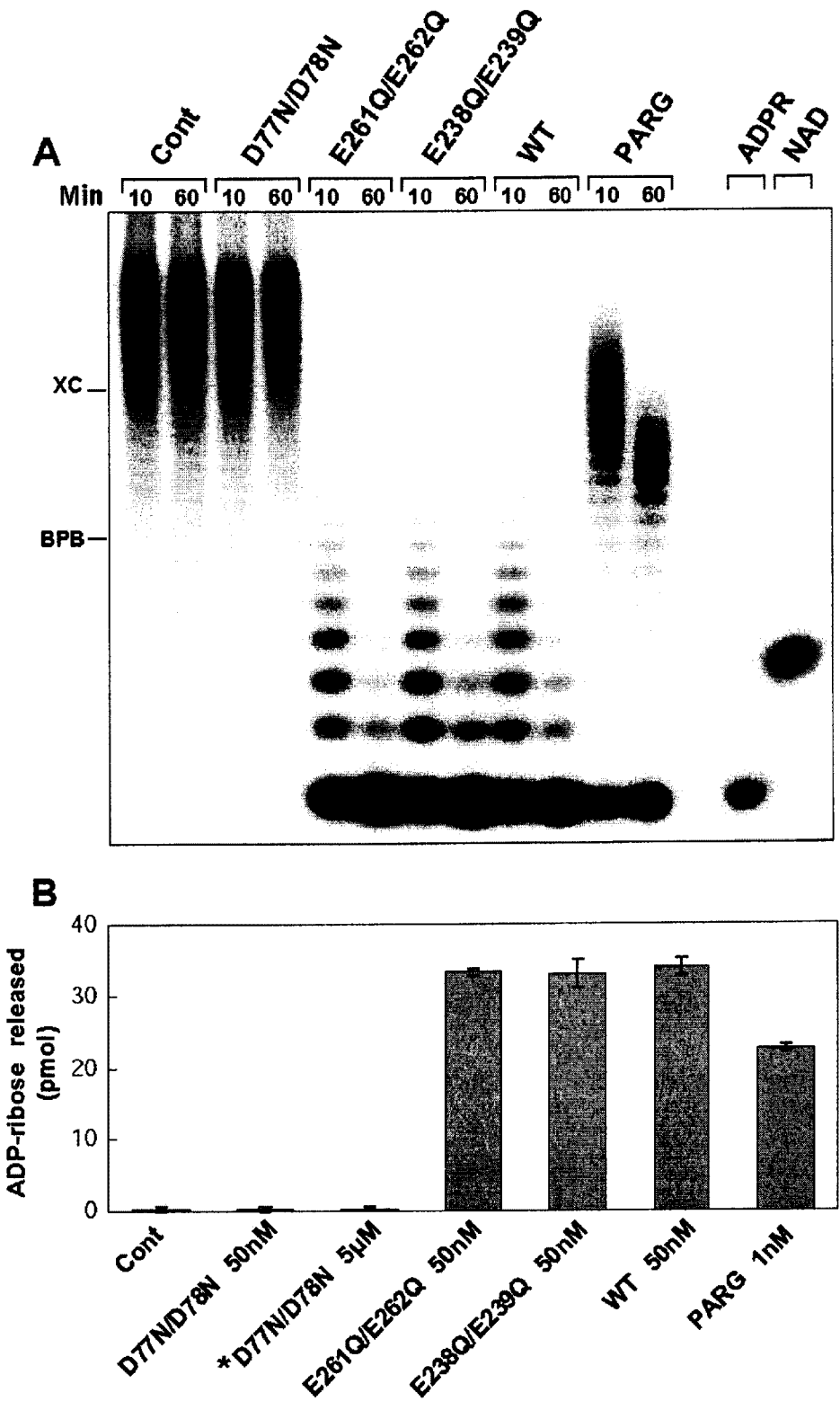

FIG. 8 shows the effect of mutation of human ARH3 on its hydrolysis of poly(ADP-ribose). FIG. 8A is a digital image of an autoradiograph showing detection of poly(ADP-ribose) hydrolysis products without enzyme (Cont) or with 1 μM ARH3 (wild-type or mutant) or 1.5 nM PARG. Positions of standards are indicated as in FIG. 7. FIG. 8B is a graph showing the amount of ADP-ribose released without enzyme (Cont) or with 50 nM human ARH3 (wild-type or mutant) or 1 nM PARG. *D77N/D78N 5 μM samples were incubated overnight with 5 μM mutant ARH3.

Figure 9:
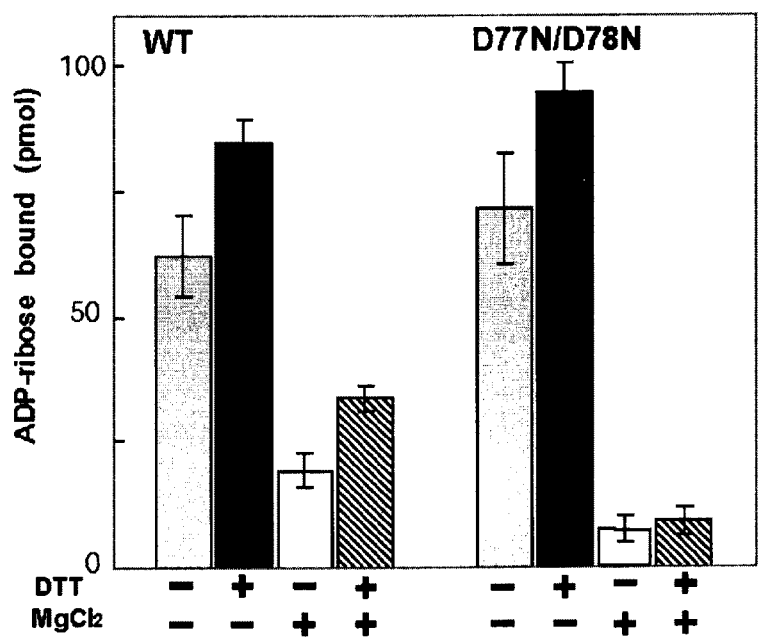

FIG. 9 shows a graph depicting [$^{14}$C]ADP-ribose binding by human ARH3 (WT or D77N/D78N mutant) in the presence or absence of DTT and/or $MgCl_2$.

Figure 10:
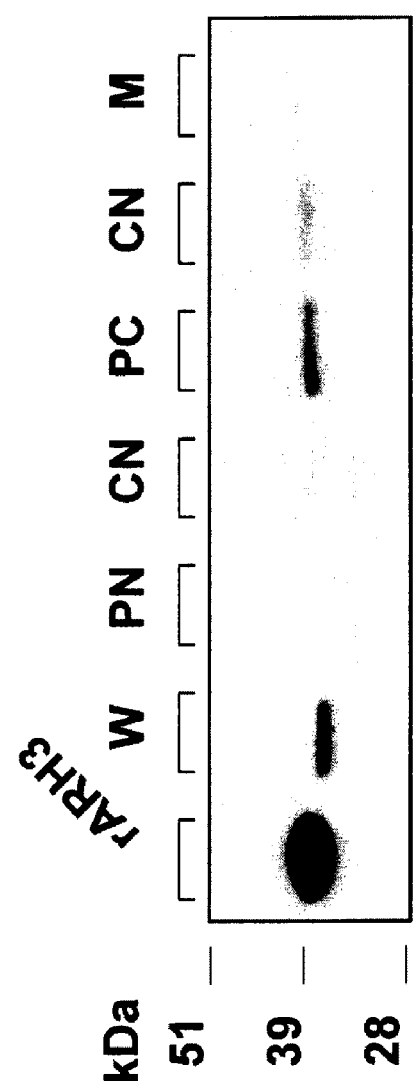

FIG. 10 is a digital image of an immunoblot showing the localization of ARH3 in HEK293T cells. Localization was investigated by cell fractionation, followed by immunoblotting. After cell fractionation, immunoreactive 39-kDa ARH3 was identified using antibodies against mouse ARH3 amino acids 355-370; the antibodies did not react with ARH1 and ARH2. ARH3 was present in both cytosol and membrane fractions.

Figure 11:
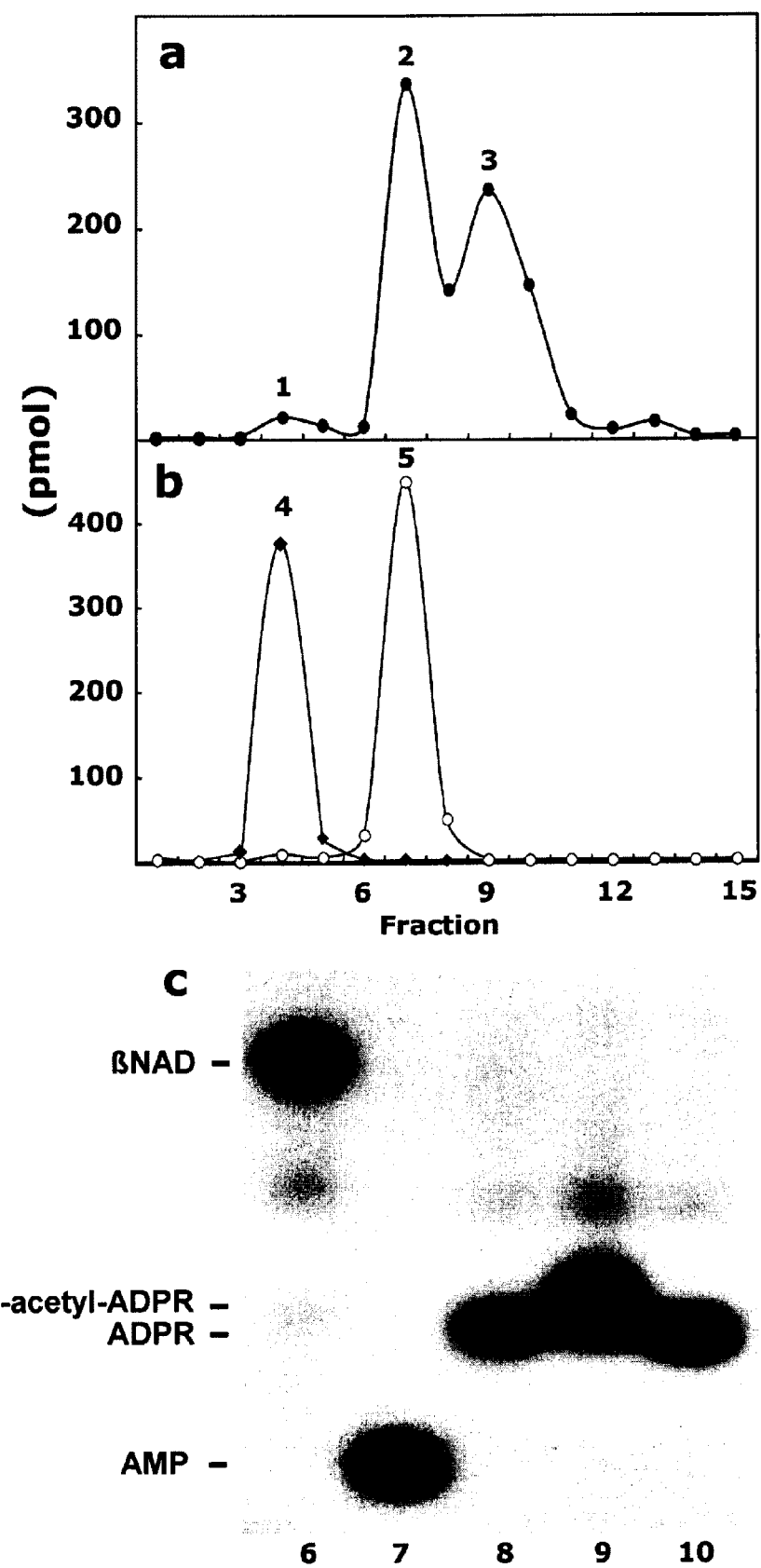

FIG. 11 shows the identification of products of Sir2 and ARH3-catalyzed reactions. FIG. 11A shows synthesis of O-acetyl-[$^{14}$C]ADP-ribose catalyzed by Sir2. FIG. 11B shows hydrolysis of O-acetyl-[$^{14}$C]ADP-ribose catalyzed by ARH3. Peaks: 1, ADP-ribose; 2, O-acetyl-[$^{32}$P]ADP-ribose; 3, β-NAD; 4, ADP-ribose; 5, O-acetyl-ADP-ribose. FIG. 11C is a digital image showing high resolution-polyacrylamide gel electrophoresis of substrates and products in reactions involving O-acetyl-[$^{32}$P]ADP-ribose. Lanes: 6) [$^{32}$P]β-NAD; 7) [$^{32}$P]AMP, produced by pyrophosphatase cleavage of [$^{32}$P]β-NAD; 8) [$^{32}$P]ADP-ribose produced from [$^{32}$P]β-NAD by CTA glycohydrolase activity; 9) O-acetyl-[$^{32}$P]ADP-ribose synthesized by Sir2 as in FIG. 11A; 10) [$^{32}$P]ADP-ribose produced by ARH3 from O-acetyl-[$^{32}$P]ADP-ribose as in FIG. 11B.

FIG. 12 shows hydrolysis of O-acetyl-ADP-ribose by ARH3. FIG. 12A is a graph of the results from incubation of 2.5 μM O-acetyl-[$^{14}$C]ADP-ribose and the indicated amount of mouse ARH3 for 1 hour. FIG. 12B is a graph of the results from incubation of 1.5 pmol of mouse ARH3 and 2.5 μM substrate at 30° C. for the indicated time.

FIG. 13 shows the hydrolysis of O-acetyl-ADP-ribose by wild type and mutant forms of ARH3 or PARG. FIG. 13A is a graph illustrating the results from incubation of 1.5 pmol of mouse ARH3 with or without 5 mM DTT and/or 10 mM $MgCl_2$ as described in FIG. 11B with incubation for 1 h at 30° C. FIG. 13B is a graph illustrating the results from incubation of 1.5 pmol of wild type or mutant human (D77-78) ARH3 or 20 mU of PARG for 2 h at 30° C. *D77,78, assays incubated with 15 pmol of mutant human ARH3 (D77, D78).

FIG. 14 shows the hydrolysis of O-acetyl-[$^{14}$C]ADP-ribose by ARH 1, 2 and 3. FIG. 14A is a graph of the results from incubation with the indicated amount of mouse ARH1, 2, or 3 for 2 h at 30° C. FIG. 14B is a graph of the results from incubation with 230 pmol of mouse ARH1 at 30° C. for the indicated time.

Figure 15:
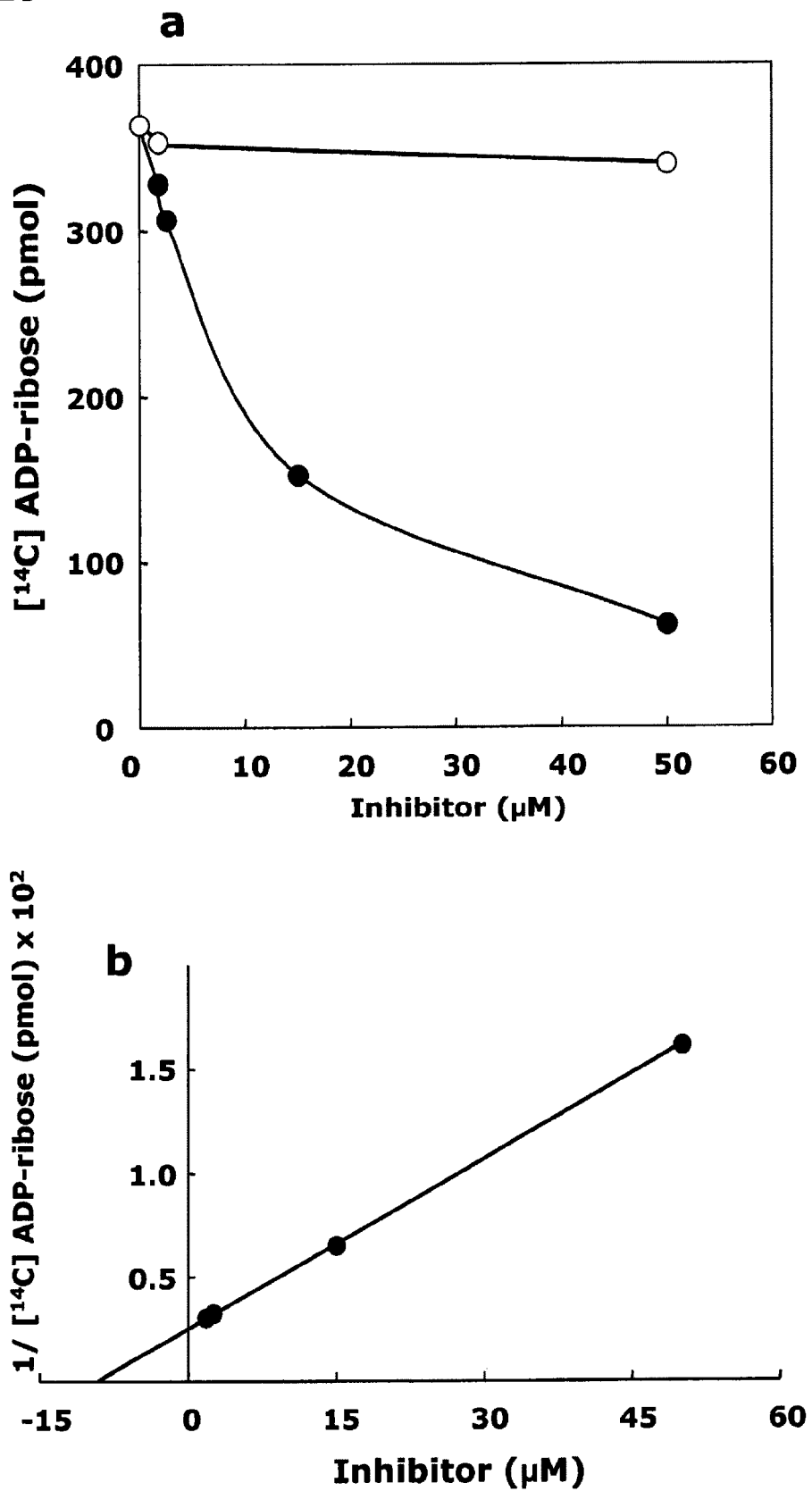

FIG. 15 shows inhibition of ARH3 hydrolysis by ADP-ribose and β-NAD. FIG. 15A is a graph of the results from an assay with 2 pmol of ARH3 and the indicated amount of ADP-ribose (●) or β-NAD (○) in 200 μl for 2 h at 30° C., as described in FIG. 11B. FIG. 15B is a graph of the inhibition of ARH3 hydrolysis by ADP-ribose data schematized for Lineweaver-Burk plot.

Figure 16:
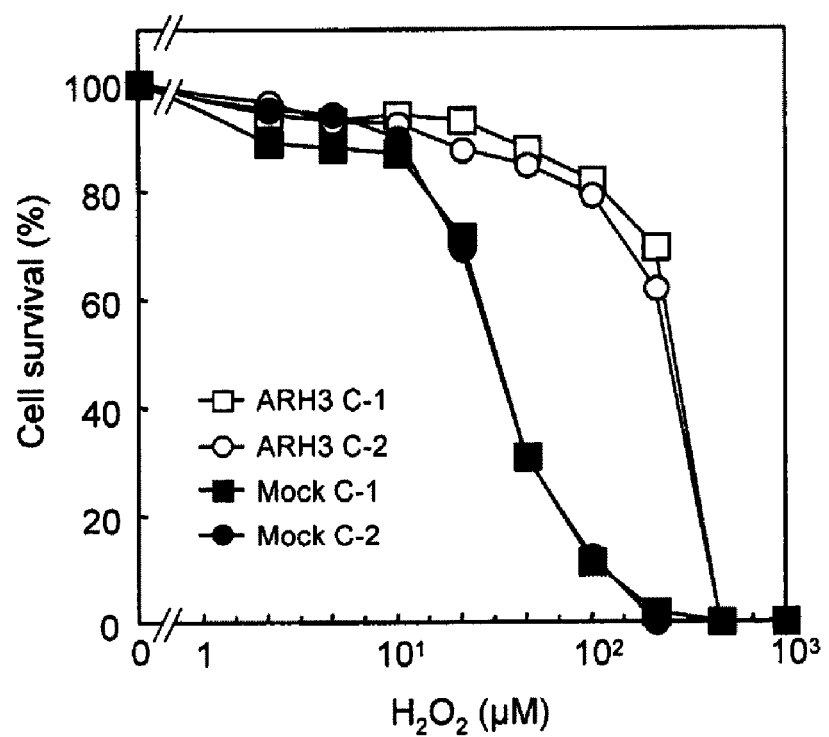

FIG. 16 is a line graph showing the effect of $H_2O_2$ on ARH3-transfected NIH3T3 cells. NIH3T3 cells were transfected with ARH3 cDNA using Lipofectamin transfection reagent (INVITROGEN™). After transfection, the cells were cultured and exposed to 200 μg/ml of Hygromycin G (INVITROGEN™) for 3-4 weeks to select stably transfected clones. Positive clones derived from single Hygromycin G-resistant cells were then isolated by cloning rings and further grown under the same conditions. As controls, NIH3T3 cells were transfected with an empty pcDNA3.1 vector (INVITROGEN™) and subjected to the same selection and cloning procedures as described above. The cells were plated in 96-well plates at 1×10⁴ cells/well, and incubated for 24 h at 37° C. in a humidified incubator. The cells were then challenged at the indicated concentrations of $H_2O_2$ for 24 hours. Cell survival was determined by using Cell-Counting Kit-8 (Dojindo). The experiments were repeated twice with similar results.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

DETAILED DESCRIPTION

I. Abbreviations
   AIDS acquired immune deficiency syndrome
   ADP adenosine diphosphate
   ADPR ADP-ribose
   AMP adenosine monophosphate
   ARH1 ADP-ribose-(arginine) hydrolase
   ARH3 ADP-ribosyl acceptor hydrolase
   ART ADP-ribosyltransferase
   ATP adenosine triphosphate
   BHA butyl hydroxy anisole
   BHT butyl hydroxy toluene
   bp base pair(s)
   BPB Bromophenol blue
   BSA bovine serum albumin
   CaMV cauliflower mosaic virus
   cDNA complementary DNA
   CTA cholera toxin A
   DEAE diethylaminoethyl
   DHBB Dihydroxyboronyl-Bio-Rex 70
   DMEM Dulbecco's Minimal Essential Medium
   DNA deoxyribonucleic acid
   DTT dithiothreitol
   EBV Epstein Barr virus
   EDTA ethylenediamine tetraacetic acid
   EEA Early endosomal antigen
   ExoA exotoxin A
   FBS fetal bovine serum
   GAPDH glyceraldehyde-3-phosphate dehydrogenase
   GST glutathione-S transferase
   HPLC high pressure liquid chromatography
   ip intraperitoneal
   iv intravenous
   kb kilobase pair(s)
   kDa kiloDalton
   LAMP Lysosomal-associated membrane protein
   mRNA messenger RNA
   NAD nicotinamide adenine dinucleotide
   NMDA N-methyl-D-aspartate
   NO nitric oxide
   pADPr poly(ADP-ribose) polymers
   PAGE polyacrylamide-gel electrophoresis
   PARG poly(ADP-ribose) glycohydrolase
   PARP poly(ADP-ribose) polymerase
   PBS phosphate buffered saline
   PCR polymerase chain reaction
   PRAMP phosphoribosyl-AMP
   PT pertussis toxin
   Rab Ras-like GTP-binding protein
   RNA ribonucleic acid
   RNase ribonuclease
   RP-HPLC reverse phase HPLC
   SDS sodium dodecyl sulfate
   SSC sodium citrate buffer
   SV40 simian virus 40
   TBE tris-borate EDTA
   TEMED tetramethylethylenediamine
   TKMS Tris-KCl—$MgCl_2$-Sucrose
   TMV tobacco mosaic virus
   WT wild type
   XC xylene cyanol II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

By "ADP-ribosylation activity" is intended the enzyme-catalyzed post-translational protein modification in which the ADP-ribose moiety is transferred from NAD+ to a specific amino acid in a target protein while the nicotinamide moiety is released.

By "agonist" is intended a molecule which, when bound to a protein, increases or prolongs the effect of the protein. Agonist may include proteins, nucleic acid molecules, carbohydrates, or any other molecules that bind to and modulate the effect of a protein.

By "ARH3" or "ARH3 protein" is intended a protein having both PARG activity and O-acetyl-ADP-ribose activity. By "an ARH3 hydrolysis activity" or "an ARH3 activity" is intended either PARG activity or O-acetyl-ADP-ribose activity. By "O-acetyl-ADP-ribose hydrolase activity" is intended the ability to generate ADP-ribose from O-acetyl-ADP-ribose. By "PARG activity" or "poly(ADP-ribose) glycohydrolase activity" is intended the ability to generate ADP-ribose from poly(ADP-ribose). Proteins with PARG activity have both exoglycosidase and endoglycosidase activity, and are therefore capable of hydrolyzing ribose-ribosyl glycosidic bonds between poly(ADP-ribose) polymer units located at the end and within the polymer. The protein PARG (an exemplary non-limiting protein sequence is set forth as Genbank Accession No. AAT66422, Jul. 5, 2004) is differentiated from an ARH3 protein in that it does not have O-acetyl-ADP-ribose hydrolysis activity. The terms "protein" and "polypeptide" are used interchangeably herein.

"Atherosclerosis" refers to the progressive narrowing and hardening of a blood vessel over time. Atherosclerosis is a common form of arteriosclerosis in which deposits of yellowish plaques (atheromas) containing cholesterol, lipoid material, and lipophages are formed within the intima and inner media of large and medium-sized arteries.

Treatment of atherosclerosis includes reversing or slowing the progression of atherosclerosis, for example as measured by the presence of atherosclerotic lesions and/or functional signs of the disease, such as improvement in cardiovascular function as measured by signs (such as peripheral capillary refill), symptoms (such as chest pain and intermittent claudication), or laboratory evidence (such as that obtained by EKG, angiography, or other imaging techniques). Inflammation plays a role in the development of atherosclerosis, for example by coupling dislipidemia to atheroma formation. Inflammatory pathways promoter early artherogenesis and thrombosis. Hence interfering with inflammation can inhibit the development and progression of atherosclerosis.

The term "cancer" is interpreted broadly. For example, the methods provided herein are useful for treating cancers and radiosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva, Wilm's tumor, and neoplastic disorders.

A neoplastic disorder is any new and abnormal growth; specifically, a new growth of tissue in which the growth is uncontrolled and progressive. Neoplastic disorders may include, but are not limited to, neoplastic disorders of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. Cancer includes a benign or malignant neoplasm, and thus includes adenocarcinoma, leukemia, lymphoma, melanoma, myeloma, sarcoma, teratocarcinoma, hyperplasia and hypertrophy. Malignant cancer is a subset of neoplastic disorders that show a greater degree of anaplasia and have the properties of invasion and metastasis.

By "chromatin structure" is intended the physical arrangement of chromatin in a cell. Chromatin is the substance of a chromosome and consists of a complex of DNA and protein in eukaryotic cells. The nucleic acids are generally in the form of double-stranded DNA. The major proteins involved in chromatin are histone proteins. In a eukaryotic cell, nearly all DNA is found compacted in chromatin. DNA is packaged into chromatin both to constrain the size of the molecule and to allow the cell to control expression of the chromatin packaged genes.

A "conservative amino acid substitution" is one in which the amino acid residue is replaced with an amino acid residue having a similar side chain. A "nonessential" amino acid residue is a residue that can be altered from the wild-type sequence of an ARH3 protein without altering the biological activity, whereas an "essential" amino acid residue is required for biological activity. Families of amino acid residues having similar side chains have been defined in the art. These families include amino acids with basic side chains (for example, lysine, arginine, histidine), acidic side chains (for example, aspartic acid, glutamic acid), uncharged polar side chains (for example, asparagine, glutamine, serine, threonine, tyrosine, cysteine), nonpolar side chains (for example, alanine, valine, leucine, isoleucine, proline, phenylalanine, methionine, tryptophan), beta-branched side chains (for example, threonine, valine, isoleucine) and aromatic side chains (for example, tyrosine, phenylalanine, tryptophan, histidine).

By "DNA repair" is intended the reconstruction of a continuous two-stranded DNA molecule without mismatch from a molecule that contained damaged regions. This damage may occur, for example, due to normal metabolic activities, such as DNA replication, or from environmental factors, such as chemical insults or UV rays. The major repair mechanisms are excision repair, in which defective regions in one strand are excised and resynthesized using the complementary base pairing information in the intact strand; photoreactivation repair, in which the lethal and mutagenic effects of ultraviolet light are eliminated; and post-replication repair, in which the primary lesions are not repaired, but the gaps in one daughter duplex are filled in by incorporation of portions of the other (undamaged) daughter duplex.

By "fragment" is intended a portion of a nucleotide sequence encoding a protein, or a portion of the amino acid sequence of the protein.

"Heterologous" generally refers to the nucleic acid sequences that are not endogenous to the cell or part of the native genome in which they are present, and have been added to the cell by infection, transfection, microinjection, electroporation, microprojection, or the like.

By "homologue" or "variant" is intended a nucleotide or amino acid sequence sufficiently identical to the reference nucleotide or amino acid sequence, respectively. "Homologues" or "variants" of an ARH3 polypeptide are encoded by a nucleotide sequence sufficiently identical to the nucleotide sequence of SEQ ID NO: 1 or 5. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity over its full length as compared to a reference sequence, for example using the NCBI Blast 2.0 gapped BLAST set to default parameters, or an equivalent program. By "equivalent program" is intended any sequence comparison program that, for any two sequences in question, generates an alignment having identical nucleotide or amino acid residue matches and an identical percent sequence identity when compared to the corresponding alignment generated by gapped BLAST. Alignment may also be performed manually by inspection. For comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologues and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologues could be obtained that fall outside of the ranges provided.

"Inflammation" is usually a part of the host defense response. When damage to tissue occurs, the body's response to the damage may result in inflammation. The damage may be due to trauma, lack of blood supply, hemorrhage, autoimmune attack, transplanted exogenous tissue or infection. This generalized response by the body includes the release of many components of the immune system (e.g., IL-1, TNF), attraction of cells to the site of the damage, swelling of tissue due to the release of fluid and other processes. Inflammation can be induced by pathogens that act on a cell of the innate immune systems or can be induced by cells of the adaptive immune system. Specific, non-limiting examples of agents that induce inflammation are cytokines, chemokines and pathogens.

Disease states that are associated with inflammation include, but may not be limited to, autoimmune diseases as defined above; atherosclerosis; chronic hepatitis, transplanted foreign tissues; drug or other hypersensitivity reaction. Conditions such as autoimmunity are characterized by the body's immune responses being directed against its own tissues and can cause prolonged inflammation.

"Inflammatory arthropathy" refers to an inflammatory disease affecting one or more joints, for example an inflammatory disease that affects the synovial membranes of one or more joints. Inflammatory arthropathies include, for example, arthritis, ankylosing spondylitis, Reiter's syndrome, psoriatic arthropathy, enteropathy spondylitis, juvenile arthropathy, and reactive arthropathy. Chronic inflammation is also believed to contribute to the aging of many tissues. Interfering with chronic inflammation can therefore slow physiological aging as compared to chronological aging.

By "introducing" is intended introduction into cells via conventional transformation or transfection techniques, or by phage-mediated infection, or, in the case of chemical compounds, by contacting the cell with the compound. As used herein, the terms "transformation," "transduction," "conjugation," and "protoplast fusion" are intended to refer to a variety of art-recognized techniques for introducing foreign nucleic acid (for example, DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other laboratory manuals.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (for example, sequences located at the 5' and 3' ends of the nucleic acid) in the genomic DNA of the organism from which the nucleic acid is derived. "Isolated," when used to refer to nucleic acid molecules, excludes isolated chromosomes. For example, in various embodiments, the isolated ARH3-encoding nucleic acid molecule can contain less than about 5 kb 4 kb, 3 kb, 2 kb, 1 kb, 0.5 kb, or 0.1 kb of nucleotide sequences that naturally flank the nucleic acid molecule in genomic DNA of the cell from which the nucleic acid is derived. An ARH3 protein that is substantially free of cellular material includes preparations of protein having less than about 30%, 20%, 10%, or 5% (by dry weight) of non-ARH3 protein (also referred to herein as a "contaminating protein").

By "modifies" or "modifying" is intended that an activity is altered in some manner.

By "mono-ADP-ribosyltransferase activity" is intended the transfer of a single ADP-ribose moiety onto a specific amino acid side chain of a target protein. Generally this amino acid is an arginine residue.

As used herein, the term "nucleic acid molecule" is intended to include DNA molecules (for example, cDNA or genomic DNA) and RNA molecules (for example, mRNA) and analogs of the DNA or RNA generated using nucleotide analogs. The nucleic acid molecule can be single-stranded or double-stranded, but preferably is double-stranded DNA. The terms "nucleic acid", "nucleotide" and "polynucleotide" are used interchangeably. By "complement" is intended a nucleotide sequence that is sufficiently complementary to a given nucleotide sequence such that it can hybridize to the given nucleotide sequence to thereby form a stable duplex. By "contiguous" nucleotides is intended nucleotide residues that are immediately adjacent to one another.

By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

By "PARP activity" or "(poly(ADP-ribose) polymerase) activity" is intended the ability to catalyze the elongation and branching of ADP-ribose units on ADP-ribosylated targets. PARP generally acts on glutamic acid residues of target proteins, but can also act on aspartic acid or lysine or on a mono-ADP ribosylated arginine.

"Promoter" refers to a nucleic acid sequence that functions to direct transcription of a downstream coding sequence. The promoter, together with other transcriptional and translational regulatory nucleic acid sequences (also termed "control sequences") are necessary for the expression of a DNA sequence of interest.

By "retains" activity is intended that a fragment or variant of a protein of interest will have at least about 30%, preferably at least about 50%, more preferably at least about 70%, even more preferably at least about 80% of the activity of the native protein. In the case of ARH3, this would be ARH3 hydrolysis activity.

By "stringent conditions" or "stringent hybridization conditions" is intended conditions under which a probe will hybridize to its target sequence to a detectably greater degree than to other sequences (for example, at least 2-fold over background).

"Subject" includes both human and animal subjects. An "animal" is a living multicellular vertebrate organism, a category that includes, for example, mammals and birds. A "mammal" includes both human and non-human mammals, such as dogs, cats, cows, horses, rabbits, monkeys, and humans.

By "transgenic cells" or "transformed cells" is intended cells that have incorporated or integrated exogenous nucleic acid sequences or DNA fragments. These nucleic acid sequences include those that are exogenous, or not present in the untransformed cell, as well as those that may be endogenous, or present in the untransformed cell.

By "transplantation" is intended the transfer of a tissue or an organ, or a portion thereof, from one body or part of the body to another body or part of the body. An "allogeneic transplantation" or a "heterologous transplantation" is transplantation from one individual to another, wherein the individuals have genes at one or more loci that are not identical in sequence in the two individuals. An allogeneic transplantation can occur between two individuals of the same species, who differ genetically, or between individuals of two different species. An "autologous transplantation" is a transplantation of a tissue or a portion thereof from one location to another in the same individual, or transplantation of a tissue or a portion thereof from one individual to another, wherein the two individuals are genetically identical. The tissue to be transplanted may be cells that were isolated from an individual and subjected to treatments in vitro before being transferred back into the same or another body.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease or disorder in a susceptible subject, a reduction in severity of some or all clinical symptoms of the disease or disorder, a slower progression of the disease or disorder, a reduction in the number of relapses of the disease or disorder, an improvement in the overall health or well-being of the subject, or by other parameters well known in the art that are specific to the particular disease or disorder.

By "vector" is intended a nucleic acid construct designed for transfer between different host cells. By "expression vector" is intended a vector that has the ability to incorporate, integrate and express heterologous DNA sequences or fragments in a foreign cell. Typically these contain a promoter and a coding sequence. Often, such constructs will also contain a 3' untranslated region. Such constructs may contain a 'signal sequence' or 'leader sequence' to facilitate co-translational or post-translational transport of the peptide to certain intracellular structures such as the endoplasmic reticulum or Golgi apparatus. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids, mitochondria, and the like. By "transformation vector" is intended a DNA molecule that is necessary for efficient transformation of a cell. Such a molecule may consist of one or more expression cassettes, and may be organized into more than one vector DNA molecule. In some instances, the expression vector may include a nucleotide sequence that itself, or by encoding a protein, affects expression of a protein or a nucleotide sequence. These sequences may include, for example, siRNA, complementary DNA, a protein that stabilizes mRNA, and the like.

The above term descriptions are provided solely to aid the reader, and should not be construed to have a scope less than that understood by a person of ordinary skill in the art or as limiting the scope of the appended claims.

Unless otherwise explained, all technical and scientific terms used herein have the same meaning as commonly understood by one of ordinary skill in the art to which this disclosure belongs. The singular terms "a," "an," and "the" include plural references unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

ARH3 and Its Activity

Human ARH3 is a 39-kDa protein that was initially identified by sequence similarity as an ADP-ribosyl-acceptor-hydrolase. For exemplary amino acid sequences, see Genbank Accession Nos. AJ313333 (Jun. 21, 2002) and CAC85940 (Jun. 21, 2002), both herein incorporated by reference in their entirety. Human ARH3 shares amino acid sequence identity with both human ARH1 and the catalytic domain of poly(ADP-ribose) glycohydrolase (PARG) (see, for example, Genbank Accession No. AAT66422, Jul. 5, 2004). Amino acid sequences of exemplary human ARH1, 2, and 3, and the catalytic domain of PARG are aligned for comparison in FIG. 1. Amino acid sequences of human ARH1 and ARH2 are about 45% identical but only about 20% identical to that of ARH3 (see Examples, see Table 2).

Generally, ARH3 is more identical to the catalytic region of the PARG than to ARH1 or ARH2. In one example human ARH3 is about 20% identical to human PARG catalytic domain (111 kDa form).

It has surprisingly been found that ARH3 exhibits poly (ADP-ribose) glycohydrolase (PARG) activity, generating ADP-ribose from poly(ADP-ribose), and that it is capable of acting on O-acetyl-ADP-ribose to generate ADP-ribose. However, while ARH3 is capable of binding to ADP-ribose, ARH3 does not hydrolyze ADP-ribosylarginine. It also does not hydrolyze ADP-ribosyl-asparagine, -diphthamide or -cysteine. ARH3 PARG activity, like the activity of ARH1, is enhanced by magnesium ($Mg^{2+}$). Thus, this protein can be used to regulate poly(ADP-ribose) levels in a cell ARH3 proteins include, but are not limited to, those set forth in SEQ ID NOS:2 and 6, which are encoded by the nucleotide sequences set forth in SEQ ID NO: 1 and 5, respectively. In several examples, an ARH3 protein is at least about 85%, at least about 90%, at least about 95%, at least about 98%, at least about 99% identical to SEQ ID NO: 2 or SEQ ID NO: 6, and cleaves O-acetyl-ADP-ribose to generate ADP-ribose and can produce ADP-ribose from poly(ADP-ribose). Similarly, a nucleic acid encoding an ARH3 protein can be at least about 85%, at least about 90%, at least about 95%, at least about 98%, at least about 99% identical to SEQ ID NO: 1 or SEQ ID NO: 5, and encode a polypeptide that cleaves O-acetyl-ADP-ribose to generate ADP-ribose and can produce ADP-ribose from poly(ADP-ribose). Examples of specific variants that may be used are set forth as SEQ ID NOS: 3 and 4. Fragments or variants of the amino acid sequence of ARH3 can be used in the methods provided herein.

The ARH1, ARH3, and PARG catalytic domains all contain pairs of vicinal acidic amino acids, aspartate or glutamate (Konczalik and Moss (1999) *J. Biol. Chem.* 274:16736-16740; Patel et al. (2005) *Biochem. J.* 388:493-500). Critical vicinal acidic amino acids in ARH3, identified by mutagenesis (D77, D78), are located in a region similar to that required for activity in ARH1, but different from the location of the critical vicinal glutamates in the PARG catalytic site. In one example, variants of ARH3 proteins will not have mutations at these two residues critical for activity.

In several non-limiting examples, an ARH3 polypeptide, or variant or fragment thereof, can be a polypeptide having the amino acid sequence set forth as SEQ ID NO: 2, 3, 4, or 6; a polypeptide having an amino acid sequence at least about 90%, 95%, 98% or 99% identical to the amino acid sequence set forth as SEQ ID NO: 2, 3, 4, or 6; or a polypeptide that is encoded by a nucleic acid molecule having a nucleotide sequence at least about 90%, 95%, 98% or 99% identical to the nucleotide sequence set forth as SEQ ID NO: 1 or 5. It should be noted that fusion polypeptides can be utilized, such as polypeptides including six histidine residues or covalently linked to a carrier, such as beta-galactosidase.

An exemplary human ARH3-encoding nucleotide sequence (SEQ ID NO: 1) is set forth below:

```
atggc cgcagcggcg atggcggcag cggcaggtgg aggggctggc gcggcccgct ccctctcgcg cttccgaggc tgcctggctg gcgcgctgct cggggactgc gtgggctcct tctacgaggc ccacgacacc gtcgacctga cgtcagtcct gcgtcatgtc cagagtctgg agccggaccc cggcacgccc gggagtgagc ggacagaagc cttgtactac acagatgaca cagccatggc cagggccctg gtgcagtccc tgctagccaa ggaggcctttt gacgaggtgg acatggctca cagatttgct caggagtaca agaaagaccc tgacagggc tatggtgctg gagtagtcac tgtcttcaag aagctcctga accccaaatg tcgcgatgtc tttgagcctg cccgggccca gtttaacggg aaaggctcct atggcaatgg aggtgccatg cgggtggctg gcatctccct ggcctatagc agtgtccagg atgtgcagaa gtttgcccgg ctctcggccc agctgacaca cgcctcctcc ctgggttaca atggcgccat cctgcaggcc ctggctgtgc acctggcctt gcagggcgag tcttccagcg agcactttct caagcaactc ctgggccaca tggaggatct ggagggtgat gcccagtccg tcttggatgc cagggagttg ggcatggagg agcgtccata ctccagccgc ctgaagaaga ttggagagct tctagaccag gcatcggtga ccagggagga agtggtgtct gagctaggga atggcattgc tgcctttgag tcggtaccca ccgccatcta ctgcttccta cgctgcatgg agccagaccc tgagatccct tctgccttca atagcctcca aaggactctc atttattcca tctcacttgg tggggacaca gacaccattg ccaccatggc tggggccatt gctggtgcct actatgggat ggatcaggtg ccagagagct ggcagcaaag ctgtgaaggc tacgaggaga
```

-continued

```
cagacatcct ggcccaaagc ctgcaccgtg tcttccagaa gagttga
```

An exemplary sequence human ARH3 amino acid sequence (SEQ ID NO: 2), encoded by SEQ ID NO: 1, is set forth below:

```
MAAAAMAAAAGGGAGAARSLSRFRGCLAGALLGDCVGSFYEAHDTVDLTS

VLRHVQSLEPDPGTPGSERTEALYYTDDTAMARALVQSLLAKEAFDEVDM

AHRFAQEYKKDPDRGYGAGVVTVFKKLLNPKCRDVFEPARAQFNGKGSYG

NGGAMRVAGISLAYSSVQDVQKFARLSAQLTHASSLGYNGAILQALAVHL

ALQGESSSEHFLKQLLGHMEDLEGDAQSVLDARELGMEERPYSSRLKKIG

ELLDQASVTREEVVSELGNGIAAFESVPTAIYCFLRCMEPDPEIPSAFNS

LQRTLIYSISLGGDTDTIATMAGAIAGAYYGMDQVPESWQQSCEGYEETD

ILAQSLHRVFQKS.
```

An exemplary murine ARH3-encoding nucleotide sequence (SEQ ID NO: 5) is set forth below:

```
ATGGCGG TGGCTGCGGC GGCAGCAGCT

ACAGCGATGT CGGCGGCGGG GGGCGGCGGG GCAAGTGCGG

CCCGCTCCAT CTCGCGCTTC CGAGGTTGCC TGGCGGGCGC

GCTGCTGGGA GATTGCGTGG GCGCTGTCTA CGAGGCACAC

GATACCGTCA GCCTGGCATC AGTCCTGAGT CACGTCGAGA

GCCTGGAGCC GGACCCGGGC ACGCCGGGCA GCGCGCGGAC

AGAGACACTG TACTACACAG ATGACACTGC CATGACCAGG

GCCCTGGTAC AGTCCCTGCT GGCCAAGGAG GCCTTCGACG

AGGTGGACAT GGCTCACAGG TTTGCCCAGG AATACAAGAA

GGACCCTGAC AGAGGGTATG GGGCCGGAGT CATCACTGTC

TTCAAGAAAC TCCTGAATCC CAAGTGCCGT GATGTCTATG

AGCCTGCCCG GGCCCAGTTC AACGGGAAGG GTTCCTATGG

CAATGGGGGT GCCATGCGGG TAGCAGGCAT CTCGCTGGCC

TATAGCAGTG TCCAAGATGT ACAGAAGTTT GCCCGGCTCT

CAGCCCAGCT GACCCACGCC TCTTCCCTGG GCTATAACGG

TGCCATCTTG CAGGCCCTGG CTGTGCACCT TGCTCTGCAG

GGTGTATCAT CCAGTGAGCA CTTCCTCGAG CAGCTTCTGG

GCCACATGGA GGAGCTGGAA GGTGATGCCC AGTCAGTCTT

GGACGCCAAG GAGTTGGGTA TGGAGGAGCG TCCGTACTCC

AGCAGGCTGA AGAAGGTCGG AGAGCTGCTG GACCAGGACG

TGGTGAGCCG AGAGGAAGTG GTGTCCGAGC TAGGGAATGG

CATTGCCGCC TTTGAATCTG TGCCCACCGC CATCTACTGC

TTCCTGCGCT GCATGGAGCC TCACCCTGAG ATCCCCTCCA

CCTTCAACAG TCTCCAGAGG ACTCTCATCT ACTCCATCTC

ACTTGGTGGG GACACAGACA CCATAGCCAC CATGGCTGGG
```

```
                           -continued
GCCATTGCTG  GAGCTTACTA  TGGGATGGAA  CAGGTGCCGG

AGAGCTGGCA  GCAAAGTTGT  GAAGGCTTTG  AGGAGACAGA

CGTCCTGGCC  CAGAGCCTGC  ACCGAGTCTT  CCAGGAGAGC  TCGTAA
```

An exemplary murine ARH3 amino acid sequence (SEQ ID NO: 6), encoded by SEQ ID NO: 5 is as follows:

```
MAVAAAAAATAMSAAGGGGASAARSISRFRGCLAGALLGDCVGAVYEAHD

TVSLASVLSHVESLEPDPGTPGSARTETLYYTDDTAMTRALVQSLLAKEA

FDEVDMAHRFAQEYKKDPDRGYGAGVITVFKKLLNPKCRDVYEPARAQFN

GKGSYGNGGAMRVAGISLAYSSVQDVQKFARLSAQLTHASSLGYNGAILQ

ALAVHLALQGVSSSEHFLEQLLGHMEELEGDAQSVLDAKELGMEERPYSS

RLKKVGELLDQDVVSREEVVSELGNGIAAFESVPTAIYCFLRCMEPHPEI

PSTFNSLQRTLIYSISLGGDTDTIATMAGAIAGAYYGMEQVPESWQQSCE

GFEETDVLAQSLHRVFQESS
```

Fragments and variants of the ARH3 amino acid sequence for use in the methods provided herein are biologically active, that is they continue to possess the desired biological activity of the native protein, that is, retain the ARH3 hydrolysis activity. Methods for measuring the hydrolysis of poly(ADP-ribose) or O-acetyl-ADP-ribose are well known in the art. See, the Examples section as well as U.S. Pat. Nos. 6,337,202, and 6,887,675, herein incorporated by reference in their entirety.

To determine the percent identity of two amino acid sequences, the sequences are aligned for optimal comparison purposes. The percent identity between the two sequences is a function of the number of identical positions shared by the sequences (percent identity=number of identical positions/total number of positions×100). In one embodiment, the two sequences are the same length. The percent identity between two sequences can be determined using techniques similar to those described below, with or without allowing gaps. In calculating percent identity, typically exact matches are counted.

Methods of alignment of sequences for comparison are well known in the art. Various programs and alignment algorithms are described in: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237; Higgins and Sharp (1989) *CABIOS* 5:151; Corpet et al. (1988) *Nucleic Acids Research* 16:10881; and Pearson and Lipman (1988) *Proc. Natl. Acad. Sci. U.S.A.* 85:2444. Altschul et al. (1994) *Nature Genet.* 6:119 presents a detailed consideration of sequence alignment methods and homology calculations.

The NCBI Basic Local Alignment Search Tool (BLAST) (Altschul et al. (1990) *J. Mol. Biol.* 215:403) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet. Alternatively, alterations may be made to the protein sequence of many proteins at the amino or carboxy terminus without substantially affecting activity.

The protein sequences added can include entire protein-coding sequences, such as those used commonly in the art to generate protein fusions. Such fusion proteins are often used to: (1) increase expression of a protein of interest; (2) introduce a binding domain, enzymatic activity, or epitope to facilitate either protein purification, protein detection, or other experimental uses known in the art; (3) target secretion or translation of a protein to a subcellular organelle, such as the periplasmic space of Gram-negative bacteria, or the endoplasmic reticulum of eukaryotic cells, the latter of which often results in glycosylation of the protein.

For example, conservative amino acid substitutions may be made at one or more predicted, preferably nonessential amino acid residues. Amino acid substitutions may be made in non-conserved regions that retain function. In general, such substitutions would not be made for conserved amino acid residues, or for amino acid residues residing within a conserved motif, where such residues are essential for protein activity. One of skill in the art would understand that functional variants may have minor conserved or nonconserved alterations in the conserved residues. Any nucleotide sequence variant can include, for example, no more than twenty, no more than ten, no more than five, nor more than three, no more than two, or a single amino acid substitutions into the encoded polypeptide.

The methods disclosed herein can also use nucleic acids encoding an ARH3, or a fragment thereof. A fragment of a nucleotide sequence useful in the methods provided herein encodes a biologically active portion of an ARH3 protein. Nucleic acid molecules that are fragments of an ARH3 nucleotide sequence have at least about 50, 100, 200, 300, 400, 500, 600, 700, 800, 900, 1000, 1200, 1400, 1600, 1800, 2000, 2500, 3000, 3500, 4000, 4200, 4400, 4600, 4800, 5000 contiguous nucleotides, or up to the number of nucleotides present in a full-length ARH3-encoding nucleotide sequence disclosed herein (for example, 1092 nucleotides for SEQ ID NO: 1), depending upon the intended use. A fragment of an ARH3-encoding nucleotide sequence that encodes a biologically active portion of a protein will encode at least about 15, 25, 30, 50, 75, 100, 125, 150, 175, 200, 250, 300, or 350 contiguous amino acids, or up to the total number of amino acids present in a full-length ARH3 protein (for example, 363 amino acids for SEQ ID NO: 2).

Nucleic acids encoding an ARH3 that are at least about 90%, 95%, 98% or 99% identical to SEQ ID NO: 1 or SEQ ID NO: 5 can also be utilized in the methods disclosed herein. Computer programs for determining sequence identity are disclosed above. Variants of the ARH3-encoding nucleotide sequences include those sequences that encode the ARH3 proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the ARH3 proteins disclosed herein as discussed below. Variants also include a nucleic acid molecule that hybridizes to the nucleic acid molecule of SEQ ID NO: 1 or 5, or a complement thereof, under stringent conditions that encodes an ARH3.

One of skill in the art can readily introduce changes by mutation into the ARH3 nucleotide sequences, thereby leading to changes in the amino acid sequence of the encoded ARH3 proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis, including PCR amplifications that alter or extend the protein coding sequence by virtue of inclusion of amino acid encoding sequences in the oligonucleotides utilized in the PCR amplification. Such variant nucleotide sequences may also be used in the methods provided herein.

Variant nucleotide sequences can be made by introducing mutations randomly along all or part of the coding sequence, such as by saturation mutagenesis, and the resultant mutants can be screened for ability to confer ARH3 hydrolysis activity to identify mutants that retain activity. Following mutagenesis, the encoded protein can be expressed recombinantly, and the activity of the protein can be determined using standard assay techniques.

Variant nucleotide and amino acid sequences for use in the methods provided herein also encompass sequences derived from mutagenic and recombinogenic procedures such as DNA shuffling. With such a procedure, one or more different ARH3 protein coding regions can be used to create a new ARH3 protein possessing the desired properties. In this manner, libraries of recombinant polynucleotides are generated from a population of related sequence polynucleotides having sequence regions that have substantial sequence identity and can be homologously recombined in vitro or in vivo. For example, using this approach, sequence motifs encoding a domain of interest may be shuffled between an ARH3 gene disclosed herein and other known ARH3 genes to obtain a new gene coding for a protein with an improved property of interest, such as an increased ARH3 hydrolysis activity. Strategies for such DNA shuffling are known in the art. See, for example, Stemmer (1994) *Proc. Natl. Acad. Sci. U.S.A.* 91:10747-10751; Stemmer (1994) *Nature* 370:389-391; Crameri et al. (1997) *Nature Biotech.* 15:436-438; Moore et al. (1997) *J. Mol. Biol.* 272: 336-347; Zhang et al. (1997) *Proc. Natl. Acad. Sci. U.S.A.* 94:4504-4509; Crameri et al. (1998) *Nature* 391:288-291; and U.S. Pat. Nos. 5,605,793 and 5,837,458.

Using methods such as PCR, hybridization, and the like, corresponding ARH3 sequences can be identified, such sequences having substantial identity to the sequences disclosed herein. See, for example, Sambrook J., and Russell, D. W. (2001) Molecular Cloning: A Laboratory Manual. (Cold Spring Harbor Laboratory Press, Cold Spring Harbor, N.Y.) and Innis, et al. (1990) PCR Protocols: A Guide to Methods and Applications (Academic Press, NY).

In a hybridization method, all or part of the ARH3 nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known ARH3-encoding nucleotide sequence disclosed herein.

Degenerate primers designed on the basis of conserved nucleotides or amino acid residues in the nucleotide sequence or encoded amino acid sequence can additionally be used.

The probe typically includes a region of nucleotide sequence that hybridizes under stringent conditions to at least about 12, about 25, at least about 50, 75, 100, 125, 150, 175, 200, 250, 300, 350, or 400 consecutive nucleotides of ARH3-encoding nucleotide sequence disclosed herein or a fragment or variant thereof. Preparation of Probes for Hybridization is Generally Known in the Art and is Disclosed in Sambrook and Russell, 2001, herein incorporated by reference.

For example, an entire ARH3 nucleic acid sequence, or one or more portions thereof, may be used as a probe capable of specifically hybridizing to corresponding ARH3-like sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify corresponding ARH3 sequences from a chosen organism by PCR.

This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) Molecular Cloning: A Laboratory Manual (2d ed., Cold Spring Harbor Laboratory Press, Plainview, N.Y.).

Hybridization of such sequences may be carried out under stringent conditions. Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (for example, 10 to 50 nucleotides) and at least about 60° C. for long probes (for example, greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may have about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the Tm can be approximated from the equation of Meinkoth and Wahl (1984) *Anal. Biochem.* 138:267-284: Tm=81.5° C.+16.6(log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.).

Expression vectors can be used to deliver nucleotides that encode an ARH3 polypeptide, or a polypeptide that acts as an activator or inhibitor of ARH3. Expression systems and expression vectors are known in the art. In general, an expression vector will include in the 5'-3' direction of transcription, a transcriptional and translational initiation region (a promoter), a DNA sequence encoding a protein of interest, and a transcriptional and translational termination region (termination region). The expression vector may be any expression vector that is capable of directing expression of a gene in a host cell, including prokaryotic, eukaryotic, or viral vector. These include, for example, microorganisms such as bacteria transformed with recombinant bacteriophage, plasmid, or cosmid DNA expression vectors; yeast transformed with yeast expression vectors; insect cell systems infected with virus expression vectors (for example, baculovirus), insects infected with virus expression vectors (for example, fall army worm infected with baculovirus); plant cell systems transformed with virus expression vectors (for example, cauliflower mosaic virus, CaMV; tobacco mosaic virus; TMV) or with bacterial expression vectors (for example, Ti or bacterial plasmids); or animal cell systems.

Examples of such vectors include pCMV-Script cytomeglovirus expression vectors for expression in mammalian cells, pESP and pESC vectors for expression in *S. pombe* and *S. cerevesiae*, pET vectors for expression in bacteria, pSPUTK vectors for high-level transient expression, and pPbac and pMbac vectors for expression in fall army worm (SF9) cells. Such vectors are available commercially from suppliers such as, for example, Invitrogen (Carlsbad, Calif.) or Stratagene (La Jolla, Calif.). In the use of viral vectors, it is understood that defective viral vectors (vectors that are genetically engineered to deliver a gene or gene product to a host but which cannot replicate in a host) are preferred. Procedures for the practice of in vitro and in vivo expression are well known to those of skill in the art and are further available with the specific expression products and cell lines from commercial suppliers.

Host cells may be transformed with a vector containing a nucleic acid molecule with a sequence that encodes, for example, an ARH3 polypeptide having poly(ADP-ribose) glycohydrolase activity. The host cell may be any eukaryotic or prokaryotic cell such as, for example a human, murine, *rattus*, bovine, insect, yeast or bacteria. Specific cell lines are well known to those of skill in the art and are available from suppliers such as the American Tissue Type Collection (ATCC, Manassas, Va.) and Stratagene (La Jolla, Calif.) and the like.

The control elements or regulatory sequences necessary for the proper expression of the insert may include promoters or enhancers (including both proximal and distal control elements) that interact with the host proteins to carry out transcription and translation. Such elements may vary in their strength and specificity and are known to those in the art. Depending on the vectors system and host utilized, any number of suitable transcription and translation elements, including constitutive and inducible promoters, may be used. For example, the LacZ promoter may be used in a bacterial cell; the baculovirus polyhedrin promoter may be used in an insect cell; plant promoters such as heat shock promoters, and storage protein promoters, plant virus promoters and the like may be used in a plant cell. In a mammalian cell expression system, an SV40 promoter or EBV promoter may be used, for example.

Methods and protocols for both prokaryotic and eukaryotic expression systems are generally known to those in the art. Further, the cells, vectors, growth medium may be purchased from commercial suppliers. The catalogs and product literature of commercial suppliers provide detailed protocols to enable the expression of proteins in prokaryotic and eukaryotic systems including bacterial, yeast, insect, insect cell, and mammalian cell systems.

Methods that are known to those skilled in the art may be used to construct expression vectors containing sequences encoding, for example, ARH3 and appropriate transcriptional and translational control elements. These methods include in vitro recombinant DNA techniques, synthetic techniques, and in vivo genetic recombination.

Methods of Use

It is disclosed herein that ARH3 has poly(ADP-ribose) glycohydrolase (PARG) activity. Thus, ARH3, like PARG, may regulate poly(ADP-ribose) levels in a cell. It is also disclosed herein that ARH3 degrades O-acetyl-ADP-ribose, generating ADP-ribose, and can regulate acetyl-ADP-ribose levels. ARHS also binds ADP-ribose and can alter ADP-ribose flux.

A method is provided herein for catalyzing the release of ADP-ribose from poly(ADP-ribose) or O-acetyl-ADP-ribose, comprising contacting the poly(ADP-ribose) or O-acetyl-ADP-ribose with an isolated ARH3 polypeptide, or fragment or variant thereof, thereby catalyzing the release of ADP ribose. In one embodiment, magnesium is provided. Also provided is a method for producing a polypeptide that catalyzes the release of ADP-ribose from poly(ADP-ribose) or O-acetyl-ADP-ribose, comprising culturing a host cell expressing a nucleotide sequence encoding an ARH3 polypeptide, or fragment or variant thereof, that catalyzes the release of ADP-ribose from poly(ADP-ribose) or O-acetyl- ADP-ribose, wherein the nucleotide sequence encoding ARH3 is operably linked to a heterologous promoter.

Methods for modifying DNA repair in a mammalian cell are provided, as well as methods for modifying chromatin structure in a mammalian cell. These methods include introducing into the cell an agent that modifies the activity of an ARH3 polypeptide, or variant or fragment thereof. Methods for modifying other cellular processes, such as apoptosis and cellular differentiation, are also encompassed. These methods would similarly include contacting the cell with an agent that modifies the activity of an ARH3 polypeptide, or variant or fragment thereof.

Methods to assess cellular differentiation, DNA repair, changes in chromatin structure and/or apoptosis are well known in the art. For example, Moravec and Riss (1998) *Promega Notes* 68:13, describe an assay for detecting apoptosis and cell death. Greenwalt et al. (2001) *J. Biomol. Screen.* 6:383-92 discloses a screening assay for assessing involvement in cellular differentiation of hematopoietic stem cells. Olive (1999) *Int. J. Radiat. Biol.* 75:395-405 disclose an assay for measuring DNA strand breaks and repair. Lu and Richardson (2004) *Biol. Proced. Online* 6:189-203 and Tollefsbol (2004) *Epigenetics Protocols*, Vol. 287, published by Human Press (ISBN: 1-59259-828-5) describe methods for analyzing changes in chromatin structure. One of skill in the art can readily identify and use assays that evaluate cellular differentiation, DNA repair, changes in chromatin structure and apoptosis ARH3 activity can be increased by increasing in the expression levels of ARH3 and/or increasing an enzymatic activity of ARH3. Many proteins have been identified that are modified with poly(ADP-ribose) polymers (pADPr), including PARP-1, histones, topoisomerase I, DNA polymerases α and β, and p53 (Ogata et al. (1981) *J. Biol. Chem.* 256:4135-4137; Althaus and Richter (1987) *Mol. Biol. Biochem. Biophys.* 37:1-237; Krupitza and Cerutti (1989) *Biochemistry* 28:2034-2040). Increased PARP activity is associated with increased DNA repair activity, as well as increased cell replication (Tanuma et al. (1978) *Exp. Cell Res.* 117:421-430; Leduc et al. (1988) *Biochim. Biophys. Acta* 968:275-282) telomere elongation (Smith and de Lange (2000) *Curr. Biol.* 10:1299-1302), and gene expression (Virag and Szabo (2002) *Pharmacol. Rev.* 54:375-429). Without being bound by theory, as histones are a major acceptor of poly(ADP-ribose), increased ARH3 PARG activity could lead to changes in chromatin structure, thereby altering the transcription of genes. An increase in ARH3 expression and/or activity results in increased cellular differentiation. An increase in the ARH3 activity also increases the degradation of the Sir2 signaling molecule, O-acetyl-ADP-ribose, and could inhibit Sir2-dependent pathways. Without being bound by theory, inhibition of Sir2-dependent pathways would result from the increased nicotinamide and decreased NAD+ that results from PARP activity (Zhang (2003) *BioEssays* 25:808-814). Thus, an increase in ARH3 activity can result in increased apoptosis.

In one embodiment, the poly(ADP-ribose) glycohydrolase activity of ARH3 is increased. In another embodiment, the O-acetyl-ADP-ribose hydrolysis activity of ARH3 is increased. In yet another embodiment, the poly(ADP-ribose) glycohydrolase and O-acetyl-ADP-ribose hydrolysis activities are increased.

Increased activity of ARH3 may be obtained, for example, by increasing expression of the ARH3 polypeptide, or variant or fragment thereof. For example, a nucleotide sequence may be introduced into a cell that encodes a protein that leads to increased ARH3 expression. The protein may be an ARH3 protein, or variant or fragment thereof, or a protein that acts to increase expression of endogenous ARH3, such as a transcription factor. A non protein-encoding nucleotide sequence that increases expression of ARH3 may also be introduced into a cell, such as an enhancer. Alternatively, a chemical compound that is capable of increasing ARH3 expression may be introduced into the cell.

Increased activity of ARH3 may also be obtained by increasing the enzymatic activity of the ARH3 protein with or without increasing expression levels. For example, a nucleotide sequence encoding an ARH3 protein variant that has greater activity than native ARH3 may be introduced into the cell, or a nucleotide sequence encoding an activator of ARH3 may be introduced into the cell. Alternatively, a chemical compound that is capable of increasing ARH3 activity may be introduced into the cell, such as an ARH3 agonist.

ARH3 activity can be decreased by decreasing in the expression levels of ARH3 and/or decreasing an enzymatic activity of ARH3. Inhibition of ARH3 could result in enhanced apoptosis in damaged cells.

Decreased activity of ARH3 can be obtained, for example, by decreasing expression of the ARH3 polypeptide, or variant or fragment thereof. For example, a nucleotide sequence may be introduced into a cell that encodes a protein that leads to decreased ARH3 expression, such as a protein that interferes with the ARH3 promoter. Alternatively, a non protein-encoding nucleotide sequence that decreases (inhibits) expression of ARH3, or variant or fragment thereof, may be introduced into a cell. The inhibitory nucleotide sequence may hybridize to a nucleotide sequence encoding the ARH3 polypeptide, or variant or fragment thereof. Inhibitory nucleotide sequences include, but are not limited to, an antisense nucleotide sequence, an siRNA or a ribozyme. A chemical compound that is capable of decreasing ARH3 expression may be introduced into the cell.

Antisense oligonucleotides as a method of suppression are well known in the art. It is well known that oligonucleotides, when administered to animals and humans, can have a useful therapeutic effect. In one embodiment, the oligonucleotide is at least about 10 nucleotides in length, such as, greater than about 20 bases in length, greater than about 30 bases in length, greater than about 40 bases in length, greater than about 50 bases in length, greater than about 100 bases in length, greater than about 200 bases in length or greater than about 300 bases in length. In one embodiment, the oligonucleotide has a ribozyme activity.

In one embodiment, inhibition of ARH3 activity is obtained through the use of antisense technology. An antisense oligonucleotide may be used therapeutically to inhibit translation of mRNA encoding ARH3. Synthetic antisense oligonucleotides may be produced, for example, in a commercially available oligonucleotide synthesizer. Herein is provided a means to therapeutically alter levels of expression of a human or other mammalian ARH3 by the use of a synthetic antisense oligonucleotide drug that inhibits translation of mRNA encoding ARH3. Synthetic antisense oligonucleotides, or other antisense chemical structures designed to recognize and selectively bind to mRNA, are constructed to be complementary to portions of the nucleotide sequence shown in SEQ ID NO: 1 or 5. An antisense oligonucleotide may be designed to be stable in the blood stream for administration to subjects by injection, or in laboratory cell culture conditions, for administration to cells removed from the subject. The antisense may be designed to be capable of passing through cell membranes in order to enter the cytoplasm and nucleus of the cell by virtue of physical and chemical properties of the antisense oligonucleotide which render it capable of passing through cell membranes (for example, by designing small, hydrophobic antisense oligonucleotide chemical structures) or by virtue of specific transport systems in the cell which recognize and transport the antisense oligonucleotide into the cell. In addition, the antisense oligonucleotide may be designed for administration only to certain selected cell populations by targeting the antisense oligonucleotide to be recognized by specific cellular uptake mechanisms that bind and take up the antisense oligonucleotide only within certain selected cell populations. For example, the antisense oligonucleotide may be designed to bind to transporter found only in a certain cell type, as discussed above. The antisense oligonucleotide may be designed to inactivate the ARH3 mRNA by (1) binding to the ARH3 mRNA and thus inducing degradation of the mRNA by intrinsic cellular mechanisms such as RNase I digestion, (2) by inhibiting translation of the mRNA target by interfering with the binding of translation-regulating factors or of ribosomes, or (3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (Cohen (1989) *Trends Pharmacol. Sci.* 10:435-7). In addition, coupling of ribozymes to antisense oligonucleotides is a promising strategy for inactivating target mRNA (Sarver et al. (1990) *Science* 247:1222-5). In this manner, an antisense oligonucleotide directed to ARH3 can be used to reduce ARH3 expression in particular target cells of a subject and in any clinical condition that may benefit from reduced expression of ARH3 (see below).

The synthesis of effective anti-sense inhibitors is known. Numerous approaches have been previously described and generally involve altering the backbone of the polynucleotide to increase its stability in vivo. Exemplary oligonucleotides and methods of synthesis are described in U.S. Pat. Nos. 5,661,134; 5,635,488; and 5,599,797 (phosphorothioate linkages), U.S. Pat. Nos. 5,587,469 and 5,459,255 (N-2 substituted purines), U.S. Pat. No. 5,539,083 (peptide nucleic acids) and U.S. Pat. Nos. 5,629,152; 5,623,070; and 5,610,289 (miscellaneous approaches).

Decreased activity of ARH3 may also be obtained by decreasing the enzymatic activity of the ARH3 protein with or without decreasing expression levels. For example, a nucleotide sequence encoding a protein that inhibits or inactivates ARH3 activity may be introduced into the cell.

Methods to assay for either an increase or decrease in activity of ARH3 are known in the art. For example, transcript levels can be assayed using standard molecular biology techniques. Alternatively, assays for enzymatic activity are known in the art. In an exemplary, non-limiting assay, poly(ADP-ribose) glycohydrolase activity is measured by incubating poly(ADP-ribose)PARP at 37° C. for 2 h with ARH3 in 50 mM potassium phosphate buffer, pH 7.5, with or without 10 mM $MgCl_2$ and/or 5 mM DTT (see Putt and Hergenrother (2004) *Analytical Biochemistry* 333:256-264; and U.S. Pat. Nos. 6,337,202 and 6,635,786). O-acetyl-ADP-ribose and ARH3 can be incubated in buffer (see Moss et al. (1985) *Proc. Natl. Acad. Sci. USA* 82: 5603-7).

In Vivo Use

Methods are also provided to increase ARH3 activity in a subject. These methods include administering a therapeutically effective amount of an agent that increases the activity of an ARH3 polypeptide, or variant or fragment thereof. In several embodiments, methods are provided herein for treating cancer, or a disorder associated with mild DNA damage such as cancer. These methods include administering a therapeutically effective amount of an agent that increases the activity of an ARH3 polypeptide, or variant or fragment thereof. Activation of ARH3 will provide enhanced chemotherapeutic benefit in cancer therapy or in the therapy of other diseases associated with enhanced poly (ADP-ribose) activity. Agents that increase the expression and/or activity of ARH3 are discussed above. These agents include, but are not limited to, nucleic acids encoding ARH3.

Methods are also provided herein for treating inflammation. The methods include selecting a subject with inflammation, and administering a therapeutically effective amount of an agent that increases the activity of an ARH3 polypeptide, or variant or fragment thereof. Agents that increase the expression and/or activity of ARH3 are discussed above. These agents include, but are not limited to, nucleic acids encoding ARH3. Thus, methods are provided herein for treating disorders associated with inflammation, such as graft-versus host disease, atherosclerosis, transplant rejection, allergy or inflammatory arthritis. In any of these methods an agent that increases the activity of an ARH3 polypeptide can be used in conjunction with another immunosuppressive agent.

Rejection of transplanted organs and tissues are an example of an undesired consequence of normal immunity, which can often result in damage to and/or rejection of the transplant. Tissue rejection, also called host-versus-graft disease, is a consequence of organ or tissue transplantation caused by the transplant recipient's (host's) immune response to the transplanted organ/tissue which can damage or destroy it. Ordinarily, the immune response protects the body from potentially harmful substances (antigens) such as microorganisms, toxins, and cancer cells. The immune system distinguishes "self" from "foreign" by reacting to proteins on the surfaces of cells. It reacts against substances it recognizes as foreign (antigens). The presence of foreign blood or tissue in the body triggers an immune response that can result in blood transfusion reactions and transplant rejection when antibodies are formed against foreign antigens on the transplanted or transfused material. Before transplant, tissue is "typed" according to the antigens it contains (histocompatibility antigens).

No two people (except identical twins) have identical tissue antigens. Therefore, in the absence of immunosuppressive drugs, organ and tissue transplantation would almost always causes an immune response against the foreign tissue (rejection), which would result in destruction of the transplant. Though tissue typing ensures that the organ or tissue is as similar as possible to the tissues of the recipient, unless the donor is an identical twin, no match is perfect and the possibility of organ/tissue rejection remains. Immunosuppressive therapy is used to prevent organ rejection. In one embodiment, methods are provided for treating transplant rejection. The methods include selecting a subject with a transplant, such as a heart, lung, pancreas or kidney transplant, and administering to the subject a therapeutically effective amount of an agent that increases the expression of ARH3, thereby treating the rejection in the subject with the transplant. The methods can include administering an additional immunotherapeutic agent, such as, but not limited to Cyclosporine A, FK506, or analogs thereof, or antibodies such as a monoclonal antibody that specifically binds CD3 (such as OKT3), CD4, or CD8.

Methods are also provided herein for treating graft-versus-host disease. Graft-versus host disease (GVHD) can be a complication of allogenic bone marrow transplantation in which cells from the transplanted bone marrow recognize the host tissue is foreign and produce an immune response against host tissue. Briefly, T cells from the bone marrow graft produce cytokines, such as Tumor Necrosis Factor (TNF)-alpha and interferon-gamma (IFNg). A wide range of host antigens can initiate GVHD, such as the human leukocyte antigens (HLAs). However, GVHD has been documented to occur even when HLA-matched siblings are the donor and recipients, due to differences in the minor histocompatibility antigens. GVHD occurs in two forms, an acute form that occurs within 100 days of bone marrow transplant and a chronic form that occurs after more than 100 days of bone marrow transplant. Acute GVHD is characterized by selective damage to the liver, skin, mucosa and the gastrointestinal tract. Other target organs of GVHD include the organs of the immune system, such as the thymus, and the lungs (in the form of idiopathic pneumonitis).

Acute GVHD of the gastrointestinal tract can result in watery diarrhea, abdominal pain, nausea, and vomiting. This is typically diagnosed via intestinal biopsy. Liver GVHD is measured by the bilirubin level in acute patients. Skin GVHD results in a diffuse maculopapular rash, sometimes in a lacy pattern. Acute GVHD can be staged as an overall grade (skin-liver-gut, with each organ staged individually from a low grade of I to a high grade of IV. Patients with grade IV GVHD usually have a poor prognosis. If the GVHD is severe and requires intense immunosuppression involving steroids and additional agents to get under control, the bone marrow recipient can develop severe infections as a result of the immunosuppression and may die of infection. Chronic GVHD damages the same organs as the acute form of the disease, but also causes changes to the connective tissue, the skin and the exocrine glands. Any of the forms of GVHD can be treated using the methods disclosed herein.

The methods include selecting a subject with GVHD, such as acute or chronic GVHD, and administering to the subject a therapeutically effective amount of an agent that increases the expression of ARH3, thereby treating the subject with acute or chronic GVHD.

Generally, intensive prophylaxis with immunosuppressive drugs is used for all subjects undergoing allogeneic bone marrow transplantation. Compounds in use include cyclosporine, tacrolimus, methotrexate, mycophenolate mofetil, corticosteroids or antithymocyte globulin (ATG). The decrease in the incidence and severity of acute GVHD is in large part due to the widespread prophylactic use of these drugs, particularly cyclosporine and methotrexate. Additionally, monoclonal antibodies (for example, anti-CD3, anti-CD5, and anti-IL-2 antibodies), Mycophenolate mofetil, Alemtuzumab, Antithymocyte globulin (ATG), and Sirolimus are of use to treat acute GVHD. Tacrolimus, Mycophenolate mofetil, Antithymocyte globulin (ATG), Thalidomide, Daclizumab, Extracorporeal photopheresis, Infliximab, and Clofazimine are of use to treat chronic GVHD. The present methods can be combined with the use of a therapeutically effective amount of one or more of these compounds.

Allergy is another example of an immune-mediated disorder. An allergy is a collection of symptoms caused by an exaggerated immune response or reaction to substances that do not trigger an immune response in most people. The term "allergy" has become synonymous with Type I hypersensitivity (IgE-mediated allergy). Four different types of hypersensitivity were described by Coomb and Gell (Types I, II, III and IV), as a pedagogical way to increase the understanding of different immune reactions, which could be provoked by many antigens. In practice these types do not necessarily occur in isolation from each other.

Allergic diseases generally begin in childhood, although they can arise at any age. Development of allergic disease is associated with an allergic constitution due to heredity and to environmental and health factors. An allergic response involves an increased production of allergen-specific IgE antibodies, which may lead to clinical symptoms such as rhinitis, asthma, eczema, colic pains or diarrhea. A state of hyperreactivity often accompanies an allergic reaction. If this hyperreactivity occurs in the respiratory tract, everyday stimuli like dust, tobacco smoke, cold air and perfumes may lead to allergy-like symptoms. Thus, in one embodiment, methods are provided for treating allergy. The methods include selecting a subject with an allergy, and administering to the subject a therapeutically effective amount of an agent that increases the expression of ARH3, thereby treating the allergy.

In another embodiment, a method is provided for treating inflammatory arthritis. The methods include selecting a subject with an inflammatory arthritis, and administering to the subject a therapeutically effective amount of an agent that increases the expression of ARH3, thereby treating the inflammatory arthritis. The methods can include administering another (different) immunosuppressive agent to the subject. In particular examples, the immunosuppressive agent is a non-steroidal anti-inflammatory agent, such as diclofenac, diflunisal, etodolac, flurbiprofen, ibuprofen, indomethacin, ketoprofen, ketorolac, nabumetone, naproxen, oxaprozin, piroxicam, sulindac, tolmetin, celecoxib, or rofecoxib, a steroid, such as cortisone, dexamethasone, hydrocortisone, methylprednisolone, prednisolone, prednisone, or triamcinolone, or an immunosuppressive agent, for example cyclosporin, tacrolimus, mycophenolic acid, or sirolimus.

Methods are also disclosed herein for treating atherosclerosis. The methods can include selecting a subject with atherosoclersis, and administering to the subject a therapeutically effective amount of an agent that increases the expression of ARH3, thereby treating the atherosclerosis. The methods can include administering another (different) agent to the subject, such as a cholesterol-lowering agent (for example, a statin).

The agent can be administered locally. By way of example, one method of administration to the knee, hip and/or shoulder of an individual is by intra-articular injection. For administration to the knee, for example, the joint to be injected is washed with a betadine solution or other antiseptic. A solution of about one percent lidocaine hydrochloride is injected into the skin and subcutaneous tissue. A 3-way stopcock/needle assembly is utilized to administer the compound via an 18-30 gauge needle. The therapeutic agent is injected into the joint space using a standard lateral approach well known to those skilled in the art. The needle and needle tract are cleansed by flushing with 1% lidocaine hydrochloride through the 3-way stopcock assembly as the needle is withdrawn. The knee is then moved through a flexion-extension arc and then immobilized in full extension. The patient can be confined to bed for approximately 24 hours to minimize movement and minimize leakage of the agent from the joint.

Methods are also provided to decrease ARH3 activity and/or expression in a subject. These methods include administering a therapeutically effective amount of an agent that inhibits or decreases the activity of an ARH3 polypeptide, or variant or fragment thereof.

Over-activation of PARP enzymes has been implicated in the pathogenesis of numerous diseases, and inhibitors of PARP and/or PARG activity have been shown to play a role in treating these diseases. See, for example, U.S. Pat. Nos. 6,635,786, 6,337,202; see also, for example, U.S. Published Application Nos. 20030078212 and 20050148575; WIPO International Publication No. WO 98/27975. PARP inhibitors have also been reported to be effective in treating cancer. See U.S. Pat. Nos. 5,032,617; 5,177,075; 5,215,738; and 5,041,653.

In several embodiments, methods are provided for treating a disorder associated with excessive DNA damage in a subject by administering an agent that decreases ARH3 activity and/or expression. In several examples, the disease condition or disorder is associated with excessive DNA damage. Disorders associated with excessive DNA damage include, but are not limited to, an autoimmune disease, acute pain, arthritis, atherosclerosis, cachexia, cardiovascular disorders, chronic pain, degenerative diseases, diabetes, head trauma, hyperglycemia, immune senescence, inflammatory bowel disorders, ischemia, macular degeneration, muscular dystrophy, myocardial infarction, tissue damage resulting from ischemia and reperfusion injury, neurological disorders and neurodegenerative diseases, such as Alzheimer's disease, Huntington's disease, Parkinson's disease, and neurotoxicity generally, neuronal tissue damage or disease, neuropathic pain, nervous insult, osteoarthritis, osteoporosis, peripheral nerve injury, renal failure, resuscitated hemorrhagic shock, retinal ischemia, septic shock, skin aging, stroke, diseases or disorders relating to lifespan or proliferative capacity of cells or organisms, diseases or disease conditions induced or exacerbated by cellular senescence, neoplastic disorders, inborn genetic errors, myocardial infarctions, and aging.

In several embodiments, methods are provided for treating a tumor in a subject. Tumors include, but are not limited to, a cancer of the adrenal gland, bladder, bone, bone marrow, brain, breast, central nervous system, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. Exemplary cancers include adenocarcinoma, leukemia, lymphoma, melanoma, myeloma, sarcoma, teratocarcinoma, hyperplasia and hypertrophy. Exemplary cancers also include ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, gliomas, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva, and Wilm's tumor.

The presently disclosed methods include administering an agent that increases or decreases ARH3 activity and/or expression with or without one or more other pharmaceutical agents, to the subject in a pharmaceutically compatible carrier. The administration is made in an amount effective to treat cancer, or a disorder associated with excessive DNA damage. In one example, antisense oligonucleotides for ARH3 inhibition are used alone or in combination with other chemotherapeutic agents to treat neoplastic disorder. Inhibitors of ARH3 activity also can be used in combination with DNA-binding antitumor drugs for treating cancer and for the treatment of disorders associated with excessive DNA damage.

The vehicle in which the agent that increases or decreases ARH3 activity and/or expression includes any pharmaceutically acceptable compositions known to one of skill in the art. Any of the common carriers, such as sterile saline or glucose solution, can be utilized with the agents disclosed herein. For use in any of the therapeutic methods disclosed herein, administration of the agent can be systemic or local. Routes of administration include but are not limited to oral and parenteral routes, such as intravenous (iv), intraperitoneal (ip), rectal, topical, ophthalmic, nasal, and transdermal.

Pharmacological compositions for use can be formulated in a conventional manner using one or more pharmacologically (for example, physiologically or pharmaceutically) acceptable carriers including excipients, as well as optional auxiliaries that facilitate processing of the active compounds into preparations that can be used pharmaceutically. Proper formulation is dependent upon the route of administration chosen. In addition, one of skill in the art can readily select a suitable route of administration, including, but not limited to, intravenous, intramuscular, intraperitoneal, transmucosal, subcutaneous, transdermal, transnasal, inhalation, and oral administration.

Thus, for injection, the active ingredient can be formulated in aqueous solutions, preferably in physiologically compatible buffers. For example, intravenous injection may be by an aqueous saline medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives, surfactants, antioxidants (for example, ascorbyl palmitate, butyl hydroxy anisole (BHA), butyl hydroxy toluene (BHT) and tocopherols), chelating agents, viscomodulators, tonicifiers, flavorants, colorants, odorants, and the like. A more complete explanation of parenteral pharmaceutical carriers can be found in Remington: The Science and Practice of Pharmacy (19$^{th}$ Edition, 1995) in chapter 95.

For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. A 2-(4-piperazinyl)-substituted 4H-1-benzopyran-4-one compound can also be formulated for use in inhalation therapy, such as for the treatment of subjects with inflammation of the lungs. For administration by inhalation, the active ingredient is conveniently delivered in the form of an aerosol spray presentation from pressurized packs or a nebuliser, with the use of a suitable propellant.

The agent that increases or decreases the expression and/or activity of ARH3 can be formulated for parenteral administration by injection, for example, by bolus injection or continuous infusion. Similarly, ARH3 inhibitors or activators can be formulated for intratracheal or for inhalation. Such compositions can take such forms as suspensions, solutions or emulsions in oily or aqueous vehicles, and can contain formulatory agents such as suspending, stabilizing and/or dispersing agents. Other pharmacological excipients are known in the art.

Examples of other pharmaceutical compositions can be prepared with conventional pharmaceutically acceptable carriers, adjuvants and counterions as would be known to those of skill in the art. The compositions are preferably in the form of a unit dose in solid, semi-solid and liquid dosage forms such as tablets, pills, powders, liquid solutions or suspensions. Semi-solid formulations can be any semi-solid formulation including, for example, gels, pastes, creams and ointments. Liquid dosage forms may include solutions, suspensions, liposome formulations, or emulsions in organic or aqueous vehicles.

The therapeutically effective amount of an agent that increases or decreases ARH3 expression and/or activity, or a pharmaceutically acceptable salt thereof, may be administered in conjunction with an additional agent. This administration can be simultaneous or sequential, in any order. This agent may be, for example, a chemotherapeutic agent, including, but not limited to, chemical agents, anti-metabolites and antibodies.

Therapeutically effective doses of the presently described compounds can be determined by one of skill in the art. The relative toxicities of the compounds make it possible to administer in various dosage ranges. In one example, the compound is administered orally in single or divided doses. The specific dose level and frequency of dosage for any particular subject may be varied and will depend upon a variety of factors, including the activity of the specific compound, the extent of existing disease activity, the age, body weight, general health, sex, diet, mode and time of administration, rate of excretion, drug combination, and severity of the condition of the host undergoing therapy.

A therapeutically effective dose may be sufficient to inhibit ARH3 PARP or O-acetyl-ADP-ribose hydrolase activity; to treat or prevent tissue damage resulting from cell damage or death due to necrosis or apoptosis; to treat tissue damage resulting from ischemia and reperfusion injury, neurological disorders and neurodegenerative diseases; to prevent or treat vascular stroke; to treat or prevent cardiovascular disorders; to treat other conditions and/or disorders such as those listed above; to extend the lifespan and proliferative capacity of cells; to alter gene expression of senescent cells; or to radiosensitize hypoxic tumor cells.

Methods for Screening for Modulators of ARH3 Activity

Methods are provided for screening a candidate molecule for use in altering differentiation of a cell, for altering DNA repair in a cell, for altering apoptosis, modifying chromatin structure, or affecting aging, longevity, or senescence. Methods are provided for screening a candidate molecule for use in altering or for use in treating cancer or a disorder associated with excessive DNA damage. These methods include contacting an ARH3 polypeptide with poly(ADP-ribose) or O-acetyl-ADP-ribose in the presence and absence of the molecule, and assessing the ability of ARH3 to produce ADP-ribose. A change in the amount of ADP-ribose produced in the presence of the candidate molecule indicates that the molecule is capable of altering the hydrolysis activity of ARH3. An ARH3 modulator is a compound that can activate or inhibit ARH3 activity. In one embodiment, the molecule is an inhibitor of ARH3 hydrolysis activity. In one embodiment, the molecule is an activator of ARH3 hydrolysis activity.

The ability of a molecule to alter the poly(ADP-ribose) glycohydrolase (PARG) activity or O-acetyl-ADP-ribose hydrolysis activity of ARH3 is indicative that the molecule is of use to modulating cellular processes involving poly(ADP-ribosyl)ation, or a Sir-related pathway such as cellular differentiation, DNA repair, and apoptosis, and also in treating cancer, or disorders associated with excessive DNA damage. The ability of a molecule to alter the O-acetyl-ADP-ribose hydrolase activity of ARH3 is indicative that the molecule is of use for modulating gene silencing and chromatin structure in a cell.

Further provided is a method for screening a candidate molecule for its use in altering the ability of ARH3 to bind ADP-ribose. This method comprises contacting an ARH3 polypeptide with ADP-ribose in the presence and absence of the molecule, and assessing the ability of ARH3 to bind ADP-ribose. A molecule that interferes with the ability of ARH3 to bind free ADP-ribose would decrease the activity of ARH3. Alternatively, a molecule that increases the ability of ARH3 to bind free ADP-ribose may increase ARH3 activity. Methods are provided for screening a candidate molecule for use in altering differentiation of a cell, for altering DNA repair in a cell, for altering apoptosis, modifying chromatin structure, or affecting aging, longevity, or senescence. Methods are provided for screening a candidate molecule for use in altering or for use in treating cancer or a disorder associated with excessive DNA damage. These methods include assessing the ability of ARH3 to bind ADP-ribose. The ability of a molecule to alter the ability of ARH3 to bind ADP-ribose is indicative that the molecule is of use in altering differentiation of a cell, for altering DNA repair in a cell, for altering apoptosis, modifying chromatin structure, affecting aging, affecting longevity, affecting senescence, treating cancer or treating a disorder associated with excessive DNA damage.

It should be noted that methods are provided for screening a candidate molecule for use in altering differentiation of a cell, altering DNA repair in a cell, altering apoptosis, modifying chromatin structure, affecting aging, affecting longevity, or affecting senescence, treating cancer, or treating a disorder associated with excessive DNA damage that include either (1) contacting an ARH3 polypeptide with poly(ADP-ribose) or O-acetyl-ADP-ribose in the presence and absence of the molecule, and assessing the ability of ARH3 to produce ADP-ribose; or (2) contacting an ARH3 polypeptide with ADP-ribose and assessing the ability of ARH3 to bind ADP-ribose. The method an also include both (1) contacting an ARH3 polypeptide with poly(ADP-ribose) or O-acetyl-ADP-ribose in the presence and absence of the molecule, and assessing the ability of ARH3 to produce ADP-ribose; and (2) contacting an ARH3 polypeptide with ADP-ribose and assessing the ability of ARH3 to bind ADP-ribose, in any order.

Methods for assessing the ability of ARH3 to bind ADP-ribose are well known in the art. For example, ARH3 may be incubated with [$^{14}$C]ADP-ribose at 30° C. for 16 hours. Unbound ADP-ribose may be removed by binding to Affi-gel boronate (Bio-Rad), and the ARH3 with ADP-ribose bound may be collected for radioassay. See, for example, Example 4.

A method is also provided for screening for a candidate molecule capable of altering the hydrolysis activity of ARH3, comprising contacting a candidate molecule with an ARH3 polypeptide in the presence of poly(ADP-ribose) or O-acetyl-ADP-ribose; and determining the amount of ADP-ribose produced by the ARH3 polypeptide, wherein a change in the amount of ADP-ribose produced in the presence of the candidate molecule indicates that the molecule is capable of altering the hydrolysis activity of ARH3.

The screening may be conducted using any assay for PARG activity or O-acetyl-ADP-ribose hydrolase activity known to those skilled in the art. Methods for assaying for PARG or O-acetyl-ADP-ribose hydrolase activity are well known in the art. See, for example, Examples 1 and 2. For example, a known amount of ARH3 may be incubated under standardized conditions with poly(ADP-ribose) or O-acetyl- -ADP-ribose in the presence of the candidate molecule. After an appropriate period of time, the reaction is stopped and the reaction mixture separated by gel electrophoresis. The amount of ADP-ribose released in the reaction is quantified and the effect of the inhibitor or activator on enzymatic activity therefore determined. The concentration of the inhibitor or activator can be varied as necessary to determine the $K_i$ value of the inhibitor or activator according to standard procedures.

Methods to assess cellular differentiation, DNA repair, changes in chromatin structure and/or apoptosis are well known in the art. See above for examples. Methods to assess the use of a molecule in treating cancer or a disorder associated with excessive DNA damage are well known in the art. See, for example, U.S. Published Application Nos. 20050148575 and 20030078212.

The ARH3 polypeptide may be generated in vitro by culturing a cell transformed with a nucleic acid molecule encoding ARH3 under conditions effective to express the polypeptide. The assay can be performed in cells or cell extracts. In another embodiment, an isolated ARH3 polypeptide is immobilized on a solid support. In a further embodiment, an isolated ARH3 polypeptide is in solution.

The candidate molecule can be any compound of interest, including chemical compounds, small molecules, polypeptides or other biological agents (for example antibodies or cytokines). In several examples, a panel of potential chemotherapeutic agents, or a panel of potential immunosuppressive agents are screened. In other embodiments a panel of polypeptide variants is screened.

The disclosure is illustrated by the following non-limiting Examples.

EXAMPLES

The Sir2 family of NAD-dependent N-acetyl-protein deacetylases participates in the regulation of gene silencing, chromatin structure, and longevity. In the Sir2-catalyzed reaction, the acetyl moiety of N-acetyl-histone is transferred to the ADP-ribose of NAD, yielding O-acetyl-ADP-ribose and nicotinamide. It is disclosed herein that the poly(ADP-ribose) glycohydrolase ARH3, hydrolyzed O-acetyl-ADP-ribose to produce ADP-ribose in a time- and $Mg^{2+}$-dependent reaction and thus participated in two signaling pathways. This O-acetyl-ADP-ribose hydrolase belongs to a family of three, structurally related 39-kDa ADP-ribose-binding proteins (ARH1-3). ARH1 hydrolyzes ADP-ribosylarginine, whereas ARH3 degraded poly(ADP-ribose). ARH3-catalyzed generation of ADP-ribose from O-acetyl-ADP-ribose was significantly faster than from poly(ADP-ribose). Like the degradation of poly(ADP-ribose) by ARH3, hydrolysis of O-acetyl-ADP-ribose was abolished by replacement of the vicinal aspartates at positions 77 and 78 of ARH3 with alanine. The rate of O-acetyl-ADP-ribose hydrolysis by recombinant ARH3 was 250-fold that observed with ARH1; ARH2 and poly-ADP-ribose glycohydrolase were inactive. Thus, the Sir2 reaction product, O-acetyl-ADP-ribose, is degraded by ARH3.

Example 1

Methods for Examples 2-5

Mouse and human ADP-ribosyl hydrolase constructs and mutagenesis. Based on DNA sequences (GenBank) of mouse ARH1 (mARH1, L13290), mouse ARH2 (mARH2, AJ427360), mouse ARH3 (mARH3, AJ427296) (SEQ ID NO: 5), human ARH1 (hARH1, L13291), human ARH2 (hARH2, AJ313429), and human ARH3 (hARH3, AJ313333) (SEQ ID NO: 1), forward and reverse PCR primers with unique restriction enzyme sites were designed (see Table 1). Mouse and human hydrolase cDNAs were amplified from a Marathon-Ready brain cDNA library (Clontech) using the Advantage 2 PCR Enzyme Systems (Clontech). PCR products were subcloned using a Zero Blunt TOPO PCR Cloning kit (Invitrogen). Plasmid cDNAs were isolated (QIAprep Spin Miniprep Kit, Qiagen). Mutations were generated using the Stratagene QuikChange site-directed mutagenesis method, according to the manufacturer's protocol. Complementary mutant primers used to generate ARH3 mutants are shown in Table 1. The entire coding regions were ligated into pGEX-2T expression vector (Amersham Pharmacia Biotech), for transfection into *E. coli* BL21 Rosetta supercompetent cells (Novagen). Positive clones were confirmed by DNA sequencing (ABI PRISM 377, Perkin-Elmer) of the entire open reading frames in both directions. Proteins synthesized as GST-fusion products were purified using glutathione-Sepharose 4B according to the manufacturer's instructions (Amersham Pharmacia Biotech).

Anti-ARH3 Antibodies. Rabbits were immunized with a peptide (CTDVLAQSLHRVFQESS) (SEQ ID NO: 10) representing amino acids 355-370 of mouse ARH3 with cysteine added at the N-terminus to facilitate coupling to keyhole limpet hemocyanin. Antibodies were purified from sera of two rabbits, using a peptide affinity column.

Tissue Fractionation and Western Blotting. To prepare proteins for Western blotting, tissue from one to four C57BL6J mice of each sex, 1 g per 5 ml of homogenizing buffer (20 mM Tris-HCl, pH 8.0/1 mM EDTA/1 mM $NaN_3$/1 mM DTT/250 mM sucrose), containing 0.5 mM 4-(2-aminoethyl)benzenesulfonyl fluoride, leupeptin (10 μg/ml), aprotinin (10 μg/ml), and pepstatin A (1 μg/ml) was homogenized with 20 strokes of a Dounce tissue grinder (Wheaton Scientific). The homogenate was centrifuged (1000×g, 10 min), and the postnuclear supernatant was centrifuged (100,000×g, 90 min) to separate cytosol and membrane fractions. Membranes were homogenized in 0.5 ml of homogenizing buffer.

HepG2 cells were grown (37° C., 5% $CO_2$/95% air) in DMEM with 10% FBS (GIBCO), penicillin G (100 units/ml), and streptomycin (100 μg/ml) on collagen I (Sigma)-coated dishes (Becton Dickinson). Unless otherwise indicated, cells were incubated overnight (16-18 h) in the same medium without FBS before experiments. Confluent cells from ten 15-cm plates (3×$10^8$ cells total) were harvested by scraping in ice-cold PBS (0.14 M NaCl/8.1 mM $Na_2HPO_4$/1.5 mM $KH_2PO_4$, BioSource International, Camarillo, Calif.), washed twice with the same solution, sedimented by centrifugation (1,000×g, 5 min), and homogenized with 10 strokes in a 7-ml Dounce tissue grinder (Wheaton Scientific) in 4 ml of TKMS buffer (50 mM Tris, pH 7.5/25 mM

TABLE 1

PCR primers.

| Primer | PCR primers used to generate recombinant ARH enzyme | Restriction |
|---|---|---|
| mARH1 forward | TAGGATCC$^1$ATGGTGGGGGCTGATT$_{17}$ (SEQ ID NO: 11) | BamHI |
| mARH1 reverse | TAGAATTC$^{1089}$CTAGGGATCTAATACGGA$_{1072}$ (SEQ ID NO: 12) | EcoRI |
| mARH2 forward | TACCCGCCA$^1$ATGGAGAAGTTCAAGGCTGCA$_{21}$ (SEQ ID NO: 13) | Sma I |
| mARH2 reverse | TAGAATTC$^{1062}$TTACTTTTCTTCTGTGGACAG$_{1042}$ (SEQ ID NO: 14) | EcoRI |
| mARH3 forward | TAGGATCC$^1$ATGGCGGTGGCTGCGGCGGCA$_{21}$ (SEQ ID NO: 15) | BamHI |
| mARH3 reverse | TAGAATTC$^{1113}$TTACGAGCTCTCCTGGAAGAC$_{1093}$ (SEQ ID NO: 16) | EcoRI |
| hARH1 forward | TACCCGCCA$^1$ATGGAGAAGTATGTGGCTGC$_{20}$ (SEQ ID NO: 17) | Sma I |
| hARH1 reverse | TAGAATTC$^{1074}$CTAAAGGGAAATTACAGTGTCTTC$_{1053}$ (SEQ ID NO: 18) | EcoRI |
| hARH2 forward | TAGGATCC$^1$ATGGAGAAATTTAAGGCTGCG$_{21}$ (SEQ ID NO: 19) | Sma I |
| hARH2 reverse | TAGAATTC$^{1065}$TTACTTCTCCTCTGTGGACAG$_{1045}$ (SEQ ID NO: 20) | EcoRI |
| hARH3 forward | TAGGATCC$^1$ATGGCCGCAGCGGCGATGGCG$_{21}$ (SEQ ID NO: 21) | BamHI |
| hARH3 reverse | TAGAATTC$^{1092}$TCAACTCTTCTGGAAGACACG$_{1072}$ (SEQ ID NO: 22) | EcoRI |
| PCR primers used to generate human ARH3 mutants | | Mutation |
| D77N/D78N forward | $^{216}$CTTGTACTACACA<u>A</u>AT<u>A</u>ACACAGCCATGGCC$_{246}$ (SEQ ID NO: 23) | G→A |
| D77N/D78N reverse | $^{246}$GGCCATGGCTGTGT<u>T</u>AT<u>T</u>TGTGTAGTACAAG$_{216}$ (SEQ ID NO: 24) | C→T |
| E261Q/E262Q forward | $^{770}$CGGTGACCAGG<u>C</u>AG<u>C</u>AAGTGGTGTCTGAG$_{798}$ (SEQ ID NO: 25) | G→C |
| E261Q/E262Q reverse | $^{798}$CTCAGACACCACTT<u>G</u>CT<u>G</u>CCTGGTCACCG$_{770}$ (SEQ ID NO: 26) | C→G |
| E238Q/E239Q forward | $^{700}$GAGTTGGGCATG<u>C</u>AG<u>C</u>AGCGTCCATACTCC$_{729}$ (SEQ ID NO: 27) | G→C |
| E238Q/E239Q reverse | $^{729}$GGAGTATGGACGCT<u>G</u>CT<u>G</u>CATGCCCAACTC$_{700}$ (SEQ ID NO: 28) | C→G |

Number 1 is A of the translation initiation codon.
Restriction enzyme sites are in italics.
Mutated nucleotides are shaded and mutated amino acids are underlined.
m; mouse, h; human.

KCl/5 mM MgCl$_2$/250 mM sucrose) containing 0.5 mM 4-(2)-aminomethylbenzenesulfonyl fluoride, leupeptin (10 µg/ml), aprotinin (10 µg/ml), and pepstatin A (1 µg/ml). The homogenate was centrifuged (4,000×g, 10 min) to sediment nuclei, unbroken cells, and cell debris (crude nuclear fraction), and supernatant was centrifuged (100,000×g, 90 min, 4° C.) to separate cytosol and membranes.

To prepare pure nuclei, the crude nuclear fraction was washed once with TKMS buffer, incubated at 37° C. for 45 min in 2 ml of TKMS buffer, washed twice with TKMS buffer, and applied to the top of a sucrose gradient (2-ml layers of TKMS buffer containing 2.5, 2.25, 2.0, 1.75, and 1.5 M sucrose), which was then centrifuged at 100,000×g for 90 min at 4° C. Pure nuclei were collected at the 1.75-2 M interface and washed twice with TKMS buffer.

Samples (25 µg) of homogenate proteins and recombinant ARH3 (25 ng) were subjected to SDS-PAGE in 4-12% gels and transferred to nitrocellulose membranes, which were reacted with antibodies against ARH3 (0.5 µg/ml). Secondary goat anti-rabbit IgG antibodies conjugated to horseradish peroxidase (Southern Biotech) were detected using SuperSignal Chemiluminescent substrate (Pierce), followed by exposure to X-ray films (Kodak).

Northern blotting. Poly (A)$^+$ RNA (2 µg) from mouse tissues (Ambion Inc.) was hybridized at 42° C. in 30 ml of hybridization buffer (Ambion) overnight, with 25 ng of [$^{32}$P]-labeled ARH3 cDNA. In separate experiment, [$^{32}$P]-labeled (10 ng) GAPDH and β-actin cDNA were hybridized to the blot as a loading control.

ADP-ribose-proteins synthesized by bacterial toxins as potential ARH substrates. ADP-ribose-proteins were synthesized using toxin ADP-ribosyltransferases. Synthesis of [$^{32}$P] ADP-ribose-arginine-protein, was catalyzed by cholera toxin A subunit (250 µg), that had been activated by incubation (30°, 15 min) with 100 mM DTT (Ohno et al. (1995) *Anal. Biochem.* 231:115-122). Mouse brain membrane fraction (1 mg protein) as ADP-ribose acceptor, plus activated cholera toxin, 10 µM [$^{32}$P] NAD (10 µCi/reaction), 10 mM MgCl$_2$, and 5 mM DTT in 50 mM potassium phosphate, pH 7.5 (total volume, 1 ml) were incubated at 37° for 2 h.

Gαi and Gαo were extracted from brain membrane fraction (50 mg) by stirring on ice for 1 h in 4 ml of homogenizing buffer plus 1% sodium cholate. After centrifugation (100,000×g, 1 h), the supernatant containing G-proteins was collected (Waldo et al. (1987) *Biochem. J.* 246:431-439). Synthesis of ADP-ribose-cysteine-Gαi/Gαo was catalyzed by pertussis toxin that had been activated by incubation (30° C., 15 min) with 100 mM DTT. Extracted G-protein (1 mg) as ADP-ribose acceptor, plus activated pertussis toxin (50 µg), 10 µM [$^{32}$P] NAD (10 µCi/reaction), 10 mM MgCl$_2$, and 5 mM DTT in 50 mM potassium phosphate, pH 7.5 (total volume, 1 ml) were incubated at 37° for 2 h.

Synthesis of ADP-ribose-diphthamide-elongation factor II was catalyzed by *Pseudomonas* exotoxin A, that had been activated by incubation (30° C., 15 min) with 100 mM DTT (Lee and Iglewski (1984) *Proc. Natl. Acad. Sci. U.S.A* 81:2703-2707). Mouse brain cytosol (1 mg protein), as ADP-ribose acceptor, plus activated *Pseudomonas* exotoxin A (400 µg), 10 µM [$^{32}$P] NAD (10 µCi/reaction), 10 mM MgCl$_2$, and 5 mM DTT in 50 mM potassium phosphate, pH 7.5 (total volume, 1 ml) were incubated at 37° C. for 2 h.

Synthesis of ADP-ribose-asparagine-Rho was catalyzed by *Clostridium botulinum* C3 enzyme that had been activated by incubation (30° C., 15 min) with 100 mM DTT (Morii et al. (1988) *J. Biol. Chem.* 263:12420-12426). Brain cytosol (1 mg protein), as ADP-ribose acceptor, plus *Clostridium botulinum* C3 toxin (10 µg), 10 µM [$^{32}$P] NAD (10 µCi/reaction), 10 mM MgCl$_2$, and 5 mM DTT in 50 mM potassium phosphate, pH 7.5 (total volume, 1 ml) were incubated at 37° C. for 2 h.

Reactions were stopped by addition of 20% trichloroacetic acid (1 ml) and after 1 h on ice, precipitated proteins were sedimented by centrifugation (16,000×g, 4° C., 30 min), washed three times with ice-cold acetone, and dissolved with 50 mM potassium phosphate, pH 7.5, to be used as substrates for ARH assays.

Assay of ARH activity using autoradiography. Samples (50 µg) of [$^{32}$P]ADP-ribosylated proteins synthesized by bacterial toxins were incubated with the indicated ARH (5 µM) in 50 mM potassium phosphate, pH 7.5, 10 mM MgCl$_2$, and 5 mM DTT (total volume 25 µl), at 37° C. for 2-2.5 h or at 30° C. for 2 h or overnight. After termination of the reactions with addition of 6 µl of 5× Laemmli buffer, samples of proteins (30 µg) were separated by SDS-PAGE, in 12% or 4-20% gels, and transferred to nitrocellulose membranes, which were exposed to X-ray films for 10 h (Kodak).

Preparation of radiolabeled poly(ADP-ribose)PARP. [$^{32}$P] auto-poly-ADP-ribosylated PARP ([$^{32}$P]poly(ADP-ribose) PARP), synthesized by incubation (37° C., 10 min), in a 300 µl volume of 100 mM Tris-HCl, pH 8.0, 10 µM [$^{32}$P] NAD (10 mCi/reaction), 10 mM MgCl$_2$, 5 mM DTT, containing 6 µg of poly(ADP-ribose)polymerase (PARP, Biomol), and 6 µg of calf thymus DNA was collected as described for [$^{32}$P]-mono-ADP-ribosylated proteins.

Protein-free poly(ADP-ribose) was prepared using dihydroboronyl-Bio Rex (DHBB) affinity resin as described (Alvarez-Gonzalez et al. (1983) *Anal. Biochem.* 135:69-77) with minor modifications. Briefly, [$^{32}$P]poly(ADP-ribose)PARP (12 µg) in 300 µl of 50 mM MOPS, pH 8.6, containing 6 M guanidine HCl, 0.5 M NH$_2$OH was incubated (37° C., 2 h), before addition of 200 µl of DHBB, and rotation of the mixture at 25° C. overnight. The matrix was washed sequentially with 5 ml of 6 M guanidine HCl in 50 mM MOPS, pH 8.6, 5 ml of 1 M NH$_4$HCO$_3$, pH 8.8, and 5 ml of 250 mM NH$_4$CO$_3$, pH 8.8, followed by elution with 3 ml of water; the eluate containing ~85% of radiolabeled poly(ADP-ribose), was concentrated by evaporation to 500 µl and stored at −20° C.

To prepare [$^{14}$C]poly(ADP-ribose)PARP for HPLC experiments, [$^{32}$P] NAD was replaced by 10 µM [$^{14}$C] NAD (0.5 µCi/reaction).

Poly(ADP-ribose) hydrolysis by autoradiography. [$^{32}$P] poly(ADP-ribose)PARP (500 ng of PARP with poly(ADP-ribose) was incubated (37° C., 2 h) with 2 µM ARH in 25 µl of 50 mM potassium phosphate buffer, pH 7.5, with or without 10 mM MgCl$_2$ and/or 5 mM DTT. Reactions were stopped by adding 6 µl of 5× Laemmli buffer. Samples (20 µl) of proteins were separated by SDS-PAGE in 4-20% gels and transferred to nitrocellulose membranes that were exposed to X-ray film (Kodak) for 10 h.

Hydrolysis of poly(ADP-ribose) by PARG and ARH3. Purified [$^{32}$P] poly(ADP-ribose) (5.5×10$^5$ cpm, ~300 nM ADP-ribose) was incubated for the indicated time at 37° C. in 25 µl of 50 mM potassium phosphate, pH 7.5, containing 10 mM MgCl$_2$ and 5 mM DTT with enzyme or other additions as indicated and terminated by addition of 25 µl of 2× electrophoresis buffer (Invitrogen). [$^{32}$P]AMP was generated by incubation (37° C., 3 h) of 10 µM [$^{32}$P] NAD (10 µCi/reaction) with pyrophosphatase (40 units/mg from SIGMA, 1 mg/ml) in 25 µl of 50 mM KPO$_4$, pH 7.5, and 10 mM MgCl$_2$. [$^{32}$P] ADP-ribose was generated in a 25 µl mixture containing 50 mM KPO$_4$, pH 7.5, 25 µg of activated CTA, 10 µM [$^{32}$P] NAD (10 µCi/reaction), 10 mM MgCl$_2$, and 5 mM DTT, which was incubated at 30° C. overnight. [$^{32}$P] phosphoribosyl-AMP was generated by incubation (37° C., 3 h) of [$^{32}$P] poly(ADP-ribose) (5.5×10$^5$ cpm, ~300 nM ADP-ribose) with Crotalus adamanteus phosphodiesterase (10 mU/reaction), 25 µl of 50 mM KPO$_4$, pH 7.5, 10 mM MgCl$_2$, and 5 mM DTT. Identities of AMP and ADP-ribose standards were confirmed by HPLC on C18 and SAX columns respectively.

High resolution Polyacrylamide Gel Electrophoresis (PAGE). Polyacrylamide (20%) gels (20×20×0.15 cm) containing polyacrylamide and bis(acrylamide), in a ratio of 19:1, 100 mM Tris-borate, pH 8.3, 2 mM EDTA, 4.4 mM ammonium persulfate, and 3.4 mM TEMED with electrophoresis carried out for 2 h at 400V with 50 mM Tris-borate, pH 8.3, 1 mM EDTA, before application of samples (15 µl) were used for analysis of poly(ADP-ribose) degradation. Subsequent electrophoresis at 400V was stopped when bromophenol blue (BPB) had moved 9 cm from the origin. Gels were exposed to X-ray films (Kodak).

HPLC analysis. HPLC, Hewlett-Packard series 1100 equipped with a diode-array spectrophotometric detector set at 254 nm, was used for separation of reaction products. For anion exchange perfusion chromatography, Zorbax SAX column (4.6×250 mm; DuPont, Wilmington Del.) was washed with 20 mM potassium phosphate, pH 4.5, for 30 min, followed by a linear gradient of 0-1M NaCl in the same buffer for 10 min (30-40 min), then same buffer with 1M NaCl for 10 min (40-50 min) at a flow rate of 1 ml/min. Nicotinamide was eluted at 3 min, NAD at 10 min, and ADP-ribose at 40 min. For reverse phase, Discovery C18 column (4.6×250 mm; SUPELCO, Bellefonte Pa.) was used. Samples were separated isocratically with 100 mM potassium phosphate, pH 6.0 containing 7% methanol at a same flow rate of 1 ml/min. ADP-ribose was eluted at 6 min, NAD at 8 min, nicotinamide 9 min.

ADP-ribose binding assay. [$^{14}$C]ADP-ribose was generated by incubation overnight at 30° C. of 80 µM (10 µCi) [adenine-U-$^{14}$C]NAD with 50 µl of RT6.2 solution (5 nmol/h NADase activity; gift from Dr. Sunhee Park, NHLBI, National Institutes of Health, Bethesda, Md.) in 250 µl of 50 mM potassium phosphate, pH 7.5, and purified by HPLC using Zorbax Sax column as described above. [$^{14}$C]ADP-ribose, eluted at 40 min, was stored at −20° C.

To assess protein binding, 1 µM human wild type or D77N/D78N mutant ARH3 was incubated (30° C., 16 h) with 3 µM [$^{14}$C]ADP-ribose in 50 mM potassium phosphate buffer, pH 7.5, without or with 10 mM MgCl$_2$, and/or 5 mM DTT (total volume 100 µl). A sample (90 µl) was applied to a column (0.5×4 cm) of Affi-Gel boronate (100 mg, Bio-Rad) which was equilibrated with 0.1 M glycine, pH 9.0, containing 0.1 M NaCl, with or without 10 mM MgCl$_2$, and/or 5 mM DTT, and eluted with five 1-ml portions of the same solution. The total eluate, containing ARH with bound ADP-ribose was collected for liquid scintillation counting.

Immunofluorescence Microscopy. HepG2 cells (5×10$^4$ cells per well) were grown for 24 h in DMEM with penicillin G (100 units/ml) and streptomycin (100 µg/ml) without or with 10% FBS (GIBCO) in four-well collagen-coated culture slides (Becton Dickinson), and washed three times with 2 ml of PBSCM (PBS with 1 mM CaCl$_2$ and 1 mM MgCl$_2$) before fixation for 20 min with 3% paraformaldehyde (Electron Microscopy Services, Washington, Pa.) in PBSCM. Fixed cells were washed three times with PBSCM, followed by washing three times with PBSCM, and incubation for 1-2 h in 0.5 ml of blocking buffer (PBSCM with 3% BSA, 5% goat serum). After three washes with PBSCM, cells were incubated (4° C., 16 h) with anti-ARH3 antibodies, 5 µg/ml, in blocking buffer and washed three times with PBSCM before incubation for 2 h with fluorescein isothiocyanate-labeled anti-rabbit IgG or Texas red-labeled anti-mouse IgG antibodies (Vector Laboratories), which had been diluted in blocking buffer. After washing with PBSCM, mounting medium without or with 4',6-diamidino-2-phenylindole dihydrochloride (Vectashield, Vector Laboratories) was added, and coverslips were sealed with clear nail polish (Electron Microscopy Services). Images were collected using a Zeiss LSM 510 laser-scanning confocal microscope.

Example 2

Detection of ARH3 mRNA and Protein

ARH3 mRNA and protein in tissues and cells were detected using, respectively, Northern and Western blot analyses. The full-length ARH3 cDNA hybridized with a single ~1.6 kb band in ten mouse tissues tested (FIG. 2A). Similarly, ~39 kDa immunoreactive ARH3 was seen on Western blots of the same tissues (FIG. 2B). Prominent second bands were present in brain and liver with minor secondary bands in heart and kidney (FIG. 2B). The anti-ARH3 antibodies did not react with ARH1 or ARH2 on Western blots.

Immunoreactive ARH3 was present in both cytosolic and nuclear, but not membrane, fractions from mouse brain and liver. In brain, the cytosolic protein migrated slightly faster than that in the nuclear fraction whereas in liver, two proteins of similar size were present in both fractions (FIG. 2C). The cytosol fraction from HepG2 cells contained a band of ~38 kDa, apparently corresponding to the smaller of the immunoreactive proteins in brain and liver cytosol (FIG. 2C).

No ARH3 was detected in the purified HepG2 cell nuclei, in contrast to its presence in the crude and pure nuclear fractions from tissues. The amino acid identity of ARH3 with other enzymes is shown below (Table 2).

TABLE 2*

| | Amino Acid Identity (%) | | | | | | | |
| | Amino Acid Similarity (%) | | | | | | | |
| | hPARG | mPARG | hARH1 | mARH1 | hARH2 | mARH2 | hARH3 | mARH3 |
|---|---|---|---|---|---|---|---|---|
| hPARG | — | 94 | 10 | 11 | 13 | 12 | 19 | 19 |
| mPARG | 98 | — | 10 | 11 | 13 | 13 | 20 | 19 |
| hARH1 | 29 | 29 | — | 82 | 47 | 47 | 22 | 22 |
| mARH1 | 30 | 30 | 92 | — | 45 | 45 | 19 | 19 |
| hARH2 | 35 | 34 | 68 | 66 | — | 85 | 23 | 24 |
| mARH2 | 35 | 34 | 68 | 66 | 93 | — | 23 | 24 |
| hARH3 | 47 | 47 | 41 | 39 | 40 | 38 | — | 92 |
| mARH3 | 49 | 48 | 41 | 39 | 41 | 40 | 97 | — |

*Identity and similarity of amino acid sequences of ARH family proteins and PARG catalytic domain. Percentage identity and similarity of deduced amino acid sequences of ARH proteins and PARG catalytic domain were calculated by the LaserGene software package. Percentage identity is above the diagonal and similarity below. The sets of amino acids considered to be similar are [C], [S, T, P, A, G], [N, D, E, Q], [H, R, K], [M, I, L, V], [F, Y, W]. h; human, m; mouse Example 3

ARH3 Hydrolysis Activity

Mono-ADP-ribosylated substrate proteins for assay were synthesized by cholera toxin A subunit (ADP-ribose-(arginine)-Gαs), pertussis toxin (ADP-ribose-(cysteine)-Gαi/Gαo), *Pseudomonas aeruginosa* exotoxin A (ADP-ribose-(diphthamide)-elongation factor II), or *Clostridium botulinum* C3 enzyme (ADP-ribose-(asparagines)-Rho) (FIG. 3). Each substrate was incubated at 30° C. overnight with mouse or human ARH1, 2, or 3 (5 µM) or BSA, or GST. Radiolabeled products were separated by SDS-PAGE and analyzed by autoradiography. Mouse and human ARH1, as shown previously, hydrolyzed the ADP-ribose-arginine protein products of the cholera toxin-catalyzed reaction but ARH2 or ARH3 did not (FIG. 3A). ARH1, 2, and 3 all failed to hydrolyze mono-ADP-ribosylated proteins synthesized by pertussis toxin, *P. aeruginosa* exotoxin A, or *C. botulinum* C3 enzyme (FIG. 3B).

Poly(ADP-ribose)PARP was used as substrate to assay potential poly(ADP-ribose) hydrolase activities of recombinant ARH1, 2 or 3. Products were identified by autoradiography and HPLC. Fractions (1 ml) were collected for liquid scintillation counting to quantify [$^{14}$C]ADP-ribose, which was eluted in fractions from 34 min to 43 min. Because ARH1 activity may require both DTT and $Mg^{2+}$, depending on species (Takada et al. (1993) *J. Biol. Chem.* 268:17837-17843; Moss et al. (1992) *J. Biol. Chem.* 267:10481-10488), these reactions were performed with or without 10 mM $MgCl_2$, and/or 5 mM DTT. Autoradiography showed that human ARH3 hydrolyzed [$^{32}$P]poly(ADP-ribose) PARP, whereas ARH1 and 2 did not (FIG. 4A). Degradation of [$^{32}$P]poly(ADP-ribose) by ARH3 was enhanced by 10 mM $MgCl_2$ (FIG. 4A). Data were similar with mouse ARH3.

HPLC established that ADP-ribose was the product of the ARH3-catalyzed reaction, based on its co-elution with authentic ADP-ribose, and its co-migration with the product of the poly(ADP-ribose) glycohydrolase (PARG)-catalyzed reaction. Release of ADP-ribose from poly(ADP-ribose) catalyzed by ARH3 was markedly enhanced by 10 mM $MgCl_2$, consistent with its effect in the experiment designed in FIG. 4A (FIG. 4B).

Identity of the main product of the ARH3-catalyzed reaction was confirmed by HPLC using C18 and SAX columns. [$^{14}$C]poly(ADP-ribose)PARP (900 ng, 52,000 cpm, ~2.5 µM ADP-ribose) was incubated (37° C., 2 h) with 2 µM human or mouse ARH3 or 1 nM calf thymus PARG (Biomol), 10 mM $MgCl_2$ and 5 mM DTT, in 100 µl of 50 mM potassium phosphate, pH 7.5, followed by separation of products on a Discovery C18 column as described in Experimental Procedures. Quantification of $^{14}$C in samples (100 µl) of fractions (1 ml) by liquid scintillation counting revealed a peak with a retention time (6 min) corresponding to that of ADP-ribose. Pooled peak fractions (fractions 5 to 7) were concentrated by evaporation to 200 µl, and then separated by Zorbax SAX columns where it was eluted with a retention time of 40 min, corresponding to that of ADP-ribose (FIG. 5B).

Samples of [$^{14}$C] ADP-ribosylated PARP (250 ng, 15,000 cpm, ~850 nM ADP-ribose) were incubated at 37° C. (total volume, 100 µl) with human ARH3 as indicated. Reactions were terminated with addition of 5 µl of o-phosphoric acid (final pH 2-2.5) and placed on dry ice. Just before HPLC analysis, 100 µl of 100 mM potassium phosphate buffer, pH 6.0, containing 7% methanol, were added to each sample and 200 µl of the mixture were applied to HPLC on a Discovery C18 column as described in Experimental Procedures. The rate of release (after 60 min) of ADP-ribose from [$^{14}$C]poly(ADP-ribose)PARP was directly related to hydrolase concentration (FIG. 6A). With 40 nM hydrolase, the initial rate slowed before 10 min, but hydrolysis was continuing at 60 min, with ~75% of the substrate remaining (FIG. 6B).

To obtain reaction products for characterization, protein-free [$^{32}$P]poly(ADP-ribose) (5.5×10$^5$ cpm, ~300 nM ADP-ribose) purified by DHB-Bio-Rex (DHBB) affinity resin was used as substrate. After incubation for 2, 10, or 60 min with human ARH3 (1 µM), mouse ARH3 (1 µM), or PARG (1.5 nM), products were analyzed by high resolution PAGE and quantified by autoradiography. Purified [$^{32}$P]poly(ADP-ribose) was hydrolyzed to lower molecular weight species in a time-dependent manner with all three enzymes (FIG. 7). Migration of the smallest molecular product, and with time the most abundant corresponded to that of ADP-ribose, not phosphoribosyl-AMP, which is generated by phosphodiesterase cleavage of poly(ADP-ribose).

Example 4

Identification of Amino Acids Critical for Activity

To identify amino acids critical for hydrolase activity of ARH3, three mutants with dual amino acid replacements (D77N/D78N, E261Q/E262Q (SEQ ID NO: 3), E238Q/E239Q (SEQ ID NO: 4)) were prepared. Each of the three~39-kDa proteins was ~94% pure as determined by SDS-polyacrylamide gel electrophoresis. It was shown previously that critical vicinal carboxylic amino acids are D60/D61 in ARH1 (Konczalik and Moss (1999) *J. Biol. Chem.* 274:16736-16740) and E755/E756 in PARG (Patel et al. (2005) *Biochem. J.* 388:493-500). PARG activity of these mutants was assessed by incubation with protein-free [$^{32}$P] poly(ADP-ribose), and analysis of products by high-resolution PAGE (20%) (FIG. 8A). Samples without enzyme (Cont) or with 1 µM ARH3 (wild-type or mutant) or 1.5 nM PARG were incubated for 10, or 60 min, as described in Experimental Procedures, before separation of products and radioautography. Both ARH3 (E261Q/E262Q) and ARH3 (E238Q/E239Q) double mutant proteins hydrolyzed poly(ADP-ribose), with catalytic activities similar to that of the wild-type enzyme. ARH3 (D77N/D78N), however, was inactive (FIG. 8A).

Assays were carried out with [$^{14}$C]poly(ADP-ribose) PARP (600 ng, 35,000 cpm, ~2 µM ADP-ribose) replacing [$^{32}$P]poly(ADP-ribose). Samples were incubated without enzyme (Cont) or with 50 nM human ARH3 (wild-type or mutant) or 1 nM PARG before radioassay of ADP-ribose separated by HPLC on a Discovery C18 column as described in Experimental Procedures. In agreement, release of [$^{14}$C] ADP-ribose from [$^{14}$C]poly(ADP-ribose)PARP (600 ng, 35,000 cpm, ~2 µM ADP-ribose) catalyzed by mutants E261Q/E262Q (~98%) and E238Q/E239Q (~97%) was similar to that by wild-type ARH3 (100%). No activity of ARH3 (D77N/D78N) was detected, even when assays containing 5 µM enzyme were incubated overnight (FIG. 8B). Thus, amino acids D77/D78 are critical for ARH3 activity, whereas replacement of the vicinal glutamates corresponding to those that were required for PARG activity in ARH3 (E261Q/E262Q) had no effect on activity (FIG. 8B).

To determine whether the catalytically inactive ARH3 (D77N/D78N) protein was structurally intact, binding of ADP-ribose was measured. After incubation of wild-type or mutant ARH3 (1 µM) with [$^{14}$C]ADP-ribose (3 µM) (30° C., 16 h) without or with 10 mM $MgCl_2$ and/or 5 mM DTT (total volume 100 µl), unbound ADP-ribose was removed by binding to Affi-gel boronate (Bio-Rad), and ARH3 with ADP-ribose bound, was collected for radioassay. In the absence of magnesium, ADP-ribose binding by D77N/D78N and WT ARH3 was increased somewhat by DTT (FIG. 9). Binding was much lower in the presence of magnesium; DTT increased [$^{14}$C]ADP-ribose binding by WT ARH3, but not by the D77N/D78N mutant (FIG. 9). Boiling abolished binding. Binding by WT or mutant ARH3 (D77N/D78N) was similar even though the mutant enzyme was catalytically inactive.

Example 5

Cellular Distribution of ARH3

The localization of ARH3 in HEK293T cells was investigated by cell fractionation, followed by immunoblotting, and by immunofluorescence. After cell fractionation, immunoreactive 39-kDa ARH3 was identified using antibodies against mouse ARH3 amino acids 355-370 of mouse; the antibodies did not react with ARH1 and ARH2. ARH3 was present in both cytosol and membrane fractions (FIG. 10).

Confocal immunofluorescence microscopy with affinity-purified, anti-peptide antibodies was used to evaluate the distribution of ARH3 in HEK293T cells where it was widely distributed in the cytosol. ARH3 immunoreactivity did not colocalize with that of PARP-1 (nuclear), nucleoporin (nuclear envelope), GM130 (Golgi), EEA-1 (endosome), b-catenin (plasma membrane), calnexin (endoplasmic reticula), GAPDH (cytosol), or mitochondrial marker MitoTracker.

Example 6

Methods Used in Experiments Described in Example 7

For synthesis of O-acetyl-[$^{14}$C]ADP-ribose, 2.5 mM [$^{14}$C] β-NAD (5,000,000 cpm) (200 μl) was purified by high performance liquid chromatography (HPLC Hewlett-Packard series 1100) using an Agilent Zorbax Sax column (4.6×250 mm) and isocratic elution with 20 mM sodium phosphate (pH 4.5).

To generate O-acetyl-[$^{14}$C]ADP-ribose, 100 μM [$^{14}$C] β-NAD (200,000 cpm) and acetyl-histone peptide H3 (100 μg) were incubated with Sir2 (25 U, 6.1 μg) in 200 μl of buffer containing 50 mM Tris-HCl (pH 7.0), 2.7 mM KCl, 1 mM MgCl$_2$, and 0.2 mg of BSA for 4 h at 30° C., before separation of substrate and products by reverse-phase high performance liquid chromatography (HPLC Hewlett-Packard series 1100) on a Vydac C18 column (1×25 cm). Isocratic elution (1 ml/min) with 0.05% trifluoroacetic acid in water for 5 min, was followed by linear gradient of 0.05% trifluoroacetic acid in water to 0.05% trifluoroacetic acid in 40% acetonitrile/60% water from 5 min to 47 min, during which the first 15 fractions (1 ml/min) were collected for quantification of $^{14}$C using a liquid scintillation counter (Packard Bioscience Liquid scintillation Analyzer Tri-Carb1600TR). Digital records of chromatograms (absorbance at 214 nm) were analyzed with a Hewlett Packard ChemStation. Data are expressed as pmol of $^{14}$C per fraction; peak: 1, ADP-ribose; 2, O-acetyl-ADP-ribose; 3, β-NAD (FIG. 11).

Mouse ARH3 (2 pmol) and 2.5 μM O-acetyl-[$^{14}$C]ADP-ribose (5,000 cpm) in 200 μl of buffer containing 50 mM potassium phosphate (pH 7.0), 10 mM MgCl$_2$ and 5 mM DTT were incubated for 2 h at 30° C., before separation of substrate and products using RP-HPLC as described below.

To generate O-acetyl-[$^{32}$P]ADP-ribose, 10 μM [$^{32}$P]β-NAD (10 μCi/reaction), acetyl-histone peptide H3 (100 μg) and Sir2 (25 U, 6.1 μg) in 25 μl of buffer containing 50 mM potassium phosphate (pH 7.0), 10 mM MgCl$_2$ and 5 mM DTT were incubated at 30° C. for 4 h. To quantify hydrolysis, 2.5 μM O-acetyl-[$^{32}$P]ADP-ribose and 2 pmol of mouse ARH3 in 25 μl of buffer containing 50 mM KPO$_4$ (pH 7.0), 10 mM MgCl$_2$ and 5 mM DTT were incubated for 2 h at 30° C.

Nucleotides were separated in 20% polyacrylamide gels (200×200×1.5 mm). Electrophoresis was carried out for 2 h at 400V in 50 mM Tris-borate buffer, pH 8.3, with 1 mM EDTA before nucleotides diluted in urea—Tris-borate EDTA (TBE) sample buffer (Novex) were applied to the gel; then electrophoresis was carried for 6 h at 200V. Gels were exposed to X-ray film at −80° C. for autoradiography.

To produce [$^{32}$P]AMP (see FIG. 11C), 10 μM[$^{32}$P]-NAD (10 μCi/reaction) and pyrophosphatase (25 μg) in 25 μl of buffer containing 50 mM potassium phosphate, pH 7.5 and 10 mM MgCl$_2$ were incubated at 37° C. for 3 h.

To produce [$^{32}$P]ADP-ribose (see FIG. 11C), 10 μM [$^{32}$P] NAD (10 μCi/reaction) and 25 μg activated CTA (Prior to assay, CTA was incubated with 100 mM DTT at 30° C. for 15 min.) in 25 μl of buffer containing 50 mM potassium phosphate (pH 7.5), 10 mM MgCl$_2$ and 5 mM DTT were incubated at 30° C. overnight.

Hydrolysis of O-acetyl-[$^{14}$C]ADP-ribose catalyzed by ARH3. Assays containing the indicated concentration of O-acetyl-[$^{14}$C]-ADP-ribose (0.1 to 2 nmol, 1,000 to 20,000 cpm) and 1.5 pmol of ARH3 in 200 μl of buffer (50 mM KPO$_4$ (pH 7.0), 10 mM MgCl$_2$, 5 mM DTT) were incubated at 30° C. for 20 min. Substrate and products were separated using RP-HPLC. Amounts of product were corrected for ADP-ribose produced in the absence of ARH3 before calculation of hydrolysis rates.

Example 7

O-acetyl-ADP-ribose Hydrolase Activity

Because O-acetyl-ADP-ribose was known to be hydrolyzed at alkaline pH Tanny and Moazed (2001), *Proc Natl Acad Sci USA*. 98(2):415-20, Epub Dec. 26, 2000), it was generated at pH 7.0 in the presence of [$^{14}$C-adenine] β-NAD, Sir2, and acetylated histone H3 peptide (FIG. 11A), and the products of Sir2 and ARH3 were analyzed using reverse-phase HPLC at the same pH (FIGS. 11A,B). The products of the ARH3-catalyzed reaction were also analyzed by high resolution-polyacrylamide gel electrophoresis (FIG. 11C). O-acetyl-[$^{14}$C]ADP-ribose hydrolase activity was time and ARH3 dependent (FIG. 12) and essentially completely dependent on Mg$^{2+}$ (FIG. 13A).

O-acetyl-ADP-ribose was hydrolyzed by ARH3 with $V_{max}$=173±8.4 nmol·min$^{-1}$·mg$^{-1}$, $K_m$=7.4±0.7 μM, $k_{cat}$=47.0±0.8 nmol·min$^{-1}$ mg$^{-1}$ (Data are means ±½ the range of values from duplicate assays). ARH3 has a lower $K_m$ for O-acetyl-ADP-ribose than does murine Nudix (Rafty et al. (2002), *J. Biol. Chem.* 277(49):47114-22, Epub Oct. 4, 2002 (7.4μ±0.7 vs. 45.0±0.9 μM), although mNudT5 has a higher $k_{cat}$ (0.78±0.18 s$^{-1}$ vs. 0.0052±0.0033 s$^{-1}$). The $k_{cat}/K_m$ of ARH3 is significantly less than that of mNudT5 (7.02×10$^2$ M$^{-1}$s$^{-1}$ vs. 4.51×10$^4$ M$^{-1}$s$^{-1}$). These differences may reflect suboptimal assay conditions for ARH3 as well as the alternative site for enzyme action.

ARH3 mutants E261-262Q and E238-239Q hydrolyzed of O-acetyl-ADP-ribose at a rate similar to wild type, whereas ARH3 D77-78N was apparently inactive as was PARG (FIG. 13b). ARH3 hydrolyzed O-acetyl-ADP-ribose at a rate >250 times that of ARH1 and ARH2 appeared to be inactive (FIG. 14a). O-acetyl-ADP-ribose hydrolysis by ARH1 was time and ARH1 dependent (FIG. 14b).

ADP-ribose inhibited ARH3-catalyzed hydrolysis of 2.5 μM O-acetyl-ADP-ribose, ~50% at a concentration of ca. 10 μM. Inhibition by ADP-ribose exhibited a $K_i$=8.6 μM whereas β-NAD had relatively little effect (FIG. 15).

Thus, the ~39-kDa ARH3 encoded protein in the human and mouse genomes synthesized in *E. coli* exhibited poly (ADP-ribose) glycohydrolase activity. ARH3 was ubiquitously expressed in mouse and human tissues by both Northern and Western analyses. The protein specifically cleaved the ADP-ribose linkage, as ADP-ribose-arginine, -cysteine, -asparagine, and -diphthamide bonds synthesized enzymatically by bacterial toxin ADP-ribosyltransferases, were not hydrolyzed. The results presented herein demonstrate that the substrate specificity of ARH1, which cleaves the ADP-ribose-arginine linkage, was different from the substrate specificity ARH3. ARH1 and ARH3 are otherwise similar in molecular size (39 kDa), in amino acid sequence and in ability to bind free ADP-ribose. Although PARG and ARH3 appear to be structurally very different with sizes at 111 kDa and 39 kDa, respectively, in fact, the catalytic domains of both proteins exhibit some similarities, with identities in amino acid sequences between PARG and ARH3 being similar to those observed between ARH3 and ARH1. The ARH1, ARH3, and PARG catalytic domains all contain pairs of vicinal acidic amino acids, aspartate or glutamate (Konczalik and Moss (1999) *J. Biol. Chem.* 274:16736-16740; Patel et al. (2005) *Biochem. J.* 388:493-500). In ARH1, the first pair of vicinal aspartates are conserved among ADP-ribose-(arginine) protein hydrolases from bacteria (*Rhodospirillum rubrum*) to humans, and are required for activity (Konczalik and Moss (1999) *J. Biol. Chem.* 274:16736-16740). In PARG, the last pair of glutamates, rather than the first two, are critical (Patel et al. (2005) *Biochem. J.* 388:493-500). Among the three pairs of acidic residues in ARH3, the first set, D77 and D78, is the one necessary for activity. Replacement of the third pair (E261 and E262) with alanine did not affect hydrolase activity significantly. Thus, in this regard, the 39-kDa ARH3 appears to be more similar in structure to ARH1, than to the PARG catalytic site.

Activities of mammalian ADP-ribose-(arginine)protein hydrolases (ARH1) exhibit a dependency on $Mg^{2+}$, and in some species, also require thiol (Takada et al. (1993) *J. Biol. Chem.* 268:17837-17843; Moss et al. (1992) *J. Biol. Chem.* 267:10481-10488). ARH3 activity appears to need $Mg^{2+}$, but not thiol, for cleavage of poly- and generation of mono-ADP-ribose. In this respect, ARH3 and ARH1 from the same species are different. Mutagenesis had shown that replacement of a critical cysteine with serine in the rat ARH1 resulted in loss of the thiol dependence; human ARH1 has a serine at that position and is not thiol dependent (Takada et al. (1993) *J. Biol. Chem.* 268:17837-17843). ARH3 from mouse and human contain cysteines, but not in the position that determines thiol sensitivity in ARH1; thus, not all cysteines conserved across the ARH family.

ARH3 can catalyze the specific hydrolysis of O-acetyl-ADP-ribose, a product of the Sir2-catalyzed, NAD-dependent histone deacetylation reaction. ARH3, although $Mg^{2+}$-dependent, did not require thiol and, indeed, although it contains cysteines, no cysteine is aligned with the critical cysteine that determines thiol dependency in ARH1.

Example 8

Effect of $H_2O_2$ on ARH3-Transfected NIH3T3 cells

To test the role of ARH3 in the cellular response to oxidative stress, NIH3T3 cells were transfected with ARH3 cDNA using Lipofectamin transfection reagent (Invitrogen). After transfection, the cells were cultured and exposed to 200 µg/ml of Hygromycin G (Invitrogen) for 3-4 weeks to select stably transfected clones. Positive clones derived from single Hygromycin G-resistant cells were then isolated by cloning rings and further grown under the same conditions. As controls, NIH3T3 cells were transfected with an empty pcDNA3.1 vector (Invitrogen) and subjected to the same selection and cloning procedures as described above.

The cells were plated in 96-well plates at $1 \times 10^4$ cells/well, and incubated for 24 hours at 37° C. in a humidified incubator. The cells were then challenged with different concentrations of $H_2O_2$ for 24 hours (see FIG. 16). Cell viability was determined by using Cell-Counting Kit-8 (Dojindo). The experiments were repeated twice with similar results. Expression of ARH3 significantly reduced the toxic effect of $H_2O_2$, as indicated by cell viability.

Example 9

ARH3 Inhibits Collagen-Induced Arthritis

This example demonstrates how ARH3 can be used to reduce inflammation in a collagen-induced arthritis (an animal model of rheumatoid arthritis).

DBA/1 LacJ mice provide a murine model of human inflammation. Ten to twenty DBA/1 LacJ mice per group are injected with type II collagen in complete Freund's adjuvant (CII/CFA) on day 0, and with type II collagen in incomplete Freund's adjuvant (CII/IFA) on day 21 to induce arthritis (see FIG. 17). The study groups include animals treated with an expression vector encoding ARH3, control vector or PBS on days −3, 0, 3, 7, 10, 14, 18 and 21. The incidence of arthritis and clinical score are monitored twice weekly. Antigen-specific humoral and cellular immune responses, and local expression of pro-inflammatory cytokines, are also investigated. Treatment with a nucleic acid encoding ARH3 significantly reduces both the percentage of mice that developed arthritis and/or the arthritis clinical score.

In vivo (local) expression of proinflammatory cytokines can also be suppressed by treatment with ARH3. The hind paws of treated animals are removed on day 35. Total RNA is extracted from tissue homogenates, and mRNA of the pro-inflammatory cytokines, such as IL-1 β, are detected by RT-PCR.

It will be apparent that the precise details of the methods or compositions described may be varied or modified without departing from the spirit of the described invention. We claim all such modifications and variations that fall within the scope and spirit of the claims below.

The invention claimed is:

1. A method for catalyzing the release of ADP-ribose from poly(ADP-ribose) or O-acetyl-ADP-ribose, comprising
contacting the poly(ADP-ribose) or O-acetyl-ADP-ribose with an isolated ADP-ribosyl acceptor hydrolase 3 (ARH3) polypeptide, wherein the ARH3 polypeptide comprises:
a) the amino acid sequence set forth as one of SEQ ID NO: 2, 3, 4, or 6;
b) an amino acid sequence at least 95% identical to the amino acid sequence set forth as SEQ ID NO: 2, wherein the polypeptide has poly(ADP-ribose) glycohydrolase activity or O-acetyl-ADP-ribose hydrolase activity;
c) the amino acid sequence set forth as SEQ ID NO: 2, wherein a glutamic acid is substituted for a glutamine at positions 261 and 262; or
d) the amino acid sequence set forth as SEQ ID NO: 2, wherein a glutamic acid is substituted for a glutamine at positions 238 and 239;
thereby catalyzing the release of ADP ribose.

2. The method of claim 1, further comprising adding magnesium to the poly(ADP-ribose) or O-acetyl-ADP-ribose.

3. The method of claim 1, wherein the ARH-3 polypeptide comprises the amino acid sequence set forth as SEQ ID NO: 2.

4. The method of claim 1, wherein the ARH3 polypeptide comprises an amino acid sequence at least 95% identical to the amino acid sequence set forth as SEQ ID NO: 2, wherein the ARH3 polypeptide has poly(ADP-ribose) glycohydrolase activity or O-acetyl-ADP-ribose hydrolase activity.

5. The method of claim 1, wherein the ARH-3 polypeptide comprises the amino acid sequence set forth as SEQ ID NO: 2, but wherein a glutamic acid is substituted for a glutamine at positions 261 and 262.

6. The method of claim 1, wherein the ARH3 polypeptide comprises the amino acid sequence set forth as SEQ ID NO: 2, but wherein a glutamic acid is substituted for a glutamine at positions 238 and 239.

7. The method of claim 1, wherein the ARH3 polypeptide consists of an amino acid sequence at least 95% identical to SEQ ID NO: 2, wherein the ARH3 polypeptide has poly(ADP-ribose) glycohydrolase activity or O-acetyl-ADP-ribose hydrolase activity.

8. The method of claim 1, wherein the ARH3 polypeptide consists of the amino acid sequence set forth as SEQ ID NO: 2 with at most two amino acid substitutions, wherein the ARH3 polypeptide has poly(ADP-ribose) glycohydrolase activity or O-acetyl-ADP-ribose hydrolase activity.

9. The method of claim 1, wherein the ARH3 polypeptide consists of the amino acid sequence set forth as SEQ ID NO: 2.

10. The method of claim 1, further comprising assaying poly(ADP-ribose) glycohydrolase activity.

11. The method of claim 1, further comprising measuring the release of ADP-ribose.

12. The method of claim 1, wherein the ARH-3 polypeptide comprises an amino acid sequence at least 98% identical to the amino acid sequence set forth as SEQ ID NO: 2, wherein the ARH3 polypeptide has poly(ADP-ribose) glycohydrolase activity or O-acetyl-ADP-ribose hydrolase activity.

13. The method of claim 1, wherein the ARH3 polypeptide comprises anamino acid sequence at least 99% identical to the amino acid sequence set forth as SEQ ID NO: 2, wherein the ARH-3 polypeptide has poly(ADP-ribose) glycohydrolase activity or O-acetyl-ADP-ribose hydrolase activity.

14. The method of claim 1, wherein the ARH3 polypeptide comprises the amino acid sequence set forth as SEQ ID NO: 3.

15. The method of claim 1, wherein the ARH3 polypeptide comprises the amino acid sequence set forth as SEQ ID NO: 4.

16. The method of claim 1, wherein the ARH3 polypeptide comprises the amino acid sequence set forth as SEQ ID NO: 6.

17. The method of claim 1, wherein the ARH3 polypeptide consists of the amino acid sequence set forth as SEQ ID NO: 3.

18. The method of claim 1, wherein the ARH3 polypeptide consists of the amino acid sequence set forth as SEQ ID NO: 4.

19. The method of claim 1, wherein the ARH3 polypeptide consists of the amino acid sequence set forth as SEQ ID NO 6.

* * * * *

SEQUENCE LISTING

```
<160> NUMBER OF SEQ ID NOS: 28

<210> SEQ ID NO 1
<211> LENGTH: 1092
<212> TYPE: DNA
<213> ORGANISM: Homo sapiens

<400> SEQUENCE: 1
atggccgcag cggcgatggc ggcagcggca ggtggagggg ctggcgcggc ccgctccctc      60
tcgcgcttcc gaggctgcct ggctggcgcg ctgctcgggg actgcgtggg ctccttctac     120
gaggcccacg acaccgtcga cctgacgtca gtcctgcgtc atgtccagag tctggagccg     180
gaccccggca cgcccgggag tgagcggaca gaagccttgt actacacaga tgacacagcc     240
```

```
atggccaggg ccctggtgca gtccctgcta gccaaggagg cctttgacga ggtggacatg    300
gctcacagat ttgctcagga gtacaagaaa gaccctgaca ggggctatgg tgctggagta    360
gtcactgtct tcaagaagct cctgaacccc aaatgtcgcg atgtctttga gcctgcccgg    420
gcccagttta cgggaaagg ctcctatggc aatggaggtg ccatgcgggt ggctggcatc    480
tccctggcct atagcagtgt ccaggatgtg cagaagtttg cccggctctc ggcccagctg    540
acacacgcct cctccctggg ttacaatggc gccatcctgc aggccctggc tgtgcacctg    600
gccttgcagg gcgagtcttc cagcgagcac tttctcaagc aactcctggg ccacatggag    660
gatctggagg gtgatgccca gtccgtcttg gatgccaggg agttgggcat ggaggagcgt    720
ccatactcca gccgcctgaa gaagattgga gagcttctag accaggcatc ggtgaccagg    780
gaggaagtgg tgtctgagct agggaatggc attgctgcct ttgagtcggt acccaccgcc    840
atctactgct cctacgctg catggagcca gaccctgaga tcccttctgc cttcaatagc    900
ctccaaagga ctctcattta ttccatctca cttggtgggg acacagacac cattgccacc    960
atggctgggg ccattgctgg tgcctactat gggatggatc aggtgccaga gagctggcag    1020
caaagctgtg aaggctacga ggagacagac atcctggccc aaagcctgca ccgtgtcttc    1080
cagaagagtt ga                                                         1092
```

<210> SEQ ID NO 2
<211> LENGTH: 363
<212> TYPE: PRT
<213> ORGANISM: Homo sapiens

<400> SEQUENCE: 2

```
Met Ala Ala Ala Met Ala Ala Ala Gly Gly Gly Ala Gly Ala
1               5                   10                  15

Ala Arg Ser Leu Ser Arg Phe Arg Gly Cys Leu Ala Gly Ala Leu Leu
                20                  25                  30

Gly Asp Cys Val Gly Ser Phe Tyr Glu Ala His Asp Thr Val Asp Leu
            35                  40                  45

Thr Ser Val Leu Arg His Val Gln Ser Leu Glu Pro Asp Pro Gly Thr
        50                  55                  60

Pro Gly Ser Glu Arg Thr Glu Ala Leu Tyr Tyr Thr Asp Asp Thr Ala
65                  70                  75                  80

Met Ala Arg Ala Leu Val Gln Ser Leu Leu Ala Lys Glu Ala Phe Asp
                85                  90                  95

Glu Val Asp Met Ala His Arg Phe Ala Gln Glu Tyr Lys Lys Asp Pro
            100                 105                 110

Asp Arg Gly Tyr Gly Ala Gly Val Val Thr Val Phe Lys Lys Leu Leu
        115                 120                 125

Asn Pro Lys Cys Arg Asp Val Phe Glu Pro Ala Arg Ala Gln Phe Asn
    130                 135                 140

Gly Lys Gly Ser Tyr Gly Asn Gly Gly Ala Met Arg Val Ala Gly Ile
145                 150                 155                 160

Ser Leu Ala Tyr Ser Ser Val Gln Asp Val Gln Lys Phe Ala Arg Leu
                165                 170                 175

Ser Ala Gln Leu Thr His Ala Ser Ser Leu Gly Tyr Asn Gly Ala Ile
            180                 185                 190

Leu Gln Ala Leu Ala Val His Leu Ala Leu Gln Gly Glu Ser Ser Ser
        195                 200                 205

Glu His Phe Leu Lys Gln Leu Leu Gly His Met Glu Asp Leu Glu Gly
```

```
                210                 215                 220
Asp Ala Gln Ser Val Leu Asp Ala Arg Glu Leu Gly Met Glu Glu Arg
225                 230                 235                 240

Pro Tyr Ser Ser Arg Leu Lys Lys Ile Gly Glu Leu Leu Asp Gln Ala
            245                 250                 255

Ser Val Thr Arg Glu Glu Val Val Ser Glu Leu Gly Asn Gly Ile Ala
        260                 265                 270

Ala Phe Glu Ser Val Pro Thr Ala Ile Tyr Cys Phe Leu Arg Cys Met
    275                 280                 285

Glu Pro Asp Pro Glu Ile Pro Ser Ala Phe Asn Ser Leu Gln Arg Thr
290                 295                 300

Leu Ile Tyr Ser Ile Ser Leu Gly Gly Asp Thr Asp Thr Ile Ala Thr
305                 310                 315                 320

Met Ala Gly Ala Ile Ala Gly Ala Tyr Tyr Gly Met Asp Gln Val Pro
                325                 330                 335

Glu Ser Trp Gln Gln Ser Cys Glu Gly Tyr Glu Thr Asp Ile Leu
            340                 345                 350

Ala Gln Ser Leu His Arg Val Phe Gln Lys Ser
        355                 360

<210> SEQ ID NO 3
<211> LENGTH: 363
<212> TYPE: PRT
<213> ORGANISM: Homo sapiens

<400> SEQUENCE: 3

Met Ala Ala Ala Ala Met Ala Ala Ala Gly Gly Gly Ala Gly Ala
1               5                   10                  15

Ala Arg Ser Leu Ser Arg Phe Arg Gly Cys Leu Ala Gly Ala Leu Leu
            20                  25                  30

Gly Asp Cys Val Gly Ser Phe Tyr Glu Ala His Asp Thr Val Asp Leu
        35                  40                  45

Thr Ser Val Leu Arg His Val Gln Ser Leu Glu Pro Asp Pro Gly Thr
    50                  55                  60

Pro Gly Ser Glu Arg Thr Glu Ala Leu Tyr Tyr Thr Asp Asp Thr Ala
65                  70                  75                  80

Met Ala Arg Ala Leu Val Gln Ser Leu Leu Ala Lys Glu Ala Phe Asp
                85                  90                  95

Glu Val Asp Met Ala His Arg Phe Ala Gln Glu Tyr Lys Lys Asp Pro
            100                 105                 110

Asp Arg Gly Tyr Gly Ala Gly Val Val Thr Val Phe Lys Lys Leu Leu
        115                 120                 125

Asn Pro Lys Cys Arg Asp Val Phe Glu Pro Ala Arg Ala Gln Phe Asn
    130                 135                 140

Gly Lys Gly Ser Tyr Gly Asn Gly Gly Ala Met Arg Val Ala Gly Ile
145                 150                 155                 160

Ser Leu Ala Tyr Ser Ser Val Gln Asp Val Gln Lys Phe Ala Arg Leu
                165                 170                 175

Ser Ala Gln Leu Thr His Ala Ser Ser Leu Gly Tyr Asn Gly Ala Ile
            180                 185                 190

Leu Gln Ala Leu Ala Val His Leu Ala Leu Gln Gly Glu Ser Ser Ser
        195                 200                 205

Glu His Phe Leu Lys Gln Leu Leu Gly His Met Glu Asp Leu Glu Gly
    210                 215                 220
```

```
Asp Ala Gln Ser Val Leu Asp Ala Arg Glu Leu Gly Met Glu Glu Arg
225                 230                 235                 240

Pro Tyr Ser Ser Arg Leu Lys Lys Ile Gly Glu Leu Leu Asp Gln Ala
            245                 250                 255

Ser Val Thr Arg Gln Gln Val Val Ser Glu Leu Gly Asn Gly Ile Ala
        260                 265                 270

Ala Phe Glu Ser Val Pro Thr Ala Ile Tyr Cys Phe Leu Arg Cys Met
    275                 280                 285

Glu Pro Asp Pro Glu Ile Pro Ser Ala Phe Asn Ser Leu Gln Arg Thr
290                 295                 300

Leu Ile Tyr Ser Ile Ser Leu Gly Gly Asp Thr Asp Thr Ile Ala Thr
305                 310                 315                 320

Met Ala Gly Ala Ile Ala Gly Ala Tyr Tyr Gly Met Asp Gln Val Pro
                325                 330                 335

Glu Ser Trp Gln Gln Ser Cys Glu Gly Tyr Glu Glu Thr Asp Ile Leu
            340                 345                 350

Ala Gln Ser Leu His Arg Val Phe Gln Lys Ser
            355                 360
```

```
<210> SEQ ID NO 4
<211> LENGTH: 363
<212> TYPE: PRT
<213> ORGANISM: Homo sapiens

<400> SEQUENCE: 4
```

```
Met Ala Ala Ala Met Ala Ala Ala Gly Gly Gly Ala Gly Ala
1               5                   10                  15

Ala Arg Ser Leu Ser Arg Phe Arg Gly Cys Leu Ala Gly Ala Leu Leu
            20                  25                  30

Gly Asp Cys Val Gly Ser Phe Tyr Glu Ala His Asp Thr Val Asp Leu
        35                  40                  45

Thr Ser Val Leu Arg His Val Gln Ser Leu Glu Pro Asp Pro Gly Thr
    50                  55                  60

Pro Gly Ser Glu Arg Thr Glu Ala Leu Tyr Tyr Thr Asp Asp Thr Ala
65                  70                  75                  80

Met Ala Arg Ala Leu Val Gln Ser Leu Leu Ala Lys Glu Ala Phe Asp
                85                  90                  95

Glu Val Asp Met Ala His Arg Phe Ala Gln Glu Tyr Lys Lys Asp Pro
                100                 105                 110

Asp Arg Gly Tyr Gly Ala Gly Val Val Thr Val Phe Lys Lys Leu Leu
            115                 120                 125

Asn Pro Lys Cys Arg Asp Val Phe Glu Pro Ala Arg Ala Gln Phe Asn
130                 135                 140

Gly Lys Gly Ser Tyr Gly Asn Gly Gly Ala Met Arg Val Ala Gly Ile
145                 150                 155                 160

Ser Leu Ala Tyr Ser Ser Val Gln Asp Val Gln Lys Phe Ala Arg Leu
                165                 170                 175

Ser Ala Gln Leu Thr His Ala Ser Ser Leu Gly Tyr Asn Gly Ala Ile
            180                 185                 190

Leu Gln Ala Leu Ala Val His Leu Ala Leu Gln Gly Glu Ser Ser Ser
        195                 200                 205

Glu His Phe Leu Lys Gln Leu Leu Gly His Met Glu Asp Leu Glu Gly
    210                 215                 220

Asp Ala Gln Ser Val Leu Asp Ala Arg Glu Leu Gly Met Gln Gln Arg
225                 230                 235                 240
```

Pro Tyr Ser Ser Arg Leu Lys Lys Ile Gly Glu Leu Asp Gln Ala
            245                 250                 255

Ser Val Thr Arg Glu Glu Val Val Ser Glu Leu Gly Asn Gly Ile Ala
            260                 265                 270

Ala Phe Glu Ser Val Pro Thr Ala Ile Tyr Cys Phe Leu Arg Cys Met
            275                 280                 285

Glu Pro Asp Pro Glu Ile Pro Ser Ala Phe Asn Ser Leu Gln Arg Thr
            290                 295                 300

Leu Ile Tyr Ser Ile Ser Leu Gly Gly Asp Thr Asp Thr Ile Ala Thr
305                 310                 315                 320

Met Ala Gly Ala Ile Ala Gly Ala Tyr Tyr Gly Met Asp Gln Val Pro
                325                 330                 335

Glu Ser Trp Gln Gln Ser Cys Glu Gly Tyr Glu Glu Thr Asp Ile Leu
            340                 345                 350

Ala Gln Ser Leu His Arg Val Phe Gln Lys Ser
            355                 360

<210> SEQ ID NO 5
<211> LENGTH: 1113
<212> TYPE: DNA
<213> ORGANISM: Mus musculus

<400> SEQUENCE: 5
atggcggtgg ctgcggcggc agcagctaca gcgatgtcgg cggcgggggg cggcggggca      60
agtgcggccc gctccatctc gcgcttccga ggttgcctgg cgggcgcgct gctgggagat     120
tgcgtgggcg ctgtctacga ggcacacgat accgtcagcc tggcatcagt cctgagtcac     180
gtcgagagcc tggagccgga cccgggcacg ccgggcagcg cgcggacaga gacactgtac     240
tacacagatg acactgccat gaccagggcc ctggtacagt ccctgctggc caaggaggcc     300
ttcgacgagg tggacatggc tcacaggttt gcccaggaat acaagaagga ccctgacaga     360
gggtatgggg ccggagtcat cactgtcttc aagaaactcc tgaatcccaa gtgccgtgat     420
gtctatgagc ctgcccggc ccagttcaac gggaagggtt cctatggcaa tggggtgcc      480
atgcgggtag caggcatctc gctggcctat agcagtgtcc aagatgtaca agtttgcc       540
cggctctcag cccagctgac ccacgcctct tccctgggct ataacggtgc catcttgcag     600
gccctggctg tgcaccttgc tctgcagggt gtatcatcca gtgagcactt cctcgagcag     660
cttctgggcc acatggagga gctggaaggt gatgcccagt cagtcttgga cgccaaggag     720
ttgggtatgg aggagcgtcc gtactccagc aggctgaaga aggtcggaga gctgctggac     780
caggacgtgt tgagccgaga ggaagtggtg tccgagctag gaatggcat tgccgccttt      840
gaatctgtgc ccaccgccat ctactgcttc ctgcgctgca tggagcctca ccctgagatc     900
ccctccacct tcaacagtct ccagaggact ctcatctact ccatctcact tggtggggac     960
acagacacca tagccaccat ggctggggcc attgctggag cttactatgg gatggaacag    1020
gtgccggaga gctggcagca aagttgtgaa ggctttgagg agacagacgt cctggcccag    1080
agcctgcacc gagtcttcca ggagagctcg taa                                 1113

<210> SEQ ID NO 6
<211> LENGTH: 370
<212> TYPE: PRT
<213> ORGANISM: Mus musculus

<400> SEQUENCE: 6

```
Met Ala Val Ala Ala Ala Ala Ala Thr Ala Met Ser Ala Ala Gly
1               5                   10                  15

Gly Gly Gly Ala Ser Ala Ala Arg Ser Ile Ser Arg Phe Arg Gly Cys
            20                  25                  30

Leu Ala Gly Ala Leu Leu Gly Asp Cys Val Gly Ala Val Tyr Glu Ala
            35              40                  45

His Asp Thr Val Ser Leu Ala Ser Val Leu Ser His Val Glu Ser Leu
50                  55                  60

Glu Pro Asp Pro Gly Thr Pro Gly Ser Ala Arg Thr Glu Thr Leu Tyr
65                  70                  75                  80

Tyr Thr Asp Asp Thr Ala Met Thr Arg Ala Leu Val Gln Ser Leu Leu
                85                  90                  95

Ala Lys Glu Ala Phe Asp Glu Val Asp Met Ala His Arg Phe Ala Gln
        100                 105                 110

Glu Tyr Lys Lys Asp Pro Asp Arg Gly Tyr Gly Ala Gly Val Ile Thr
        115                 120                 125

Val Phe Lys Lys Leu Leu Asn Pro Lys Cys Arg Asp Val Tyr Glu Pro
130                 135                 140

Ala Arg Ala Gln Phe Asn Gly Lys Gly Ser Tyr Gly Asn Gly Gly Ala
145                 150                 155                 160

Met Arg Val Ala Gly Ile Ser Leu Ala Tyr Ser Ser Val Gln Asp Val
                165                 170                 175

Gln Lys Phe Ala Arg Leu Ser Ala Gln Leu Thr His Ala Ser Ser Leu
            180                 185                 190

Gly Tyr Asn Gly Ala Ile Leu Gln Ala Leu Ala Val His Leu Ala Leu
            195                 200                 205

Gln Gly Val Ser Ser Glu His Phe Leu Glu Gln Leu Leu Gly His
        210                 215                 220

Met Glu Glu Leu Glu Gly Asp Ala Gln Ser Val Leu Asp Ala Lys Glu
225                 230                 235                 240

Leu Gly Met Glu Glu Arg Pro Tyr Ser Ser Arg Leu Lys Lys Val Gly
                245                 250                 255

Glu Leu Leu Asp Gln Asp Val Val Ser Arg Glu Glu Val Val Ser Glu
            260                 265                 270

Leu Gly Asn Gly Ile Ala Ala Phe Glu Ser Val Pro Thr Ala Ile Tyr
            275                 280                 285

Cys Phe Leu Arg Cys Met Glu Pro His Pro Glu Ile Pro Ser Thr Phe
        290                 295                 300

Asn Ser Leu Gln Arg Thr Leu Ile Tyr Ser Ile Ser Leu Gly Gly Asp
305                 310                 315                 320

Thr Asp Thr Ile Ala Thr Met Ala Gly Ala Ile Ala Gly Ala Tyr Tyr
                325                 330                 335

Gly Met Glu Gln Val Pro Glu Ser Trp Gln Gln Ser Cys Glu Gly Phe
            340                 345                 350

Glu Glu Thr Asp Val Leu Ala Gln Ser Leu His Arg Val Phe Gln Glu
        355                 360                 365

Ser Ser
    370

<210> SEQ ID NO 7
<211> LENGTH: 357
<212> TYPE: PRT
<213> ORGANISM: Homo sapiens

<400> SEQUENCE: 7
```

Met Glu Lys Tyr Val Ala Ala Met Val Leu Ser Ala Ala Gly Asp Ala
1               5                   10                  15

Leu Gly Tyr Tyr Asn Gly Lys Trp Glu Phe Leu Gln Asp Gly Glu Lys
            20                  25                  30

Ile His Arg Gln Leu Ala Gln Leu Gly Gly Leu Asp Ala Leu Asp Val
        35                  40                  45

Gly Arg Trp Arg Val Ser Asp Asp Thr Val Met His Leu Ala Thr Ala
    50                  55                  60

Glu Ala Leu Val Glu Ala Gly Lys Ala Pro Lys Leu Thr Gln Leu Tyr
65                  70                  75                  80

Tyr Leu Leu Ala Lys His Tyr Gln Asp Cys Met Glu Asp Met Asp Gly
                85                  90                  95

Arg Ala Pro Gly Gly Ala Ser Val His Asn Ala Met Gln Leu Lys Pro
            100                 105                 110

Gly Lys Pro Asn Gly Trp Arg Ile Pro Phe Asn Ser His Glu Gly Gly
        115                 120                 125

Cys Gly Ala Ala Met Arg Ala Met Cys Ile Gly Leu Arg Phe Pro His
    130                 135                 140

His Ser Gln Leu Asp Thr Leu Ile Gln Val Ser Ile Glu Ser Gly Arg
145                 150                 155                 160

Met Thr His His His Pro Thr Gly Tyr Leu Gly Ala Leu Ala Ser Ala
                165                 170                 175

Leu Phe Thr Ala Tyr Ala Val Asn Ser Arg Pro Pro Leu Gln Trp Gly
            180                 185                 190

Lys Gly Leu Met Glu Leu Leu Pro Glu Ala Lys Lys Tyr Ile Val Gln
        195                 200                 205

Ser Gly Tyr Phe Val Glu Glu Asn Leu Gln His Trp Ser Tyr Phe Gln
    210                 215                 220

Thr Lys Trp Glu Asn Tyr Leu Lys Leu Arg Gly Ile Leu Asp Gly Glu
225                 230                 235                 240

Ser Ala Pro Thr Phe Pro Glu Ser Phe Gly Val Lys Glu Arg Asp Gln
                245                 250                 255

Phe Tyr Thr Ser Leu Ser Tyr Ser Gly Trp Gly Gly Ser Ser Gly His
            260                 265                 270

Asp Ala Pro Met Ile Ala Tyr Asp Ala Val Leu Ala Ala Gly Asp Ser
        275                 280                 285

Trp Lys Glu Leu Ala His Arg Ala Phe Phe His Gly Gly Asp Ser Asp
    290                 295                 300

Ser Thr Ala Ala Ile Ala Gly Cys Trp Trp Gly Val Met Tyr Gly Phe
305                 310                 315                 320

Lys Gly Val Ser Pro Ser Asn Tyr Glu Lys Leu Glu Tyr Arg Asn Arg
                325                 330                 335

Leu Glu Glu Thr Ala Arg Ala Leu Tyr Ser Leu Gly Ser Lys Glu Asp
            340                 345                 350

Thr Val Ile Ser Leu
        355

<210> SEQ ID NO 8
<211> LENGTH: 354
<212> TYPE: PRT
<213> ORGANISM: Homo sapiens

<400> SEQUENCE: 8

Met Glu Lys Phe Lys Ala Ala Met Leu Leu Gly Ser Val Gly Asp Ala

```
                1               5                  10                  15

Leu Gly Tyr Arg Asn Val Cys Lys Glu Asn Ser Thr Val Gly Met Lys
                20                  25                  30

Ile Gln Glu Glu Leu Gln Arg Ser Gly Gly Leu Asp His Leu Val Leu
                35                  40                  45

Ser Pro Gly Glu Trp Pro Val Ser Asp Asn Thr Ile Met His Ile Ala
 50                  55                  60

Thr Ala Glu Ala Leu Thr Thr Asp Tyr Trp Cys Leu Asp Asp Leu Tyr
 65                  70                  75                  80

Arg Glu Met Val Arg Cys Tyr Val Glu Ile Val Glu Lys Leu Pro Glu
                85                  90                  95

Arg Arg Pro Asp Pro Ala Thr Ile Glu Gly Cys Ala Gln Leu Lys Pro
                100                 105                 110

Asn Asn Tyr Leu Leu Ala Trp His Thr Pro Phe Asn Glu Lys Gly Ser
                115                 120                 125

Gly Phe Gly Ala Ala Thr Lys Ala Met Cys Ile Gly Leu Arg Tyr Trp
                130                 135                 140

Lys Pro Glu Arg Leu Glu Thr Leu Ile Glu Val Ser Val Glu Cys Gly
145                 150                 155                 160

Arg Met Thr His Asn His Pro Thr Gly Phe Leu Gly Ser Leu Cys Thr
                165                 170                 175

Ala Leu Phe Val Ser Phe Ala Ala Gln Gly Lys Pro Leu Val Gln Trp
                180                 185                 190

Gly Arg Asp Met Leu Arg Ala Val Pro Leu Ala Glu Glu Tyr Cys Arg
                195                 200                 205

Lys Thr Ile Arg His Thr Ala Glu Tyr Gln Glu His Trp Phe Tyr Phe
                210                 215                 220

Glu Ala Lys Trp Gln Phe Tyr Leu Glu Glu Arg Lys Ile Ser Lys Asp
225                 230                 235                 240

Ser Glu Asn Lys Ala Ile Phe Pro Asp Asn Tyr Asp Ala Glu Glu Arg
                245                 250                 255

Glu Lys Thr Tyr Arg Lys Trp Ser Ser Glu Gly Arg Gly Gly Arg Arg
                260                 265                 270

Gly His Asp Ala Pro Met Ile Ala Tyr Asp Ala Leu Leu Ala Ala Gly
                275                 280                 285

Asn Ser Trp Thr Glu Leu Cys His Arg Ala Met Phe His Gly Gly Glu
                290                 295                 300

Ser Ala Ala Thr Gly Thr Ile Ala Gly Cys Leu Phe Gly Leu Leu Tyr
305                 310                 315                 320

Gly Leu Asp Leu Val Pro Lys Gly Leu Tyr Gln Asp Leu Glu Asp Lys
                325                 330                 335

Glu Lys Leu Glu Asp Leu Gly Ala Ala Leu Tyr Arg Leu Ser Thr Glu
                340                 345                 350

Glu Lys

<210> SEQ ID NO 9
<211> LENGTH: 868
<212> TYPE: PRT
<213> ORGANISM: Homo sapiens

<400> SEQUENCE: 9

Met Met Ser Ser Val Gln Lys Asp Asn Phe Tyr Gln His Asn Val Glu
 1               5                  10                  15

Lys Leu Glu Asn Val Ser Gln Leu Ser Leu Asp Lys Ser Pro Thr Glu
```

```
                     20                  25                  30
Lys Ser Thr Gln Tyr Leu Asn Gln His Gln Thr Ala Ala Met Cys Lys
             35                  40                  45
Trp Gln Asn Glu Gly Lys His Thr Glu Gln Leu Leu Glu Ser Glu Pro
         50                  55                  60
Gln Thr Val Thr Leu Val Pro Glu Gln Phe Ser Asn Ala Asn Ile Asp
 65                  70                  75                  80
Arg Ser Pro Gln Asn Asp His Ser Asp Thr Asp Ser Glu Glu Asn
                 85                  90                  95
Arg Asp Asn Gln Gln Phe Leu Thr Thr Val Lys Leu Ala Asn Ala Lys
                100                 105                 110
Gln Thr Thr Glu Asp Glu Gln Ala Arg Glu Ala Lys Ser His Gln Lys
             115                 120                 125
Cys Ser Lys Ser Cys Asp Pro Gly Glu Asp Cys Ala Ser Cys Gln Gln
         130                 135                 140
Asp Glu Ile Asp Val Val Pro Glu Ser Pro Leu Ser Asp Val Gly Ser
145                 150                 155                 160
Glu Asp Val Gly Thr Gly Pro Lys Asn Asp Asn Lys Leu Thr Arg Gln
                 165                 170                 175
Glu Ser Cys Leu Gly Asn Ser Pro Pro Phe Glu Lys Glu Ser Glu Pro
                180                 185                 190
Glu Ser Pro Met Asp Val Asp Asn Ser Lys Asn Ser Cys Gln Asp Ser
             195                 200                 205
Glu Ala Asp Glu Glu Thr Ser Pro Gly Phe Asp Glu Gln Glu Asp Gly
         210                 215                 220
Ser Ser Ser Gln Thr Ala Asn Lys Pro Ser Arg Phe Gln Ala Arg Asp
225                 230                 235                 240
Ala Asp Ile Glu Phe Arg Lys Arg Tyr Ser Thr Lys Gly Gly Glu Val
                 245                 250                 255
Arg Leu His Phe Gln Phe Glu Gly Gly Glu Ser Arg Thr Gly Met Asn
                260                 265                 270
Asp Leu Asn Ala Lys Leu Pro Gly Asn Ile Ser Ser Leu Asn Val Glu
             275                 280                 285
Cys Arg Asn Ser Lys Gln His Gly Lys Lys Asp Ser Lys Ile Thr Asp
         290                 295                 300
His Phe Met Arg Leu Pro Lys Ala Glu Asp Arg Arg Lys Glu Gln Trp
305                 310                 315                 320
Glu Thr Lys His Gln Arg Thr Glu Arg Lys Ile Pro Lys Tyr Val Pro
                 325                 330                 335
Pro His Leu Ser Pro Asp Lys Lys Trp Leu Gly Thr Pro Ile Glu Glu
                340                 345                 350
Met Arg Arg Met Pro Arg Cys Gly Ile Arg Leu Pro Leu Leu Arg Pro
             355                 360                 365
Ser Ala Asn His Thr Val Thr Ile Arg Val Asp Leu Leu Arg Ala Gly
         370                 375                 380
Glu Val Pro Lys Pro Phe Pro Thr His Tyr Lys Asp Leu Trp Asp Asn
385                 390                 395                 400
Lys His Val Lys Met Pro Cys Ser Glu Gln Asn Leu Tyr Pro Val Glu
                 405                 410                 415
Asp Glu Asn Gly Glu Arg Thr Ala Gly Ser Arg Trp Glu Leu Ile Gln
                420                 425                 430
Thr Ala Leu Leu Asn Lys Phe Arg Pro Gln Asn Leu Lys Asp Ala
             435                 440                 445
```

```
Ile Leu Lys Tyr Asn Val Ala Tyr Ser Lys Lys Trp Asp Phe Thr Ala
    450             455                 460

Leu Ile Asp Phe Trp Asp Lys Val Leu Glu Glu Ala Glu Ala Gln His
465             470                 475                 480

Leu Tyr Gln Ser Ile Leu Pro Asp Met Val Lys Ile Ala Leu Cys Leu
                485                 490                 495

Pro Asn Ile Cys Thr Gln Pro Ile Pro Leu Leu Lys Gln Lys Met Asn
            500                 505                 510

His Ser Ile Thr Met Ser Gln Glu Gln Ile Ala Ser Leu Leu Ala Asn
        515                 520                 525

Ala Phe Phe Cys Thr Phe Pro Arg Arg Asn Ala Lys Met Lys Ser Glu
    530                 535                 540

Tyr Ser Ser Tyr Pro Asp Ile Asn Phe Asn Arg Leu Phe Glu Gly Arg
545                 550                 555                 560

Ser Ser Arg Lys Pro Glu Lys Leu Lys Thr Leu Phe Cys Tyr Phe Arg
                565                 570                 575

Arg Val Thr Glu Lys Lys Pro Thr Gly Leu Val Thr Phe Thr Arg Gln
            580                 585                 590

Ser Leu Glu Asp Phe Pro Glu Trp Glu Arg Cys Glu Lys Pro Leu Thr
        595                 600                 605

Arg Leu His Val Thr Tyr Glu Gly Thr Ile Glu Asn Gly Gln Gly
    610                 615                 620

Met Leu Gln Val Asp Phe Ala Asn Arg Phe Val Gly Gly Val Thr
625                 630                 635                 640

Ser Ala Gly Leu Val Gln Glu Glu Ile Arg Phe Leu Ile Asn Pro Glu
                645                 650                 655

Leu Ile Ile Ser Arg Leu Phe Thr Glu Val Leu Asp His Asn Glu Cys
            660                 665                 670

Leu Ile Ile Thr Gly Thr Glu Gln Tyr Ser Glu Tyr Thr Gly Tyr Ala
        675                 680                 685

Glu Thr Tyr Arg Trp Ser Arg Ser His Glu Asp Gly Ser Glu Arg Asp
    690                 695                 700

Asp Trp Gln Arg Arg Cys Thr Glu Ile Val Ala Ile Asp Ala Leu His
705                 710                 715                 720

Phe Arg Arg Tyr Leu Asp Gln Phe Val Pro Glu Lys Met Arg Arg Glu
                725                 730                 735

Leu Asn Lys Ala Tyr Cys Gly Phe Leu Arg Pro Gly Val Ser Ser Glu
            740                 745                 750

Asn Leu Ser Ala Val Ala Thr Gly Asn Trp Gly Cys Gly Ala Phe Gly
        755                 760                 765

Gly Asp Ala Arg Leu Lys Ala Leu Ile Gln Ile Leu Ala Ala Ala Ala
    770                 775                 780

Ala Glu Arg Asp Val Val Tyr Phe Thr Phe Gly Asp Ser Glu Leu Met
785                 790                 795                 800

Arg Asp Ile Tyr Ser Met His Ile Phe Leu Thr Glu Arg Lys Leu Thr
                805                 810                 815

Val Gly Asp Val Tyr Lys Leu Leu Arg Tyr Tyr Asn Glu Glu Cys
            820                 825                 830

Arg Asn Cys Ser Thr Pro Gly Pro Asp Ile Lys Leu Tyr Pro Phe Ile
        835                 840                 845

Tyr His Ala Val Glu Ser Cys Ala Glu Thr Ala Asp His Ser Gly Gln
    850                 855                 860
```

```
Arg Thr Gly Thr
865

<210> SEQ ID NO 10
<211> LENGTH: 17
<212> TYPE: PRT
<213> ORGANISM: Mus musculus

<400> SEQUENCE: 10

Cys Thr Asp Val Leu Ala Gln Ser Leu His Arg Val Phe Gln Glu Ser
1               5                   10                  15

Ser

<210> SEQ ID NO 11
<211> LENGTH: 25
<212> TYPE: DNA
<213> ORGANISM: Artificial Sequence
<220> FEATURE:
<223> OTHER INFORMATION: Synthetic DNA primer

<400> SEQUENCE: 11
taggatccat ggtgggggc tgatt                                          25

<210> SEQ ID NO 12
<211> LENGTH: 26
<212> TYPE: DNA
<213> ORGANISM: Artificial sequence
<220> FEATURE:
<223> OTHER INFORMATION: Synthetic DNA primer

<400> SEQUENCE: 12
tagaattcct agggatctaa tacgga                                        26

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA primer

<400> SEQUENCE: 13
tacccgccaa tggagaagtt caaggctgca                                    30

<210> SEQ ID NO 14
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 14
tagaattctt acttttcttc tgtggacag                                     29

<210> SEQ ID NO 15
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 15
taggatccat ggcggtggct gcggcggca                                     29

<210> SEQ ID NO 16
<211> LENGTH: 29
```

```
<212> TYPE: DNA
<213> ORGANISM: Artificial Sequence
<220> FEATURE:
<223> OTHER INFORMATION: Synthetic DNA primer

<400> SEQUENCE: 16
tagaattctt acgagctctc ctggaagac                              29

<210> SEQ ID NO 17
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 17
tacccgccaa tggagaagta tgtggctgc                              29

<210> SEQ ID NO 18
<211> LENGTH: 32
<212> TYPE: DNA
<213> ORGANISM: Artificial Sequence
<220> FEATURE:
<223> OTHER INFORMATION: Synthetic DNA primer

<400> SEQUENCE: 18
tagaattcct aaagggaaat tacagtgtct tc                          32

<210> SEQ ID NO 19
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 19
taggatccat ggagaaattt aaggctgcg                              29

<210> SEQ ID NO 20
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 20
tagaattctt acttctcctc tgtggacag                              29

<210> SEQ ID NO 21
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 21
taggatccat ggccgcagcg gcgatggcg                              29

<210> SEQ ID NO 22
<211> LENGTH: 29
<212> TYPE: DNA
<213> ORGANISM: Artificial Sequence
```

```
<220> FEATURE:
<223> OTHER INFORMATION: Synthetic DNA primer

<400> SEQUENCE: 22
tagaattctc aactcttctg gaagacacg                                              29

<210> SEQ ID NO 23
<211> LENGTH: 31
<212> TYPE: DNA
<213> ORGANISM: Artificial Sequence
<220> FEATURE:
<223> OTHER INFORMATION: Synthetic DNA primer

<400> SEQUENCE: 23
cttgtactac acaaataaca cagccatggc c                                           31

<210> SEQ ID NO 24
<211> LENGTH: 31
<212> TYPE: DNA
<213> ORGANISM: Artificial Sequence
<220> FEATURE:
<223> OTHER INFORMATION: Synthetic DNA primer

<400> SEQUENCE: 24
ggccatggct gtgttatttg tgtagtacaa g                                           31

<210> SEQ ID NO 25
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 25
cggtgaccag gcagcaagtg gtgtctgag                                              29

<210> SEQ ID NO 26
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 26
ctcagacacc acttgctgcc tggtcaccg                                              29

<210> SEQ ID NO 27
<211> LENGTH: 30
<212> TYPE: DNA
<213> ORGANISM: Artificial Sequence
<220> FEATURE:
<223> OTHER INFORMATION: Synthetic DNA primer

<400> SEQUENCE: 27
gagttgggca tgcagcagcg tccatactcc                                             30

<210> SEQ ID NO 28
<211> LENGTH: 30
<212> TYPE: DNA
<213> ORGANISM: Artificial Sequence
<220> FEATURE:
<223> OTHER INFORMATION: Synthetic DNA primer

<400> SEQUENCE: 28
ggagtatgga cgctgctgca tgcccaactc                                             30
```